(12) United States Patent
Shahaf et al.

(10) Patent No.: US 12,329,902 B2
(45) Date of Patent: Jun. 17, 2025

(54) DRUG DELIVERY DEVICES AND METHODS FOR ADMINISTERING SUBSTANCES TO A BODY CAVITY BY HETEROGENOUS AEROSOLIZATION

(71) Applicant: SIPNOSE LTD, Yokne'am Ilit (IL)

(72) Inventors: Daniel Shahaf, Kibbutz Dganiya (IL); Iris Shichor, Zichron Yaakov (IL)

(73) Assignee: SipNose Ltd., Yokne'am Ilit (IL)

( * ) Notice: Subject to any disclaimer, the term of this patent is extended or adjusted under 35 U.S.C. 154(b) by 1403 days.

(21) Appl. No.: 16/810,226

(22) Filed: Mar. 5, 2020

(65) Prior Publication Data

US 2020/0289768 A1    Sep. 17, 2020

Related U.S. Application Data

(63) Continuation-in-part of application No. 15/982,996, filed on May 17, 2018, now Pat. No. 11,471,618, (Continued)

(30) Foreign Application Priority Data

Dec. 16, 2013    (DE) .......................... 2020131057150

(51) Int. Cl.
*A61M 15/00*    (2006.01)
*A61M 11/00*    (2006.01)
(Continued)

(52) U.S. Cl.
CPC ........ *A61M 15/009* (2013.01); *A61M 11/001* (2014.02); *A61M 11/02* (2013.01);
(Continued)

(58) Field of Classification Search
CPC . A61K 9/0043; A61K 9/5031; A61M 11/001; A61M 11/007; A61M 11/02;
(Continued)

(56) References Cited

U.S. PATENT DOCUMENTS 462,990 A    11/1891    Oppenheimer
3,921,637 A    11/1975    Bennie et al.
(Continued)

FOREIGN PATENT DOCUMENTS

CN    1981886    6/2007
CN    104520198    4/2015
(Continued)

OTHER PUBLICATIONS

Affidavit of Ms. Lia Kaufman dtd Aug. 3, 2020, pp. 1-9, with Facts and Arguments brief, published Aug. 7, 2020 in the Register of the Opposition proceedings in EP 3400047 B1, available at https://register.epo.org/application?number=EP17711702&Ing=en&tab=doclist (last accessed Nov. 9, 2023).
(Continued)

*Primary Examiner* — Annette Dixon
(74) *Attorney, Agent, or Firm* — Foley & Lardner LLP

(57) ABSTRACT

A device for delivering a predetermined volume of a substance within at least one body cavity of a subject includes a predefined volume for containing the predetermined volume of the at least one substance. The device also includes a delivery end for placement in proximity to the body cavity where the delivery end includes at least one orifice of diameter D. The device further includes a valve mechanically connectable to the container, the valve having at least two configurations: (i) an active configuration in which the valve enables delivery of predetermined volume $V_{sub}$ [ml] of the substance and, (ii) an inactive configuration, in which the valve prevents delivery of the predetermined volume $V_{sub}$ [ml] of the substance from the container to the body cavity. The device also includes a fluid tight chamber configured to contain a predetermined volume $V_{gas}$ [ml] of pressurized gas at a predetermined pressure, $P_{gas}$ [barg].

12 Claims, 21 Drawing Sheets

Related U.S. Application Data which is a continuation-in-part of application No. 14/733,143, filed on Jun. 8, 2015, now Pat. No. 11,116,914, application No. 16/810,226 is a continuation-in-part of application No. 16/810,096, filed on Mar. 5, 2020, which is a continuation-in-part of application No. 15/982,630, filed on May 17, 2018, now Pat. No. 11,278,682, which is a continuation-in-part of application No. 14/733,143, filed on Jun. 8, 2015, now Pat. No. 11,116,914, application No. 16/810,226 is a continuation-in-part of application No. 14/433,048, filed as application No. PCT/IL2014/050752 on Aug. 21, 2014, now Pat. No. 11,383,048.

(60) Provisional application No. 62/117,986, filed on Feb. 19, 2015, provisional application No. 62/077,246, filed on Nov. 9, 2014, provisional application No. 62/526,386, filed on Jun. 29, 2017, provisional application No. 62/507,816, filed on May 18, 2017, provisional application No. 61/868,614, filed on Aug. 22, 2013, provisional application No. 61/868,627, filed on Aug. 22, 2013.

(51) Int. Cl.
*A61M 11/02* (2006.01)
*A61M 15/08* (2006.01)

(52) U.S. Cl.
CPC ........ *A61M 15/0035* (2014.02); *A61M 15/08* (2013.01); *A61M 2202/0208* (2013.01); *A61M 2202/0225* (2013.01); *A61M 2202/025* (2013.01); *A61M 2202/0266* (2013.01); *A61M 2202/0291* (2013.01); *A61M 2202/0488* (2013.01); *A61M 2205/3334* (2013.01); *A61M 2205/3337* (2013.01); *A61M 2210/0618* (2013.01); *A61M 2210/0625* (2013.01); *A61M 2210/1089* (2013.01); *A61M 2210/1475* (2013.01)

(58) Field of Classification Search
CPC .......... A61M 15/0003; A61M 15/0028; A61M 15/0031; A61M 15/0033; A61M 15/0045; A61M 15/005; A61M 15/0081; A61M 15/0086; A61M 15/009; A61M 15/08; A61M 2202/04; A61M 2202/064; A61M 2205/0244; A61M 2205/073; A61M 2206/16; A61M 2210/0618; B05B 11/061; B05B 11/062
See application file for complete search history.

(56) References Cited

U.S. PATENT DOCUMENTS

| | | | |
|---|---|---|---|
| 4,017,007 | A | 4/1977 | Riccio |
| 4,114,615 | A | 9/1978 | Wetterlin et al. |
| 4,620,670 | A | 11/1986 | Hughes |
| 5,048,729 | A * | 9/1991 | Pritchard ............ A61M 15/009 222/402.1 |
| 5,307,953 | A | 5/1994 | Regan |
| 5,740,794 | A | 4/1998 | Smith et al. |
| 6,123,228 | A | 9/2000 | Hippensteel |
| 6,186,141 | B1 | 2/2001 | Pike et al. |
| 6,398,074 | B1 | 6/2002 | Bruna et al. |
| 6,708,846 | B1 | 3/2004 | Fuchs et al. |
| 6,971,385 | B1 * | 12/2005 | Flora ................ A61M 15/0045 128/205.21 |
| 7,497,390 | B2 | 3/2009 | Beller |
| 7,726,308 | B1 | 6/2010 | Flora |
| 7,802,569 | B2 | 9/2010 | Yeates et al. |
| 7,900,659 | B2 | 3/2011 | Whitley et al. |
| 8,360,056 | B2 | 1/2013 | Ishizeki et al. |
| 2001/0008637 | A1 | 7/2001 | Hochrainer et al. |
| 2002/0023641 | A1 | 2/2002 | Stadelhofer |
| 2002/0092520 | A1* | 7/2002 | Casper .............. A61M 15/0081 128/200.22 |
| 2002/0092521 | A1 | 7/2002 | Sullivan et al. |
| 2002/0092524 | A1 | 7/2002 | Lockhart et al. |
| 2003/0079743 | A1 | 5/2003 | Genova et al. |
| 2003/0127533 | A1 | 7/2003 | Stihl |
| 2003/0181917 | A1 | 9/2003 | Gertner |
| 2003/0187404 | A1 | 10/2003 | Waldenburg |
| 2003/0209455 | A1 | 11/2003 | Pynson et al. |
| 2004/0050885 | A1 | 3/2004 | Stradella |
| 2004/0153033 | A1 | 8/2004 | Mazzoni |
| 2005/0028812 | A1 | 2/2005 | Djupesland |
| 2006/0067911 | A1 | 3/2006 | Nilsson |
| 2006/0107957 | A1 | 5/2006 | Djupesland |
| 2006/0151629 | A1 | 7/2006 | Vedrine et al. |
| 2006/0213514 | A1 | 9/2006 | Price et al. |
| 2006/0254583 | A1 | 11/2006 | Deboeck et al. |
| 2006/0254585 | A1 | 11/2006 | Ishizeki et al. |
| 2007/0051362 | A1 | 3/2007 | Sullivan et al. |
| 2007/0060868 | A1 | 3/2007 | Tsutsui |
| 2007/0125371 | A1 | 6/2007 | Djupesland |
| 2007/0151562 | A1 | 7/2007 | Jones et al. |
| 2007/0154407 | A1 | 7/2007 | Peters et al. |
| 2007/0256688 | A1 | 11/2007 | Schuster et al. |
| 2008/0029084 | A1* | 2/2008 | Costantino ........ A61M 15/0086 128/200.14 |
| 2008/0092887 | A1 | 4/2008 | Hodson et al. |
| 2008/0210229 | A1 | 9/2008 | Corbacho |
| 2009/0166379 | A1 | 7/2009 | Wright et al. |
| 2009/0285849 | A1 | 11/2009 | Barsanti et al. |
| 2009/0314293 | A1 | 12/2009 | Djupesland |
| 2010/0083963 | A1 | 4/2010 | Wharton et al. |
| 2010/0282246 | A1 | 11/2010 | Djupesland |
| 2010/0331765 | A1 | 12/2010 | Sullivan et al. |
| 2011/0048414 | A1 | 3/2011 | Hoekman |
| 2011/0088690 | A1 | 4/2011 | Djupesland et al. |
| 2011/0168172 | A1 | 7/2011 | Patton |
| 2011/0283996 | A1 | 11/2011 | Abrams |
| 2012/0291779 | A1 | 11/2012 | Haartsen et al. |
| 2013/0096495 | A1 | 4/2013 | Holmqvist et al. |
| 2013/0180524 | A1 | 7/2013 | Shahaf |
| 2013/0267864 | A1 | 10/2013 | Addington et al. |
| 2013/0299607 | A1 | 11/2013 | Wilkerson et al. |
| 2013/0345673 | A1 | 12/2013 | Ferreri et al. |
| 2014/0060532 | A1 | 3/2014 | Hodges et al. |
| 2015/0122257 | A1 | 5/2015 | Winkler et al. |
| 2015/0144129 | A1 | 5/2015 | Djupesland |
| 2015/0174343 | A1 | 6/2015 | Muellinger et al. |
| 2015/0209325 | A1 | 7/2015 | Najarian et al. |
| 2015/0258287 | A1 | 9/2015 | Shahaf et al. |
| 2015/0297845 | A1 | 10/2015 | Shahaf et al. |
| 2016/0129205 | A1 | 5/2016 | Shahaf et al. |
| 2018/0072480 | A1 | 3/2018 | Genosar |
| 2018/0110922 | A1 | 4/2018 | Dunki-Jacobs et al. |
| 2019/0015613 | A1 | 1/2019 | Shahaf et al. |
| 2019/0060168 | A1 | 2/2019 | Koska |
| 2020/0197631 | A1 | 6/2020 | Stedman et al. |
| 2020/0197633 | A1 | 6/2020 | Shahaf et al. |
| 2020/0289768 | A1 | 9/2020 | Shahaf et al. |
| 2020/0289769 | A1 | 9/2020 | Poullain |
| 2020/0306463 | A1 | 10/2020 | Shahaf et al. |

FOREIGN PATENT DOCUMENTS

| | | |
|---|---|---|
| CN | 107580513 | 1/2018 |
| DE | 19502725 | 8/1996 |
| DE | 19 70 806 | 9/1998 |
| DE | 202013105715 U1 | 2/2014 |
| EP | 1 023 098 B1 | 9/2004 |
| EP | 1 752 176 A1 | 2/2007 |
| EP | 2 002 856 A1 | 12/2008 |
| EP | 2030645 A1 | 3/2009 |
| EP | 2 922 770 | 9/2015 |
| GB | 724974 | 2/1953 |
| GB | 2415376 A | 12/2005 |
| JP | 2002-505981 A | 2/2002 |

(56) References Cited

FOREIGN PATENT DOCUMENTS

| WO | 90/12567 A1 | 11/1990 |
|---|---|---|
| WO | WO-02/505981 | 9/1999 |
| WO | WO-99/46055 | 9/1999 |
| WO | WO-99/58180 | 11/1999 |
| WO | WO-02/055133 A2 | 7/2002 |
| WO | WO-02/060517 A2 | 8/2002 |
| WO | WO-2009/002267 | 12/2008 |
| WO | 2012/029064 A1 | 3/2012 |
| WO | WO-2012/105236 A1 | 8/2012 |
| WO | 2013/0128447 A1 | 9/2013 |
| WO | WO-2015/025324 A1 | 2/2015 |
| WO | WO-2016/054742 | 4/2016 |
| WO | WO-2016/071914 A1 | 5/2016 |
| WO | WO-2016/199135 A1 | 12/2016 |
| WO | WO-2018/051371 | 3/2018 |
| WO | WO-2019/003216 A1 | 1/2019 |
| WO | WO-2019/073165 | 4/2019 |
| WO | WO-2019/079335 | 4/2019 |
| WO | WO-2019/220443 A1 | 11/2019 |
| WO | WO-2020/154182 | 7/2020 |

OTHER PUBLICATIONS

Pharmaseed Ltd., Author: N/A, Title: Brain and Blood PK Profile Following Intranasal Topirmate Administration—Comparison Between SipNose and Other Nasal Devices ("Pharmaseed"), pp. 1-43, with Petition in response to Patentee's observations (62 pages total), published Mar. 4, 2021 in the Register of the Opposition proceedings in EP 3400047 B1, available at https://register.epo.org/application?number=EP17711702&lng=en&tab=doclistDdocument E16) (last accessed Nov. 9, 2023).

Sipnose, Author: N/A, Title: Preclinical Device S1A2NP8 Batch Release Form ("SipNose"), pp. 1-2, with Petition (21 pages total), published Mar. 4, 2021 in the Register of the Opposition proceedings in EP 3400047 B1, available at https://register.epo.org/application?number=EP17711702&lng=en&tab=doclist (last accessed Nov. 9, 2023).

Affidavit of Lia Kaufman.

Brain and Blood PK Profile Following Intranasal Topirmate Administration—Comparison Between SIPNOSE and other Nasal Devices.

Sample Batch Release Form—S1A2NP8 Pre-Clinical Devices.

Damm et al., "Intranasal Volume and Olfactory Function", Chemical Senses, 2002, pp. 831-839, vol. 27, Oxford University Press.

Derendorf et al., "Molecular and clinical pharmacology of intranasal corticosteroids: clinical and therapeutic implications", Allergy, 2008, pp. 1292-1300, vol. 63, 2008 Blackwell Munksgaard.

Doose et al., "Single-dose pharmacokinetics and effect of food on the bioavailability of topiramate, A novel antiepileptic drug", Journal of Clinical Pharmacology, 1996, pp. 884-891, vol. 36.

Ganger et al., "Tailoring Formulations for Intranasal Nose-to-Brain Delivery: A Review on Architecture, Physico-Chemical Characteristics and Mucociliary Clearance of the Nasal Olfactory Mucosa", Pharmaceutics, 2018, pp. 1-28, vol. 10, No. 116.

Khan et al., "Progress in brain targeting drug delivery system by nasal route", Journal of Controlled Release, 2017, pp. 364-389, vol. 268, Elsevier B.V.

Lammi et al., "Treatment with intranasal iloprost reduces disease manifestations in a murine model of previously established COPD", The American Journal of Physiology—Lung Cellular and Molecular Physiology, 2016, pp. L630-L638, vol. 310, 2016 American Physiological Society.

Leombruni et al., "Treatment of obese patients with binge eating disorder using topiramate: a review", Neuropsychiatric Disease and Treatment, 2009, pp. 385-392, vol. 5, Dove Medical Press Ltd.

Massolt et al., "Appetite suppression through smelling of dark chocolate correlates with changes in ghrelin in young women", Regulatory Peptides, 2010, pp. 81-86, vol. 161, 2010 Elsevier B.V.

Puhakka et al., "The common cold: Effects of intranasal fluticasone propionate treatment", The Journal of Allergy and Clinical Immunology, 1998, pp. 726-731, vol. 101, No. 6, Part 1, Mosby, Inc.

Ramaekers et al., "Odors: appetizing or satiating? Development of appetite during odor exposure over time", International Journal of Obesity, 2014, pp. 650-656, vol. 38, 2014 Macmillan Publishers Limited.

Scheibe et al., "Intranasal Administration of Drugs", Archives of Otolaryngology—Head & Neck Surgery, Jun. 2008, pp. 643-646, vol. 134, No. 6, 2008 American Medical Association.

Schiffman et al., "Taste and smell perception affect appetite and immunity in the elderly", European Journal of Clinical Nutrition, 2000, pp. S54-S63, Suppl 3, 2000 Macmillan Publishers Ltd.

Schriever et al., "Size of nostril opening as a measure of intranasal volume", Physiology & Behavior, 2013, pp. 3-5, vol. 110-111, 2012 Elsevier Inc.

Yeomans, "Olfactory influences on appetite and satiety in humans", Physiology and Behavior, 2006, pp. 1-14, vol. 89, No. 1.

PCT International Preliminary Report on Patentability for International Application No. PCT/IL2014/050752, dated Feb. 23, 2016.

PCT International Search Report for International Application No. PCT/IL2014/050752, dated Dec. 18, 2014.

PCT International Written Opinion for International Application No. PCT/IL2014/050752, dated Dec. 18, 2014.

* cited by examiner

Fig. 1A

Initial aerosol portion

Steady state aerosol portion

Fig. 1B

DRUG DELIVERY DEVICES AND METHODS FOR ADMINISTERING SUBSTANCES TO A BODY CAVITY BY HETEROGENOUS AEROSOLIZATION

CROSS REFERENCE TO RELATED APPLICATIONS

This application is a Continuation-in-Part of U.S. application Ser. No. 15/982,996, filed on May 17, 2018 which is a Continuation-in-Part of U.S. Non-Provisional application Ser. No. 14/733,143 filed on Jun. 8, 2015 which claims priority to and the benefit of U.S. Provisional Application Nos. 62/117,986 filed on Feb. 19, 2015 and 62/077,246 filed on Nov. 9, 2014. U.S. application Ser. No. 15/982,996 also claims priority to and the benefit of U.S. Provisional Application No. 62/526,386 filed on Jun. 29, 2017.

This Application is a Continuation-in Part of U.S. application Ser. No. 16/810,096 filed Mar. 5, 2020, which is a Continuation-In-Part of U.S. application Ser. No. 15/982,630, filed on May 17, 2018 which is a Continuation-in-Part of U.S. Non-Provisional application Ser. No. 14/733,143 filed on Jun. 8, 2015 which claims priority to and the benefit of U.S. Provisional Application Nos. 62/117,986 filed on Feb. 19, 2015 and 62/077,246 filed on Nov. 9, 2014. U.S. application Ser. No. 15/982,630 also claims priority to and the benefit of U.S. Provisional Application No. 62/507,816 filed on May 18, 2017.

Further, this application is a Continuation-in-Part of U.S. application Ser. No. 14/433,048 filed on Apr. 2, 2015, which is National Phase Entry of PCT/IL2014/050752 filed on Aug. 21, 2014, which claims the benefit of and priority to U.S. Provisional Application No. 61/868,614 filed on Aug. 22, 2013, U.S. Provisional Application No. 61/868,627 filed on Aug. 22, 2013, and German Application No. 2020131057150 filed on Dec. 16, 2013.

The contents of the above applications are all incorporated by reference as if fully set forth herein in their entirety.

FIELD OF THE INVENTION

The present invention generally pertains to drug delivery means and methods for administering substances to a body cavity by heterogenous aerosolization. More specifically, the present invention relates to intranasal nose to brain drug delivery.

BACKGROUND OF THE INVENTION

Nasal mucosa and especially the olfactory mucosa are highly suitable for drug delivery. Drug transport via neuronal connections appears to be the most relevant pathway to reach the central nervous system (CNS). Gänger and Schindowski discloses that direct nose to brain (N2B) delivery of therapeutic substances is reported to potentially have a wide range of advantages, such as bypassing the blood-brain barrier and increased patient compliance compared to intrathecal delivery. However, N2B targeting also has its limitations: exact dosing of intranasally applied drugs is still an unsolved challenge. Commonly, intranasally applied substances undergo a rapid elimination by mucociliary clearance and by drainage to the lower part of the nose or to the pharynx. Both mucociliary clearance and by drainage may vary with the dosage form. Furthermore, the anatomy of nasal cavities differs considerably between individuals. Therefore, administration techniques display a broad variation and need to be tailored to an individual's anatomic characteristics. Moreover, the dosage volume is restricted as of limited dispersion of the drug on and in the nasal tissue, that causes dripping and/or swallowing of the liquid formulation. Also, as the upper parts of the nasal cavity are small and narrow, a challenge of reaching this area in a non-invasive procedure arises, and a very efficient delivery is needed. compared to the lower parts of the nose. As for the formulation, in the literature it is disclosed that it is important not to use substances with mucosal toxicity or substances causing irritation or allergic reactions. The health status of the patient is also important, as there may occur problems with the functionality of intranasal delivery devices in patients suffering from allergies or who have a cold. Furthermore, it should be ensured that the frequent use of these devices does not harm the nasal mucosal surface. Another necessity for safe and efficient N2B targeting is reproducibility of drug administration the upper area of the nasal cavity including to the olfactory region. Adjacent regions, such as the respiratory region, have a large concentration of blood vessels and thus favor a systemic uptake. Another unsolved issue is the delivery of high molecular weight substances. Although some studies report substantially weight-independent transport, the permeation of the epithelial barrier of endocytosis usually depends on the hydrodynamic radius. Substances smaller than 400 Daltons will diffuse freely while substances of 1000 Daltons or more appear to become stuck in the mucus. It is suggested that for efficient CNS delivery substances have to be linked to a ligand enhancing bioavailability. Once the CNS is reached, there is still the problem of targeting the drug to the specific site of action, see Ganger, Stella, and Katharina Schindowski. "Tailoring formulations for intranasal nose-to-brain delivery: A review on architecture, physico-chemical characteristics and mucociliary clearance of the nasal olfactory mucosa." Pharmaceutics 10.3 (2018): 116. Thus, only highly efficient delivery method will reduce those limitations either with or without specified ligands and/or specified formulations.

Ganger and Schindowski further discloses that nasal pump sprays and droppers are limited to liquid- or lipid-based formulations and that intranasally applied liquids hardly reach the olfactory cleft. If the drug is not able to reach the olfactory region efficiently, it has a reduced chance to be transported to the CNS, but is cleared by mucociliary clearance or absorbed systemically by blood vessels instead, see Scheibe, M.; Bethge, C.; Witt, M.; Hummel, T.; Article, 0. Intranasal administration of drugs. *Arch. Otolaryngol; Head. Neck Surg.* 2008, 134, 643-646; Damm, M.; Vent, J.; Schmidt, M.; Theissen, P.; Eckel, H. E.; Lötsch, J.; Hummel, T. Intranasal volume and olfactory function. *Chem. Senses* 2002, 27, 831-839; and Schriever, V. A.; Hummel, T.; Lundström, J. N.; Freiherr, J. Size of nostril opening as a measure of intranasal volume. *Physiol. Behav.* 2013, 110-111.

Onzetra® Xsail®, commercially available from OptiNose AS, Oslo, Norway was reported to deliver a therapeutic agent into the upper posterior sector of the nose and at the same time reduce drug deposition in the lower nasal segments. ViaNase™, commercially available from Kurve Technology, Inc. (US) consists of a sealed nosepiece and a device where an active vortex of nebulized particles is created. Both N2B devices are suitable for particulate formulations, yet currently there are hardly any devices available for the efficient and reproducible administration of formulations mainly viscous semisolid formulations like hydrogels, see Ganger and Schindowski p. 19-20, incorporated herein as a reference and powder formulations Blow- Fill-Seal (BFS) technology is a manufacturing technique used to produce small: (0.1 mL) and large volume, (500 mL) liquid-filled containers. The basic concept of blow-fill-seal and form-fill-seal (FFS), interchangeably refers hereinafter as BFS, is that a container is formed, filled, and sealed in a continuous process without human intervention, in a sterile enclosed area inside a machine. Thus, this technology can be used to aseptically manufacture sterile pharmaceutical liquid dosage forms. The process is multi-stepped: first: pharmaceutical-grade plastic resin is vertically heat extruded through a circular throat to form a hanging tube (parison). This extruded tube is then enclosed within a two-part mold and the tube is cut above the mold. The mold is transferred to the filling zone, a sterile filling space, where filling needles (mandrels) are lowered and used to inflate the plastic to form the container within the mold. Following the formation of the container, the mandrel is used to fill the container with liquid. Following filling, the mandrels are retracted and a secondary top mold seals the container. All actions take place inside a sterile shrouded chamber inside the machine. The product is then discharged to a non-sterile area for labeling, packaging and distribution. BFS technology reduces personnel intervention, making it a more robust method for the aseptic preparation of sterile pharmaceuticals. BFS is used for the filling of vials for parenteral preparations and infusions, eye drops and inhalation products. Generally, the plastic containers are made up of polyethylene and polypropylene.

Currently commercialized pressurized metered dose inhalers (pMDI) comprise a valved holding chamber (VHC) which reduces low-nasal track deposition as the aerosol is not released with a high plume velocity from the spacer. VHCs reduce the speed of the aerosol particles in the mouth and throat region; reduce the total dose available for inhalation due to drug deposition onto the inner wall of the VHC caused by electrostatic charge deposition, sedimentation by gravity, and inertial deposition due to the high plume velocity. More than that, the latest review shows that the shape of the plumes produced by nebulizers, spray pumps and metered dose inhalers does not match the triangular-shaped nasal vestibule and labyrinthine geometry beyond the nasal valve. Particles present in the periphery of the plume penetrate to the lower part of the nasal cavity and result in systemic and pulmonary delivery, but the requirement for efficient nasal delivery to brain is targeting the drug to the upper part of the nasal valve see Khan, Abdur Rauf, et al. "Progress in brain targeting drug delivery system by nasal route." Journal of Controlled Release 268 (2017): 364-389. U.S. Pat. No. 7,802,569 discloses a low-shear aerosol emitter which is configured to reduce the velocity of a large liquid aerosol flow by directing a counterflow air jet into a second direction of flow that is opposed to the first direction of flow against the large liquid aerosol flow and by generating a sheath air flow for minimizing aerosol deposition on the chamber, to enable respirable particles with an aerodynamic diameter of 1 µm-7 µm. This device produces a mushroom-like ever-widening plume which is not suitable for N2B drug delivery.

It is therefore a long felt need to provide a system which can deliver high-plume velocity low shear-pressure drug delivery devices and methods for administering substance to a body cavity.

SUMMARY OF THE INVENTION

This application incorporates herein by reference the contents of U.S. application Ser. No. 15/982,996 in its entirety.

It is an object of the present invention to disclose drug delivery devices and methods for administering substances to a body cavity by heterogenous aerosolization.

It is another object of the present invention to provide a device for delivering either one or more substances within at least one body cavity, characterized by at least one vial comprising $V_{sub}$ [ml or mg] of said substances; said vial having fluid inlet and a fluid discharging outlet of diameter D [mm], configured for placement in proximity to said body cavity; said fluid inlet configured by means of size and shape to interface in a sealable manner with at least one puncturing member, configured to, upon coupling to said fluid inlet, piercing the same, thereby providing said substances in a fluid communication, via at least one valve, with at least one chamber configured to accept pressurized fluid at volume $V_{PF}$ [ml] and pressure $P_{PF}$ [barg]; said valve is commutable from an CLOSE to an OPEN CONFIGURATION within a short period of time, being less than 500 milliseconds (dT); at said OPEN CONFIGURATION, said pressurized fluid flows from said chamber, via said fluid inlet, entrains said substances, erupts via said fluid discharging outlet to within said body cavity in the form of aerosol, such that the release time of said $V_{sub}$ [ml or mg] of said substances and said $V_{PF}$ [ml] of said pressurized fluid, $dT_{release}$ is less than 500 milliseconds; wherein the aerosol composition exiting said fluid discharging outlet into said body cavity is characterized by a bi-modal spray pattern, comprising a first pattern and a second pattern; further wherein said first pattern is characterized by (a) Plume angle is in the range of 5°±4°; (b) width of plume at 6 cm from the nozzle is in the range of 4 mm±3 mm; and, said second pattern is characterized by (a) Plume angle is in the range of 35°±10°; (b) width of plume at 6 cm from the nozzle is in the range of 30 mm±10 mm; further wherein the mean particle's size in said first pattern is larger than the mean particle's size in said second pattern.

It is another object of the present invention to provide the device as defined above, wherein said vial is selected from a BFS.

It is another object of the present invention to provide a method of delivering a predetermined volume $V_{sub}$ [ml or mg] of at least one substance within at least one body cavity of a subject, comprising steps of:

(a) providing at least one pierceable vial with $V_{sub}$ [ml or mg] of said substances; said vial having at least one fluid inlet port of diameter $D_{in}$ [mm] and at least one fluid discharging outlet port of diameter $D_{out}$ [mm], configured for placement in proximity to said body cavity;

(b) placing said delivery end in proximity to said body cavity;

(c) configuring said fluid inlet by means of size and shape to interface a puncturing member, so that upon coupling to said fluid inlet port, piercing of the same, thereby providing said substances in a fluid communication, with at least one chamber configured to accept pressurized fluid at volume $V_{PF}$ [ml] and pressure $P_{PF}$ [barg]; and, (d) facilitating the flow of said pressurized fluid from said chamber, via said fluid inlet, entrains said substances, erupts via said fluid discharging outlet port into said body cavity in the form of aerosol, such that the release time of said $V_{sub}$ [ml or mg] of said substances and said $V_{PF}$ [ml] of said pressurized fluid, $dT_{release}$ is less than 500 milliseconds;

wherein the aerosol composition exiting said fluid discharging outlet into said body cavity is characterized by a bi-modal spray pattern, comprising a first pattern and a second pattern; further wherein said first pattern is characterized by (a) Plume angle is in the range of 5°±4°; (b) width of plume at 6 cm from the nozzle is in the range of 4 mm±3 mm; and, said second pattern is characterized by (a) Plume angle is in the range of 35°±10°; (b) width of plume at 6 cm from the nozzle is in the range of 30 mm±10 mm; further wherein the mean particle's size in said first pattern is larger than the mean particle's size in said second pattern.

It is another object of the present invention to disclose a device as defined in any of the above, wherein at least one of the following is true: the body orifice is a nasal cavity, a mouth, a throat, an ear, a vagina, a rectum, a urethra, and any combination thereof; the pressurized gas is selected from a group consisting of air, nitrogen, oxygen, carbon dioxide, helium, neon, xenon and any combination thereof; during dispensing of the at least one substance, a mixture of the predetermined volume $V_{gas}$ [ml] of the pressurized gas with the predetermined volume $V_{sub}$ [ml] of the substance entrained within it forms a plume of aerosol; the aerosol having a predetermined distribution, the distribution being either homogeneous or heterogeneous, the heterogeneous distribution is selected from a group consisting of: an arbitrary distribution, a distribution in which the density of the at least one substance within the mixture follows a predetermined pattern, and any combination thereof; characteristics of the aerosol selected from a group consisting of: particle size, particle shape, particle distribution, and any combination thereof, are determinable from characteristics of the device selected from a group consisting of: the predetermined volume of the pressurized gas, the predetermined volume of the substance, the predetermined pressure of the pressurized gas, the predetermined orifice size, and any combination thereof; at least one the substance is selected from a group consisting of a gas, a liquid, a powder, an aerosol, a slurry, a gel, a suspension and any combination thereof; at least one the substance is stored under one of the followings: an inert atmosphere; under vacuum and a pressure above ambient pressure to prevent reactions during storage; a dose-response curve is substantially linear for brain concentration of the substance when administered nasally via the device; and a dose-response curve for brain concentration having a fit selected from a group consisting of logarithmic, parabolic, exponential, sigmoid, power-low, and any combination thereof; of the substance when administered nasally via the device.

It is another object of the present invention to disclose a device as defined in any of the above, wherein the container is a capsule having a main longitudinal axis, the capsule comprising a number n of compartments, the capsule configured to contain the predetermined volume $V_{sub}$ [ml] of the at least one substance, the volume $V_{sub}$ [ml] of the at least one substance containable in at least one of then compartments; at least one of the following being true: the number n of the compartments is an integer greater than or equal to 1; at least one the compartment has cross-section with shape selected from a group consisting of: wedge shaped, circular, oval, elliptical, polygonal, annular, and any combination thereof; for the number n of compartments being an integer greater than 1, at least two the compartments have different volumes; for the number n of compartments being an integer greater than 1, at least two the compartments have the same volume; for the number n of compartments being an integer greater than 1, at least two the compartments have different cross-sectional areas; for the number n of compartments being an integer greater than 1, at least two the compartments have the same cross-sectional area; for the number n of compartments being an integer greater than 1, at least two the compartments contain different substances; for the number n of compartments being an integer greater than 1, at least two the compartments contain the same substance; for the number n of compartments being an integer greater than 1, at least two the compartments are disposed coaxially around the main longitudinal axis of the capsule; for the number n of compartments being an integer greater than 1, at least two the compartments are disposed sequentially along the main longitudinal axis of the capsule; for the number n of compartments greater than 1, the plurality of substances mix during the dispensing; and for the number n of compartments greater than 1, the plurality of substances react during the dispensing.

It is another object of the present invention to disclose a device as defined in any of the above, wherein the container comprises a port fluidly connectable to the exterior of the device, the port configured such that the at least one substance is insertable into the chamber via the port.

It is another object of the present invention to disclose a device as defined in any of the above, wherein the device comprises a port cover configured to provide an air-tight closure for the port, the port cover slidable along the device, rotatable around the device, rotatable around a hinge on the exterior of the device and any combination thereof.

It is another object of the present invention to disclose a device as defined in any of the above, wherein the pressurized fluid entrains the substance in a pulsed manner, such that a plurality of potions $V_{PF}$ are emitted via the fluid discharging outlet to within the body cavity It is another object of the present invention to disclose a device as defined in any of the above, wherein the substance is selected from a group consisting of proteins; stem-cells; cells, cells secreation/secrotomes, organs, portions, extracts, and isolations thereof; macro-molecules; RNA or other genes and proteins-encoding materials; neurotransmitters; receptor antagonists; hormones; Ketamine; Baqsimi product commercially available by Lilly (US); Glucagon; substrates to treat one of the followings: anaphylaxis, Parkinson, seizures and opioid overdose; epinephrine; atropine; metoclopramide; commercially available Naloxone or Narcan products; Esketamine (Spravato); Radicava [edaravone]; Ingrezza [valbenazine]; Austedo [deutetrabenazine]; Ocrevus [ocrelizumab]; Xadago [safinamide]; Spinraza [nusinersen]; Zinbryta [daclizumab]; Nuplazid [pimavanserin]; Aristada [aripiprazole lauroxil]; Vraylar [cariprazine]; Rexulti [brexpiprazole]; Aptiom [eslicarbazepine acetate]; Vizamyl [flutemetamol F18 injection]; Brintellix [vortioxetine]; Tecfidera [dimethyl fumarate]; Dotarem [gadoterate meglumine]; Antibody mediated brain targeting drug delivery including aducanumab, gantenerumab, bapineuzumab, solanezumab, ofatumumab CD20, BIIB033, LCN2, HMGB1; insulin; oxytocin; orexin-A; leptin; benzodiazepine i.e. midazolam; perillyl alcohol; camptothecin; phytochemicals including curcumin and chrysin; nucleotides; olanzapine; risperidone; Venlafaxin; GDF-5; zonisamide; ropinirole; plant-originated and synthetically-produced terpenes and cannabinoids, including THC and CBD; valproric acid; rivastigmine; estradiol; topiramate or an equivalent preparation comprising CAS No. 97240-79-4; MFSD2 or MFSD2A or sodium-dependent lysophosphatidylcholine symporter; and any esters, salts, derivatives, mixtures, combinations thereof, with or without a carrier, liposomes, lyophilic or water-miscible solvents, surfactants, cells, cells fractions, cells secreation/secrotomes at a therapeutically effective concentration.

Another object of eth invention is to disclose a method for delivering either one or more substances within at least one body cavity, characterized by steps of providing a vial with $V_{sub}$ [ml] of the substances; the vial selected from a pierceable container, a blow-fill-seal and a form-fill-seal, further providing the vial with a fluid inlet and a fluid discharging outlet of diameter D [mm], configured for placement in proximity to the body cavity; configuring the fluid inlet by means of size and shape to interface a puncturing member, so that upon coupling to the fluid inlet, piercing of the same, thereby providing the substances in a fluid communication, via a valve, with a chamber configured to accept pressurized fluid at volume $V_{PF}$ [ml] and pressure $P_{PF}$ [barg]; the valve is commutable from a CLOSED to an OPEN CONFIGURATION within a short period of time, <500 milliseconds (dT); in the OPEN CONFIGURATION, facilitating the flow of the pressurized fluid from the chamber via the fluid inlet, thereby emitting the substances via the fluid discharging outlet to within the body cavity.

It is another object of the present invention to disclose a method as defined above, wherein the method is provided useful for the delivery of the predetermined volume $V_{sub}$ [ml] of the substance and the predetermined volume $V_{gas}$ of the pressurized gas through the orifice of diameter D [mm] in a pressure rate of $dP_{gas}/dT$ is provided; and further wherein at least one of the following is held true: the method comprises a step of providing $P_{gas}$ (or $P_{PF}$) is in a range of about 0 to about 10 barg; the method comprises a step of providing $V_{gas}$ (or $V_{PF}$) is in a range of about 1 to about 50 ml; the method comprises a step of providing $V_{sub}$ is in a range of about 0.01 to about 7 ml or 0.1 mg to 7 g; the method comprises a step of providing D is in a range of 0.2 to about 6 mm; the method comprises a step of providing the pressure rate, $$\frac{dP}{dT} \to \infty;$$

the method comprises a step of providing the pressure rate greater than about 0.001 barg/ms; the method comprises a step of providing the volume rate $dV_{sub}/dT$ is greater than about 0.0001 ml/ms; the method comprises a step of providing the volume rate $dV_{gas}/dT$ is greater than about 0.001 ml/ms; the method comprises a step of providing the predetermined period of time, $\Delta t \to 0$; and the method comprises a step of providing $\Delta T$ is in a range of about 0 to 500 milliseconds.

It is another object of the present invention to disclose a method as defined in any of the above, wherein additionally the method comprising at least one of the following steps: selecting the body orifice from a group consisting of a nasal cavity, the mouth, the throat, an ear, the vagina, the rectum, the urethra, and any combination thereof; selecting the gas from a group consisting of: air, nitrogen, oxygen, carbon dioxide, helium, neon, xenon and any combination thereof; dispensing the at least one substance, and during the step of dispensing, forming a plume of aerosol with predetermined distribution from a mixture of the predetermined volume $V_{gas}$ [ml] of the pressurized gas and the predetermined volume $V_{sub}$ [ml] entrained within it; selecting the predetermined distribution from a group consisting of: a homogeneous distribution, a heterogeneous distribution; selecting the heterogeneous distribution from a group consisting of: an arbitrary distribution, a distribution in which the density of the at least one substance within the mixture follows a predetermined pattern, and any combination thereof; selecting characteristics of the aerosol from a group consisting of: particle size, particle shape, particle distribution, and any combination thereof, are determinable from characteristics of the device selected from a group consisting of: the predetermined volume of the pressurized gas, the predetermined volume of the substance, the predetermined pressure of the pressurized gas, the predetermined orifice size, and any combination thereof; selecting the substance from a group consisting of: a gas, a liquid, a powder, a slurry, a gel, a suspension, and any combination thereof; storing at least one the substance under one of the followings: an inert atmosphere; under vacuum; and at a pressure above ambient pressure to prevent reactions during storage; characterizing a dose-response curve for brain concentration of the substance to be of substantially linear form; and providing the administration with a dose-response curve for brain concentration having a fit selected from a group consisting of logarithmic, parabolic, exponential, sigmoid, power-low, and any combination thereof; of the substance when administered nasally via the device.

It is another object of the present invention to disclose a method as defined above, wherein the post-urge substance is delivered by a device, characterized by a vial comprising $V_{sub}$ [ml] of the substances; the vial selected from a pierceable container, a blow-fill-seal and a form-fill-seal, having fluid inlet and a fluid discharging outlet of diameter D [mm], configured for placement in proximity to the body cavity; the fluid inlet configured by means of size and shape to interface in a sealable manner a puncturing member, configured to, upon coupling to the fluid inlet, piercing the same, thereby providing the substances in a fluid communication, via a valve, with a chamber configured to accept pressurized fluid at volume $V_{PF}$ [ml] and pressure $P_{PF}$ [barg]; the valve is commutable from a CLOSED to an OPEN CONFIGURATION within a short period of time, ($\Delta t$); in the OPEN CONFIGURATION, the pressurized fluid flows at a rate of FR [m/sec] from the chamber, via the fluid inlet, entrains the substances and emitted via the fluid discharging outlet to within the body cavity.

It is another object of the present invention to disclose a method as defined above, wherein the device is configured so that at least one of the following is true: the pressurized fluid flow rate (FR) is in a rang selected from a group consisting of about 10.8 m/s to about 13.8 m/s; about 13.9 m/s to about 17.1 m/s; about 17.2 m/s to 20.7 m/s; and 20.8 m/s or more;

perillyl alcohol; camptothecin; phytochemicals including curcumin and chrysin; nucleotides; olanzapine; risperidone; Venlafaxin; GDF-5; zonisamide; ropinirole; plant-originated and synthetically-produced terpenes and cannabinoids, including THC and CBD; valproric acid; rivastigmine; estradiol; topiramate or an equivalent preparation comprising CAS No. 97240-79-4; MFSD2 or MFSD2A or sodium-dependent lysophosphatidylcholine symporter; and any esters, salts, derivatives, mixtures, combinations thereof, with or without a carrier, liposomes, lyophilic or water-miscible solvents, surfactants, cells, cells fractions, cells secreation/secrotomes at a therapeutically effective concentration.

BRIEF DESCRIPTION OF THE DRAWINGS

The invention is herein described, by way of example only, with reference to the accompanying drawings, wherein:

FIGS. 1A and 1B disclose an example of the intranasal delivery device of this invention (1A) and plume thereof (1B), according to two embodiments of the invention; Sip-Nose' heterogeneous aerosol: (A) Initial spray portion has a narrow plume geometry (B) combination of the narrow plume spray portion and the wider aerosol portion (C) steady state aerosol portion with wider plume;

DETAILED DESCRIPTION OF THE PREFERRED EMBODIMENTS

Figure 2:
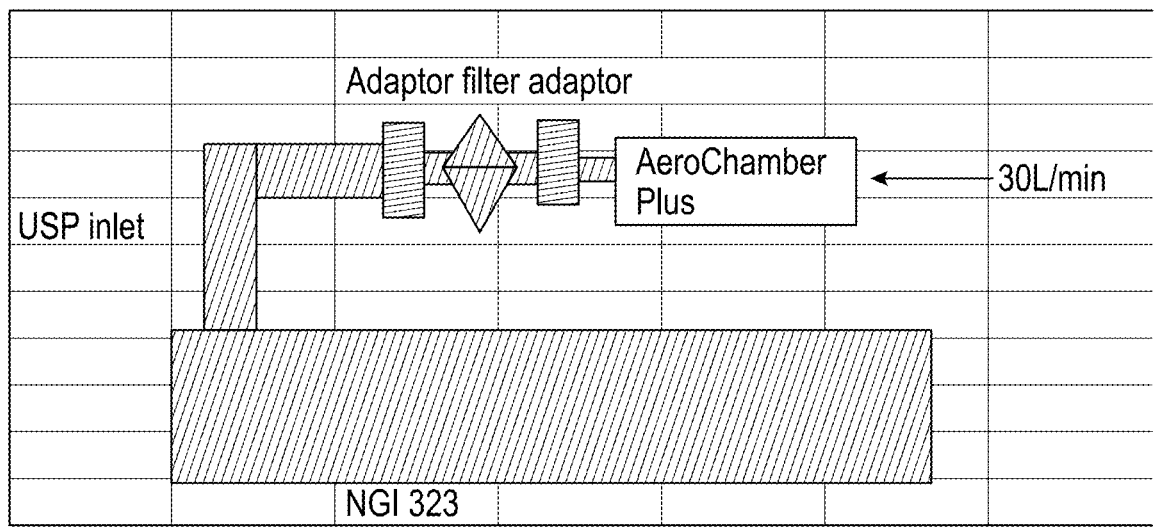
FIG. 2 is a schematic illustration of a set-up for determining a delivered dose.

This application incorporates herein by reference the contents of U.S. application Ser. No. 15/982,996 in its entirety.

The following description is provided, alongside all chapters of the present invention, so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide a device capable of improving the transfer of medicament to a predetermined desired location and to provide a device capable of improving the delivery of medicament through the tissue.

In the present invention, a combination of parameters and forces such as pressure, gas/air volume and orifice diameter and duration of the process (t) enable the formation of optimized aerosol characteristics for both improved delivery of aerosol to the target area (such as the olfactory epithelium in the nasal cavity) and enhanced absorption at that area for better delivery to a desired tissue (such as the brain).

The term 'µl' or 'ul' hereinafter refers to the unit micro liters. The term 'capsule' or 'container' hereinafter refers to a container configured to contain a flowable substance.

It should be emphasized that the term capsule can also refer to a predefined volume within the same in which a flowable substance is placed. In other words, the predefined volume is sized and shaped to enclose a predefined volume of the substance. The term 'flowable' refers hereinafter to any liquid, gas, aerosol, powder and any combination thereof.

The term 'Substance' refers hereinafter to any flowable substance; e.g., gas, liquid or powder. The piercing could be relevant to the gas container, to the drug container (upper or lower area or both), or to both.

The term 'plurality' hereinafter refers to an integer greater than or equal to one. The term 'olfactory epithelium' hereinafter refers to a specialized epithelial tissue inside the nasal cavity. The olfactory epithelium lies in the upper top portion of the nasal cavity. The term 'substance' hereinafter refers to any substance capable of flowing. Such a substance can be a granular material, including a powder; a liquid; a gel; a slurry; a suspension; and any combination thereof.

The term 'gas' refers to any fluid that can be readily compressed. Gases as used herein include, but are not limited to, air, nitrogen, oxygen, carbon dioxide, helium, neon, xenon and any combination thereof.

The term 'channel' hereinafter refers to a passageway allowing passage of a fluid through at least a portion of a mixing mechanism. The channel can be disposed within a portion of the mixing mechanism, forming a closed bore; it can be on an exterior of a portion of the mixing mechanism, forming a groove on the portion of the mixing mechanism, and any combination thereof.

The term 'fluid' refers to any substance or mixtures of substances that continually deforms (flows) under an applied shear stress, or external force. This term refers to gas, liquids, particulate or granulated solids (powders), aerosols, and any mixtures and combinations thereof.

The term 'about' refers hereinafter to a range of 25% below or above the referred value.

The term 'biologic' or 'biologic response modifier' hereinafter refers to material manufactured in or extracted from biological sources such as a genetically engineered protein derived from human genes, or a biologically effective combination of such proteins. All pressures herein are gauge pressures, relative to atmospheric pressure. Pressure units will be written herein using the standard abbreviation for "gauge', namely, "g". For example, atmospheric pressure is 0 barg and a pressure of 1 bar above atmospheric is 1 barg.

The term 'release time' refers hereinafter to the time for the drug and carrier gas to substantially completely exit the device. Typically, the release time is affected by the combination of the Volume of substance, volume of pressurized gas, pressure of pressurized gas, the orifice diameter, the activation time of the valve that reflects the time for the device to reconfigure from the ACTIVE configuration to the INACTIVE configuration or vice versa and any combination thereof.

The terms 'the device', 'the present device', 'the SipNose device' and 'SipNose' will be used interchangeably to refer to a device were the pre-aerosolized mixture of gas and substance exits the device with a significant driving force as a mixture of aerosol and pre-aerosolized material (fluid or powder). When the pre-aerosolized material hits the walls of the nasal passages, it "explodes" into a fine aerosol that is capable of being driven by the pressure deep into the nasal passages to deposit in the desired region.

The term "cannabinoid" refers hereinbelow to any of the diverse chemical compounds that act on cannabinoid receptors on cells in the brain, act on orthosteric or allosteric sites and modulate endocannabinoid activity. They include the phytocannabinoids found in cannabis, hempseed oil, other plants, and synthetic cannabinoids manufactured artificially. They include the phytocannabinoids delta-9-tetrahydrocannabinol (THC), cannabidiol (CBD), cannabinol (CBN) cannabigerol (CBG), cannabigerol (CBG), cannabichromene (CBC), cannabicyclol (CBL), canabivarol (CBV), tetrahydrocannabivarin (THCV), cannabidivarin (CBDV), cannabichromevarin (CBCV), cannabigerol monoethyl ether (CBGM), or the like; or mixtures or combinations thereof. Other botanical cannabimimetics include N-alkylamides from Echinacea and B-caryophyllene. They include mixtures of phytocannabinoids separated from the plant by extraction techniques and high purity cannabinoids obtained by purification from natural sources or via synthesis.

In all of the embodiments of the device shown hereinbelow, identical numbers refer to identical functions. All figures shown herein are illustrative and none is to scale.

The present invention teaches a device for delivering a predetermined amount of a substance, preferably comprising a medication or combination of medications, into a body orifice of a subject, the orifice comprising any of the body's natural orifices, including a nostril, the mouth, the ear, the throat, the urethra, the vagina, the rectum and any combination thereof.

In preferred embodiments of the device, the device comprises a delivery mechanism and a medicament capsule, as described hereinbelow. The device can apply a broad range of drugs and materials to the nasal cavity for local effect, deliver a broad range of drugs and materials through the nasal cavity to the systemic circulation, deliver a broad range of drugs and materials through the nasal cavity to the central nerve system (CNS) the brain, spinal cord and associated nerves, and any combination thereof.

The drugs to be applied could be, but are not limited to, pharmaceuticals, natural compounds, biologics, hormones, peptides, proteins, viruses, cells, stem cells, cells secreation/secrotomes and any combination thereof.

However, it should be emphasized that the device can be provided alone as well as in combination with a capsule.

In some cases, the capsule would be provided with a known medicament within the same and in other cases the capsule would be 'filled' with the medicament just before use.

In some embodiments of the present invention, the device operating characteristics and the substance characteristics can be jointly optimized to maximize uptake of the substance at the desired site. In preferred variants of such embodiments, uptake is further optimized by exploiting synergies between delivery characteristics generated by the device and by the formulation or composition of the delivered material In some embodiments, the substance comprises one or more agents to optimize delivery through the mucosal membrane by means of mucoadhesive agent and/or a permeability enhancer agent and/or a particulate formulation in the nanoparticle or microparticle range, and any combination thereof. In such embodiments, the combination of the device and substance enhance the delivery of the active agent to the target area (nasal epithelium and more specifically olfactory epithelium) and from there to the target tissue (for example the brain).

A non-limiting example is a composition comprising a drug to be delivered and at least one chemical permeation enhancer (CPE). In a preferred embodiment, the composition contains two or more CPEs which, by using a nasal delivery device, affect delivery of the drug in an additive manner or behave synergistically to increase the permeability of the epithelium, while providing an acceptably low level of cytotoxicity to the cells. The concentration of the one or more CPEs is selected to provide the greatest amount of overall potential (OP). Additionally, the CPEs are selected based on the treatment. CPEs that behave primarily by transcellular transport are preferred for delivering drugs into epithelial cells. CPEs that behave primarily by paracellular transport are preferred for delivering drugs through epithelial cells. Also provided herein are mucoadhesive agents that enable the extension of the exposure period of the target tissue/mucus membrane to the active agent, for the enhancement of delivery of the active agent to and through the mucous membrane.

In contrast to prior-art nasal delivery devices and technologies, the devices of the present invention can produce a fine aerosol in the nasal cavity or other desired body orifice at the target area and at the location of the target tissue instead of producing the aerosol only within the device or immediately after exit from the device. Utilizing the pressure as a driving force and the air as a carrier allows the material to be released from the nozzle as a mixture of aerosol and a pre-aerosolized state. The properties of the resultant aerosol are typically dependent on the properties of the device and of the medium into which the device is discharged. The properties of the device which affect the aerosol characteristics are the delivery pressure, the volume of the delivery gas, the characteristics of its orifice and time to activate the valve that reflects the time for the device to reconfigure from the ACTIVE configuration to the INACTIVE configuration or vice versa and any combination thereof.

In some embodiments, the aerosol properties are fairly independent of the delivered substance, while, in other embodiments, the pressure, volume, orifice characteristics, and delivered substance properties can be co-optimized.

In prior-art devices the aerosol is produced in proximity exit of the device. Typically, the aerosol comprises a wide "fan" of aerosol and a low driving force. Therefore, large droplets typically deposit very close to the exit from the device, while smaller droplets tend to quickly contact the walls of the passage, so that deposition is typically predominantly close to the delivery end of the device, with little of the substance reaching desired sites deeper in the body orifice, such as the middle and superior turbinates of the nose.

Reference is now made to FIG. 1a, disclosing a device according to one embodiment of the present invention. The BFS is separable from the rest of the device. The device comprises, inter alia, a BFS nose piece (1), a pressurized-fluid container (2), an air chamber gate (3) and an activation mechanism base (4).

It is well in the scope of the invention wherein the pressurized fluid is accommodated within container (2) for a relatively long time, e.g., by having a pre-pressurized container in a fluid connection (with a capsule (e.g., a BFS) enclosing the substance and releasing the same, or alternatively a container suitable for pressuring the fluid in situ within the container, e.g., by introducing a pump or piston mechanism that pressurizes ambient air in the container in a first step and accommodating the pressurized fluid for a relatively short time, then allowing the fluid to flow.

It is well in the scope of the invention wherein at least one of the above is provided in an intermittent manner, e.g., by train of n pulses, n is an integer equal to or greater than 2, e.g., 2, 5, 10, 30 or more. Pulses are provided by various mechanisms selected in a non-limiting manner from a series of pressurizing events (pulsating piston for example and/or a series of volume changes within the container); a series of releases of pressurized fluid, by having rapid opening and closing actions of the valve and/or applying blowable lips or reed(s) at the end of the orifice, e.g., as those provided in a mouthpiece of a wind instrument.

The pulses can be identical, e.g., same pressure, same period of time, same volume etc. Additionally, or alternatively, at least one pulse can different for at least one other pulse in e.g., pressure, time, volume, etc. It is well within the scope of the invention wherein the fingerprint of the pulses is of increasing pressure, increasing time; and/or increasing pressure decreasing time; and/or decreasing pressure same time and so on and so forth.

The device of the present invention (refers hereinafter as SipNose's IN Delivery Device) (See FIG. 1A, device) produces a fine aerosol delivered to the targeted area of the nasal cavity, the upper nasal cavity. In oppose to commercial nasal devices, the SipNose's aerosol (See FIG. 1B) is created before it exits from the device. Utilizing the pressure as a driving force and the air as a carrier allows the drug to be released from the nozzle and efficiently delivered to the target area to be absorbed by the target tissue. The plume angle is the total angle subtended by the plume. The SipNose IN Delivery Device creates a mono or bi-Modal spray pattern. If a bi-Modal spray pattern is achieved the initial spray portion has a narrow plume geometry that then develops to a wider plume geometry spray (initial portion and steady state portion). If mono-Modal spray is achieved, the plume geometry is similar to the steady state aerosol portion of the bi-Modal spray pattern.

It is another object of the present invention to disclose the device a s disclosed in any of the above, wherein at least one of the following is true: (a) The body orifice is a nasal cavity, the mouth, the throat, an ear, the vagina, the rectum, the urethra, and any combination thereof. (b) The pressurized fluid is selected from a group consisting of air, nitrogen, oxygen, carbon dioxide, helium, neon, xenon, HFC and any combination thereof (c) During dispensing of the at least one substance, a mixture of the predetermined volume $V_{gas}$ [ml] of the pressurized gas with the predetermined volume $V_{sub}$ [ml] of the substance entrained within it forms a plume of aerosol; the aerosol having a predetermined distribution, the distribution being either homogeneous or heterogeneous, the heterogeneous distribution is selected from a group consisting of: an arbitrary distribution, a distribution in which the density of the at least one substance within the mixture follows a predetermined pattern, and any combination thereof; characteristics of the aerosol selected from a group consisting of: particle size, particle shape, particle distribution, and any combination thereof, are determinable from characteristics of the device selected from a group consisting of: the predetermined volume of the pressurized gas, the predetermined volume of the substance, the predetermined pressure of the pressurized gas, the predetermined orifice size, and any combination thereof. (d) At least one the substance is selected from a group consisting of a gas, a liquid, a powder, an aerosol, a slurry, a gel, a suspension and any combination thereof. (e) At least one the substance is stored under one of the followings: an inert atmosphere; under vacuum and a pressure above ambient pressure to prevent reactions during storage. (f) A dose-response curve is substantially linear for brain concentration of the substance when administered intranasally via the device. (g) A dose-response curve for brain concentration having a fit selected from a group consisting of logarithmic, parabolic, exponential, sigmoid, power-low, and any combination thereof; of the substance when administered intranasally via the device.

It is an embodiment of the invention wherein a unit dose device for delivering a predetermined amount $M_{sub}$ of at least one substance, within at least one body cavity of a subject is utilized. The unit dose device comprises at least one predefined volume sized and shaped for containing the predetermined amount $M_{sub}$ of the at least one substance; a delivery end for placement in proximity to the body cavity, the delivery end being in fluid communication with the container; the delivery end comprises at least one orifice of diameter D; at least one valve mechanically connectable to the container, characterized by at least two configurations: (i) an active configuration in which the valve enables delivery of predetermined amount $M_{sub}$ of the substance from the container to the body cavity via the delivery end; and, (ii) an inactive configuration, in which the valve prevents delivery of the predetermined amount $M_{sub}$ of the substance from the container to the body cavity; the valve is reconfigurable from the inactive configuration to the active configuration within a predetermined period of time, dT, in response to activation of the same; and The unit dose as defined above, wherein the unit dose device has a configuration selected from a group consisting of configured to deliver a single unit dose or configured to deliver two-unit doses.

It is according to yet another embodiment of the invention wherein the unit dose device is configured to deliver the predetermined amount $M_{sub}$ of the substance and the pre-determined volume $V_{gas}$ of the pressurized gas through the orifice of diameter D in (a) pressure rate of $dP_{gas}/dT$; (b) volume rate of $dV_{gas}/dT$; and (c) amount rate of $dM_{sub}/dT$; and at least one of the following being held true: $P_{gas}$ is in a range of 0 to 10 barg; $V_{gas}$ is in a range of 1 to 50 ml; D is in a range of 0.2 to 6 mm; $dP_{gas}/dT$ is greater than 0.001 barg/ms; the amount rate $dM_{sub}/dT$ is greater than 0.0001 ml/ms or greater than 0.0001 mg/ms; the volume rate $dV_{gas}/dT$ is greater than 0.001 ml/ms; dT is in a range of 0 to 500 millisecond; and any combination thereof.

It is according to yet another embodiment of the invention wherein a fluid tight chamber configured to contain predetermined volume $V_{gas}$ of pressurized gas at a predetermined pressure, $P_{gas}$. It is according to yet another embodiment of the invention wherein the pressurized gas, once the valve is reconfigured from the inactive configuration to the active configuration, is configured to entrain the substance and deliver the same via the orifice in the delivery end.

Example 1

Treatment of pain & central nervous system is found useful by utilizing a device of the present invention, see items 1-4, FIG. 1A, for the delivery of various medicaments; e.g., treatment of chronic conditions such as Alzheimer's, Parkinson's, depression, pain, seizures, epilepsy and acute migraine, conscious sedation and sleep aids.

Example 2—Different Medicament Administered Via the Use of the Present Invention The following merely lists some of the treatment that could utilize the SipNose device: Puhakka et al. discloses that corticosteroids are anti-inflammatory agents with a wide variety of effects on several inflammatory mediators. Over the past few years, steroids have found a place in the treatment of infectious diseases. Dexamethasone is an established treatment of acute viral-induced laryngitis and *Haemophilus influenzae* type b-induced meningitis in children. Intranasal corticosteroids decrease the inflammatory reaction in the nasal cavity and shorten the duration and decrease the severity of symptoms in upper respiratory tract virus infection. Coughs and colds can be treated by utilizing a non-BFS/FFS-device for the delivery of various medicaments, such as fluticasone propionate, see Puhakka, Tuomo, et al. "The common cold: effects of intranasal fluticasone propionate treatment." *Journal of Allergy and Clinical Immunology* 101.6 (1998): 726-731.

US patent application US20090285849 discloses that an immune response to certain antigens which are otherwise weakly immunogenic can be enhanced through the use of vaccine adjuvants. Such adjuvants potentiate the immune response to specific antigens and are therefore the subject of considerable interest and study within the medical community. Cancer, allergic diseases, asthma, and chronic infections such as coronavirus, SARS-associated coronavirus, HIV, HCV, HBV, HSV, COVID-19 or coronavirus, and *H. pylori* are relevant condition in this sense to treat. Hepatitis, for example, is a systemic disease that predominantly affects the liver. The disease is typified by the initial onset of symptoms such as anorexia, nausea, vomiting, fatigue, malaise, arthralgias, myalgias, and headaches, followed by the onset of jaundice. The application further states that, in the United States, about 20% of patients with chronic hepatitis die of liver failure, and a further 5% develop hepatitis B-associated carcinoma. Vaccines, immunotherapy and antivirals can be administered by a device as defined in BFS-type device of the present invention and a non-BFS/FFS-type device, for the delivery of various medicaments, including thiosemicarbazones.

Pulmonary endothelial prostacyclin appears to be involved in the pathogenesis of chronic obstructive pulmonary disease (COPD). prostacyclin ($PGI_2$), a vasodilatory prostanoid released by pulmonary endothelial cells (ECs), is reduced in lung tissue of patients with emphysema. Furthermore, iloprost, a $PGI_2$ analog, protected against cigarette smoke extract-induced EC apoptosis. Beraprost, another prostacyclin analog, reduced emphysema formation, inflammation, and apoptosis when given as pretreatment prior to cigarette smoke in a murine model of COPD, see Lammi, Matthew R., et al. "Treatment with intranasal iloprost reduces disease manifestations in a murine model of previously established COPD." American Journal of Physiology-Lung Cellular and Molecular Physiology 310.7 (2016): L630-L638. Asthma and COPD can be treated by utilizing the SipNose of the present invention for the delivery of various medicaments, including Iloprost.

Example 3

Investigation of the Aerosol Dose Delivery Characteristics of the Sipnose Device Example 5.1 Topiramate's and Saline's Aerosol Materials & Equipment The investigations of the aerosol characteristics were performed using a Malvern Spraytec instrument and the spray pattern and plume geometry were measured using an Oxford Laser Envision system. The SipNose device was tested with Topiramate API (Manufacturer: MSN; Batch No. TI0020516, Exp. Date: April 2019), and with Saline (0.9% NaCl Teva pharmaceuticals, Lot No: K61229 Exp. Date January 2020) as a control. As the SipNose delivery systems are a single dose disposable product, each of the tests detailed in the report was done on a separate ("new") device and reflects consistency between different devices. Two different fill volumes (100 µl and 200 µl) were tested with the Saline solutions, and 30 mg dry topiramate powder was tested with devices pressurized to 5bar. The delivery system was mounted in a holder throughout the measurements to reduce movements at the time of activation. All devices were actuated manually (and not by an automated pump) to reflect potential use by users.

Delivered Dose

The determination of the delivered dose was performed to investigate dose consistency and the reproducibility of the dose released from the disposable delivery system. Theoretically, measuring the released dose by activating the device into a collecting container would be the straightforward way to do it, but aerosol evaporation makes this challenging and inconsistent. Delivered dose measurements were done by calculations based on measuring the residual amount of drug (by weight) in the device following activation. The procedure for the delivered dose determination was as follows:

1. The device parts were weighted (empty) $\{M_{cmp}\}$;
2. The device was filled with compressed air (at 5 bar);
3. The device parts were weighed to note the weight of the air in the device $\{M_{air}\}$;
4. The dose (liquid or powder drug) was inserted into the transparent nose piece (which is also the drug container) with a syringe and needle;
5. The device was weighed to note the weight of the pre-filled device with the air and drug $\{M_{air}+d\}$;
6. The dose was released into an aero-chamber;
7. The device was weighed to note the weight of the device following the activation ($M_{res}$) which reflects the device weigh without air (100% release of discharge air in each activation) and with the residual drug that was not released; and
8. The released dose was calculated by subtracting the weight of the device after release ($M_{res}$) from the weight of the device before release ($M_{air}+d$) minus the air weight.

The set-up for determination of the delivered dose determination is schematically illustrated in FIG. 2. A Next Generation Impactor (NGI) fitted with a USP inlet was used for generation a stable 30 lpm air flow. The dose from the delivery device was released into an AeroChamber Plus and a filter was connected prior to the USP inlet. Acceptance criteria for delivered dose measurements for the SipNose delivery system and in accordance with the guidelines is defined as: verification of device spray weight delivery for potential drug products, with acceptance criteria of the spray weight of the individual sprays to within 15% of the target weight and their mean weight to within 10% of the target weight.

Laser Diffraction

The investigation of the droplet size characteristics was performed using a Malvern Spraytec instrument equipped with software version 3.30. The instrument was used in a rapid collection mode using a dedicated SOP Stare device SOP1.ssop. The investigations were done at a distance of 3 cm from the laser beam and 6 cm from the collecting lens following the guideline recommendations for measurements to be performed within a range of 2 to 7 cm from the orifice. The instrument is verified once a year and the latest verification was performed May 22, 2018 by Malvern Sweden.

All investigations were done in repeats of 5. The devices were tested at 5 bar. Relative Humidity (RH) and temperature were recorded once during each of the experimental days. RH varied between 46% and 67% and the temperature was between 23 degrees C. and 24 degrees C. The results from the measurements are presented as the mean of the droplet size distribution at the point where the aerosol enters the laser beam and triggers the data collection, which corresponds to the time point where 1% obscuration of the laser beam occurs, to the time point where the obscuration once again falls to 1% obscuration, i.e. when almost all aerosol is cleared from the laser beam detection area.

Sample placement: horizontally in front of the laser beam at a distance of 3 cm from the beam and 6 cm from the lens. Laser trigger condition: sample collection triggered when transmission drops 1% from 100%; Beam width: 1 cm. Acceptance criteria for laser diffraction measurements for the SipNose delivery system is defined as: Mono or bi-Modal spray pattern with an initial peak (higher peak) with DV50 higher than 100 µm and a steady state portion (lower peak) with DV50 lower than 100 µm (between 20-100 µm). When mono-modal, only the lower peak is present. The overall D50 calculated for each aerosol release shows droplet size averages between 50 and 250 µm. Also, less than 10% of the droplets in the overall D10 calculations are below 10 µm.

Spray Pattern and Plume Geometry

The investigation of the aerosol plume geometry and spray pattern characteristics were performed using an Oxford Laser Envision system (300 W fishtail IR laser and camera) equipped with camera software version PFV 0.3541 and Envision Patternate software version 1.3.1 using calibration file "Calib_stare_C1S000100" using a NIST calibrated 11 cm×11 cm grid. Calculations were done for both spray pattern and plume geometry including 95% in both investigations, i.e. 97.5% on each side of the total overlay droplets visible in the spray. The laser was mounted so that the IR fishtail was spread vertically which allowed for the spray pattern/plume geometry to be captured vertically as the device was mounted in a horizontal position. All spray pattern investigations were done at a distance of 6 cm from the exit of the nozzle i.e. the exit of the nozzle was positioned 6 cm from laser fishtail. All plume geometry measurements were done in such a way that the tip of the nozzle was visible in the picture. This allowed the origin of the aerosol spray to be defined for the calculation of the spray angle. For plume geometry, the angle and width at 6 cm was also calculated by the software. For the spray pattern, the software calculated the smallest and largest pattern diameter at 6 cm, where the point of origin was chosen to be the device nozzle, the point where the aerosol leaves the device. The oblongation index was then calculated in Excel (largest pattern diameter divided by smallest pattern diameter). Three to four disposable devices with formulation were activated and measured for each drug volume. The acceptance criteria, defined by SipNose, for spray pattern and plume geometry of the total overlay droplets visual in the spray measured for the SipNose delivery system in accordance to guidelines, are defined as:

Aerosol of overall (total) aerosol pattern an ellipsoid of relatively uniform density, where the short axis and the long axis are no longer than 4 cm and the ratio between the longest and the shortest axes (Oblongation) is in the range of 1.5±1; and/or Plume angle of overall (total) aerosol of 35°±10 is accepted for aerosol release when measured from the device nozzle as the origin, and the width of the plume at 6 cm from the nozzle should be at the range of 3±1.5.

More specifically, it is noted by the inventors of the present invention that the bi-modal spray pattern, comprising a first pattern and a second pattern; further wherein the first pattern is characterized by (a) Plume angle is in the range of 5°±4°; (b) width of plume at 6 cm from the nozzle is in the range of 4 mm±3 mm; and, the second pattern is characterized by (a) Plume angle is in the range of 35°±10; (b) width of plume at 6 cm from the nozzle is in the range of 30±10 mm; further wherein the mean particle's size in the first pattern is larger than the mean particle's size in the second pattern.

Figure 3:
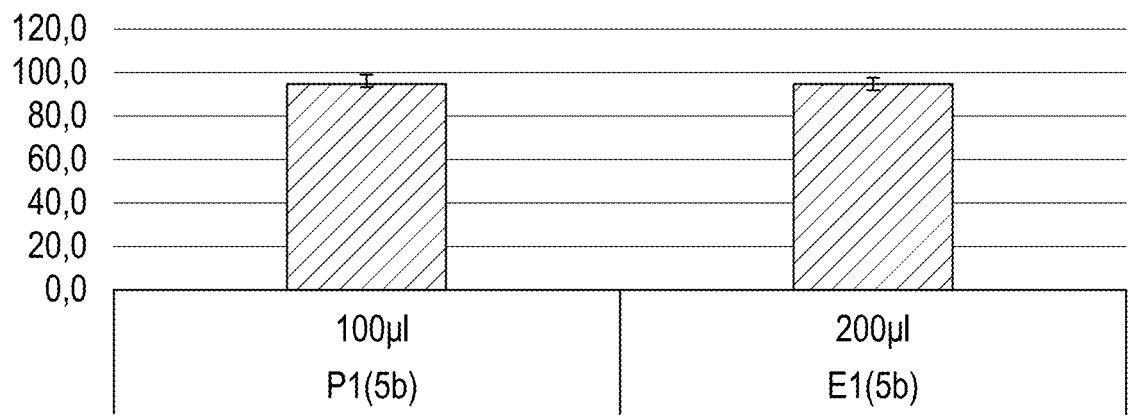
FIG. 3 depicts delivered doses of saline.

The results shown below contain both aerosol characteristics and the delivered dose for saline (100 μl and 200 μl) and topiramate dry powder (30 mg) with pressurized devices with 5bars. Reference is now made to FIG. 3 illustrating that all saline dose (100 μl and 200 μl) was delivered.

Saline—Delivered Dose Determination

The mean values and standard deviations are presented in Table 1 and in FIG. 3. All individual data are presented in Table 2. Both 100 μl dose and 200 μl dose were released from a device pressurized to 5 bars.

TABLE 1

Mean Values for residue volumes (%) following aerosol release. Delivered mass in % of loaded mass

| Drug Name | Sample (X bar) | Volume μl | Mean | SD | RSD % |
|---|---|---|---|---|---|
| Saline | P1(5b) | 1000 μl | 96.1 | 3.2 | 3.3 |
|  | E1(5b) | 200 μl | 94.3 | 3.0 | 3.2 |

TABLE 2

Individual Values for saline at 5 bar.

| Sample (x bar) | # | Drug Name | Volume | Empty- before g | with Air g | With Drug g | After dosing g |
|---|---|---|---|---|---|---|---|
| P1(5b) | 1 | Saline | 100 | 8.5492 | 8.5651 | 8.6621 | 8.5504 |
|  | 2 | Saline | 100 | 8.5254 | 8.54 | 8.643 | 8.527 |
|  | 3 | Saline | 100 | 8.6404 | 8.6559 | 8.759 | 8.6429 |
|  | 4 | Saline | 100 | 8.55 | 8.5652 | 8.6657 | 8.5525 |
|  | 5 | Saline | 100 | 8.5228 | 8.5386 | 8.6402 | 8.532 |
|  | 6 | Saline | 100 | 8.5382 | 8.553 | 8.6585 | 8.545 |
| E1(5b) | 1 | Saline | 200 | 8.5455 | 8.56 | 8.7589 | 8.5523 |
|  | 2 | Saline | 200 | 8.5267 | 8.542 | 8.7474 | 8.533 |
|  | 3 | Saline | 200 | 8.534 | 8.549 | 8.754 | 8.556 |
|  | 4 | Saline | 200 | 8.5078 | 8.523 | 8.7302 | 8.524 |
|  | 5 | Saline | 200 | 8.5139 | 8.5293 | 8.7378 | 8.522 |
|  | 6 | Saline | 200 | 8.5242 | 8.539 | 8.743 | 8.5344 |

| Sample (x bar) | Air loaded mg | Drug Loaded mg | Drug residue mg | drug released mg | Delivered mass % of loaded | Mean | SD | RSD % |
|---|---|---|---|---|---|---|---|---|
| P1(5b) | 15.9 | 97.0 | 1.2 | 95.8 | 98.8 | 96.1 | 3.2 | 3.3 |
|  | 14.6 | 103.0 | 1.6 | 101.4 | 98.4 |  |  |  |
|  | 15.5 | 103.1 | 2.5 | 100.6 | 97.6 |  |  |  |
|  | 15.2 | 100.5 | 2.5 | 98 | 97.5 |  |  |  |
|  | 15.8 | 101.6 | 9.2 | 92.4 | 90.9 |  |  |  |
|  | 14.8 | 105.5 | 6.8 | 98.7 | 93.6 |  |  |  |
| E1(5b) | 14.5 | 198.9 | 6.8 | 192.1 | 96.6 | 94.3 | 3.0 | 3.2 |
|  | 15.3 | 205.4 | 6.3 | 199.1 | 96.9 |  |  |  |
|  | 15.0 | 205.0 | 22.0 | 183 | 89.3 |  |  |  |

TABLE 2-continued

| Individual Values for saline at 5 bar. | | | | |
|---|---|---|---|---|
| 15.2 | 207.2 | 16.2 | 191 | 92.2 |
| 15.4 | 208.5 | 8.1 | 200.4 | 96.1 |
| 14.8 | 204.0 | 10.2 | 193.8 | 95.0 |

The mean results for dose release for Saline formulation is 97 μl±3.3 for 100 μl intended dose and 193.25 μl±6.3 for 200 μl intended dose. For both intended doses (100 and 200 μl), the released dose results pass the acceptance criterion (less than 10% of target weight not delivered).

Droplet Size Determination by Malvern Spraytec

The droplet size distribution values for the Malvern Spraytec measurements are outlined in Table 3 below and typical Graphs are seen in FIGS. 4 to 7.

TABLE 3

| Individual results for Malvern Spraytec | | | | | |
|---|---|---|---|---|---|
| Run | Label | Volume (ul) | Pressure (Bar) | Average Dv(50) (um) | Average Dv(10) (um) | Actuation time (ms) |
| 1 | Saline E1 | 200 | 5 | 45.9 | 15.3 | 54 |
| 2 | Saline E1 | 200 | 5 | 78.6 | 18.1 | 60 |
| 3 | Saline E1 | 200 | 5 | 64.8 | 16.6 | 49 |
| 4 | Saline E1 | 200 | 5 | 61.4 | 16.7 | 69 |
| 5 | Saline E1 | 200 | 5 | 60 | 14.8 | 50 |
| 6 | Saline E1 | 200 | 5 | 49.8 | 16.4 | 68 |
| 1 | Saline P1 | 100 | 5 | 86.7 | 23.4 | 54 |
| 2 | Saline P1 | 100 | 5 | 76.3 | 18.5 | 38 |
| 3 | Saline P1 | 100 | 5 | 75.2 | 19.7 | 54 |
| 4 | Saline P1 | 100 | 5 | 125 | 22.5 | 49 |
| 5 | Saline P1 | 100 | 5 | 86.3 | 20 | 45 |
| 6 | Saline P1 | 100 | 5 | 48.8 | 13.7 | 50 |

| Run | Mean Dv(50) (um) | SD | Mean Actuation time(ms) | SD | Mean Dv(10) (um) | SD |
|---|---|---|---|---|---|---|
| 1 | 60.08 | 11.61 | 58.33 | 8.78 | 16.32 | 1.16 |
| 2 | | | | | | |
| 3 | | | | | | |
| 4 | | | | | | |
| 5 | | | | | | |
| 6 | | | | | | |
| 1 | 83.05 | 24.75 | 48.33 | 6.09 | 19.63 | 3.44 |
| 2 | | | | | | |
| 3 | | | | | | |
| 4 | | | | | | |
| 5 | | | | | | |
| 6 | | | | | | |

Figure 4:
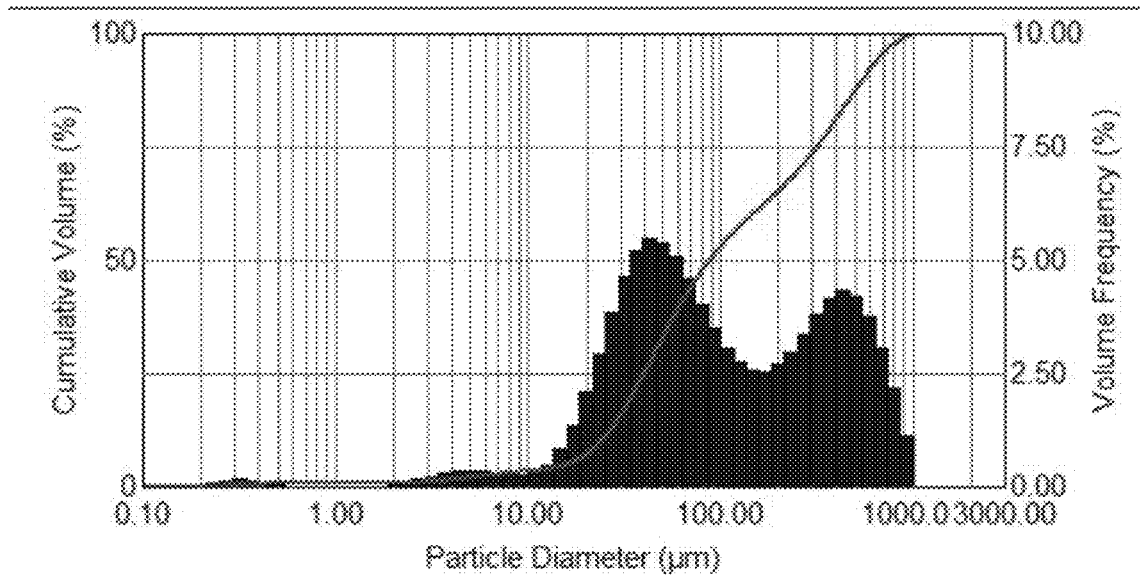
FIGS. 4-39 depict the results of topiramate, saline and midazolam spraying and the plume thereof provided by a device and methods according to an embodiment of the invention.
Figure 5:
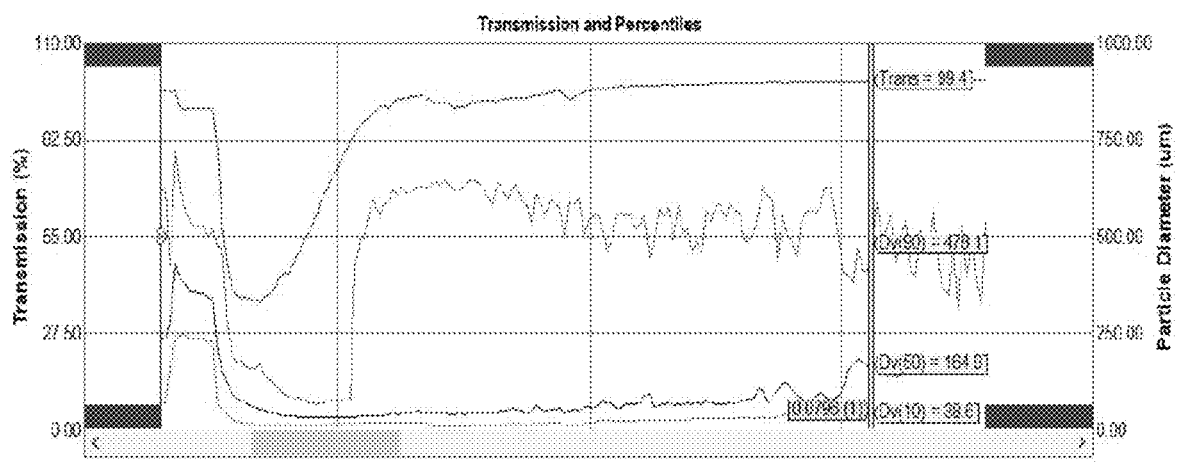
Figure 6:
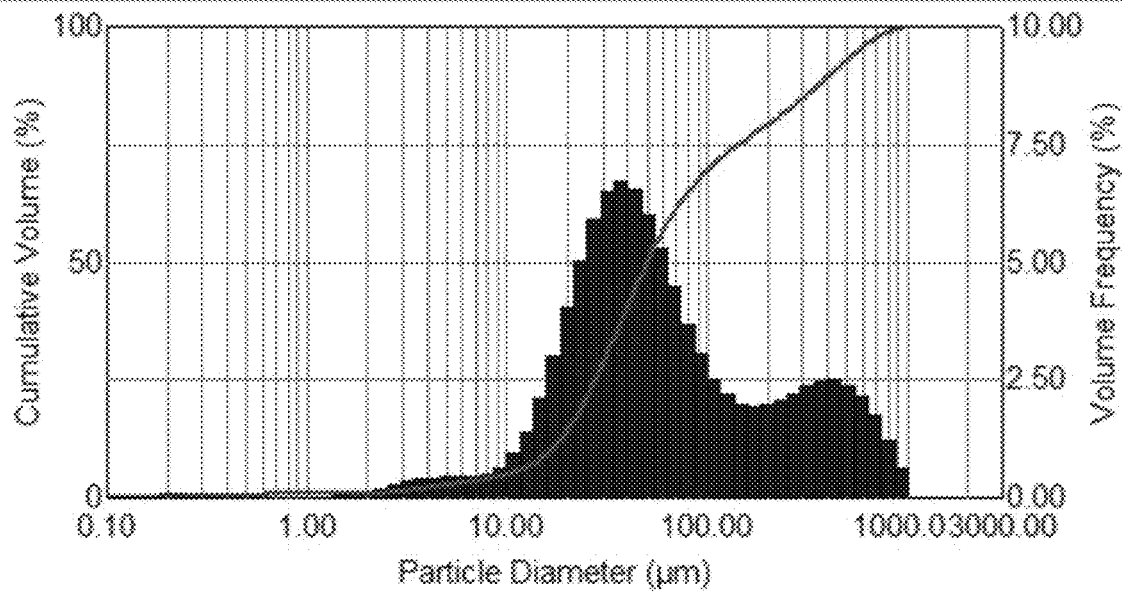
Figure 7:
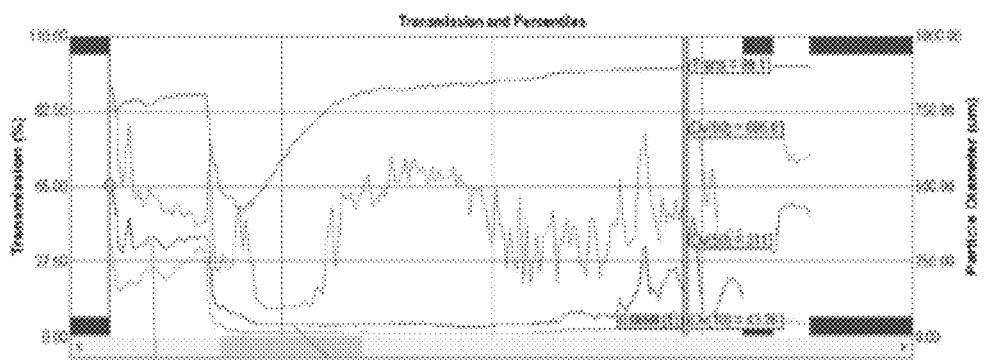

FIG. 4 shows, for Saline, an example of mean droplet size distribution for 100 μl fill volume (run 1). FIG. 5 shows, for Saline, an example of Dv(10), Dv(50) and Dv(90) vs. time for 100 μl fill volume (run 5). FIG. 6 shows, for Saline, an example of mean droplet size distribution for 200 μl fill volume (run 1). FIG. 7 shows, for Saline, an example of Dv(10), Dv(50) and Dv(90) vs. time for 200 μl fill volume (run 1).

The particle size distribution for both fill volumes shows a bimodal behavior with DV50 values of one peak above 100 μm and of the other below 100 μm, as seen in both 100 μl and 200 μl doses (FIG. 4 and FIG. 6). In the time sequenced distributions, there is an initial stable part with a higher transmission around 90 to 95% that is shorter for the 100 μl Saline fill volume than for the 200 μl Saline fill volume. Following this initial stable part is a time period where the transmission drops markedly and then again increases up to 99%. The Dv(50) value of the 100 μl Saline fill volume was found to be (60.1±11.6) and, for the 200 μl fill volume, it was found to be (83.0±24.7), while the Dv(10) value for the 100 μl Saline fill volume was found to be 19.6±3.4 and, for the 200 μl fill volume, it was found to be 16.3±1.2; both pass the acceptance criteria. In general, it is noted by the inventors of the present invention that the bi-modal spray pattern, comprising a first pattern and a second pattern; further wherein the first pattern is characterized by (a) Plume angle is in the range of 5°±4°; (b) width of plume at 6 cm from the nozzle is in the range of 4 mm±3 mm; and, the second pattern is characterized by (a) Plume angle is in the range of 35°±10; (b) width of plume at 6 cm from the nozzle is in the range of 30±10 mm; further wherein the mean particle's size in the first pattern is larger than the mean particle's size in the second pattern.

Spray Pattern and Plume Geometry by Oxford Laser Envision

TABLE 4

| Oxford Laser spray pattern results for saline Spray Patten | | | | |
|---|---|---|---|---|
| Run | Label | Volume (ul) | Pressure (Bar) | Short axis (cm) |
| 1 | Saline E1 | 200 | 5 | 2.21 |
| 2 | Saline E1 | 200 | 5 | 2.19 |
| 3 | Saline E1 | 200 | 5 | 2.16 |
| 4 | Saline E1 | 200 | 5 | 1.99 |
| 1 | Saline P1 | 100 | 5 | 2.47 |
| 2 | Saline P1 | 100 | 5 | 2.28 |
| 3 | Saline P1 | 100 | 5 | 2.36 |
| 4 | Saline P1 | 100 | 5 | 2.06 |

| Run | Long axis (cm) | Oblongation | Mean | SD | SD % |
|---|---|---|---|---|---|
| 1 | 3.33 | 1.51 | 1.51 | 0.050 | 3.28 |
| 2 | 3.39 | 1.55 | | | |
| 3 | 3.34 | 1.55 | | | |
| 4 | 2.87 | 1.44 | | | |
| 1 | 3.51 | 1.42 | 1.52 | 0.171 | 11.22 |
| 2 | 3.36 | 1.47 | | | |
| 3 | 3.33 | 1.41 | | | |
| 4 | 3.65 | 1.77 | | | |

Figure 8:
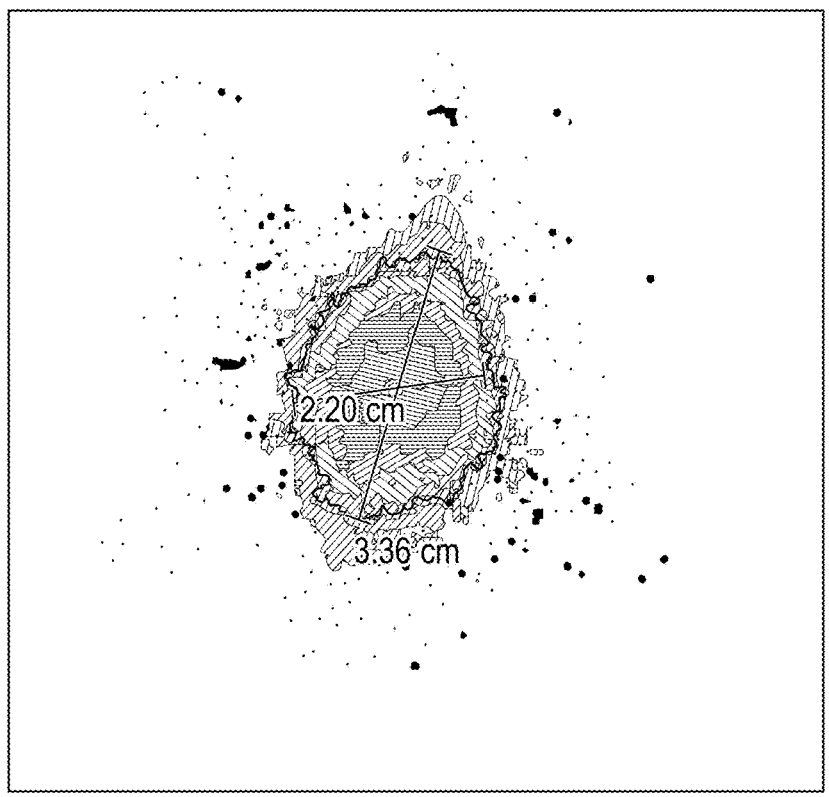
Figure 9:
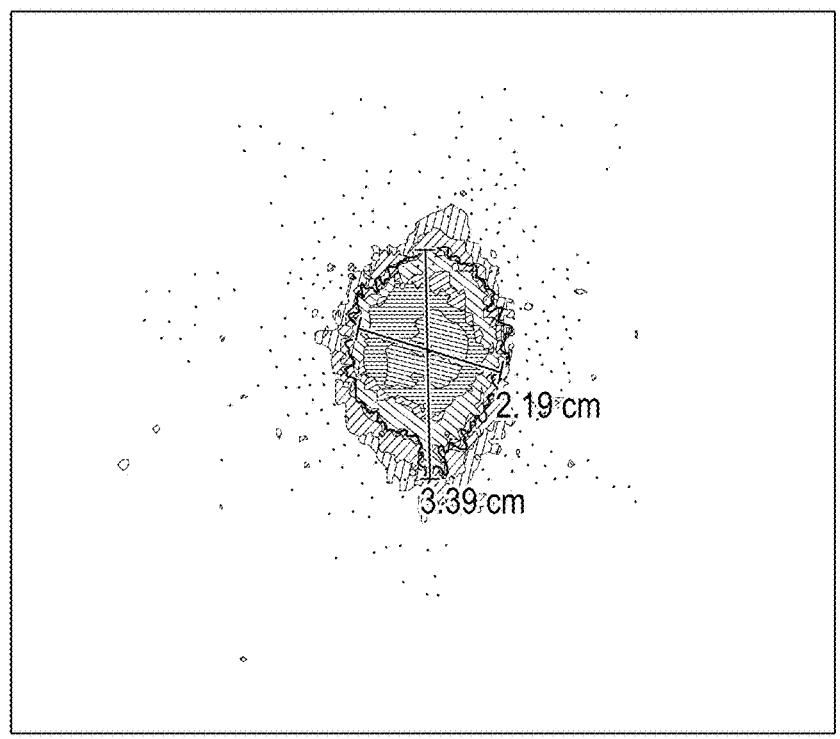

FIG. 8 discloses, for Saline, an example of the spray pattern results for 100 μl (run 2). FIG. 9 discloses, for Saline, an example of the spray pattern results for 200 μl (run 2)

Plume Geometry

TABLE 5

| Oxford Laser plume geometry results for saline Plume Geometry | | | | | |
|---|---|---|---|---|---|
| Run | Label | Volume (ul) | Pressure (Bar) | Angle (Deg) | Width (at 6 cm) |
| 1 | Saline E1 | 200 | 5 | 38.4 | 2.59 |
| 2 | Saline E1 | 200 | 5 | 36.4 | 2.43 |
| 3 | Saline E1 | 200 | 5 | 38.8 | 2.39 |
| 1 | Saline P1 | 100 | 5 | 41.8 | 2.85 |
| 2 | Saline P1 | 100 | 5 | 44.4 | 2.86 |
| 3 | Saline P1 | 200 | 5 | 35.9 | 2.54 |

TABLE 5-continued

Oxford Laser plume geometry results for saline Plume Geometry

| Run | Volume | Angle Mean | SD | SD % | Width Mean | SD | SD % |
|---|---|---|---|---|---|---|---|
| 1-3 | 200 | 37.87 | 1.29 | 3.40 | 2.49 | 0.14 | 5.68 |
| 1-3 | 100 | 40.70 | 4.36 | 10.70 | 2.75 | 0.18 | 6.62 |

Figure 10:
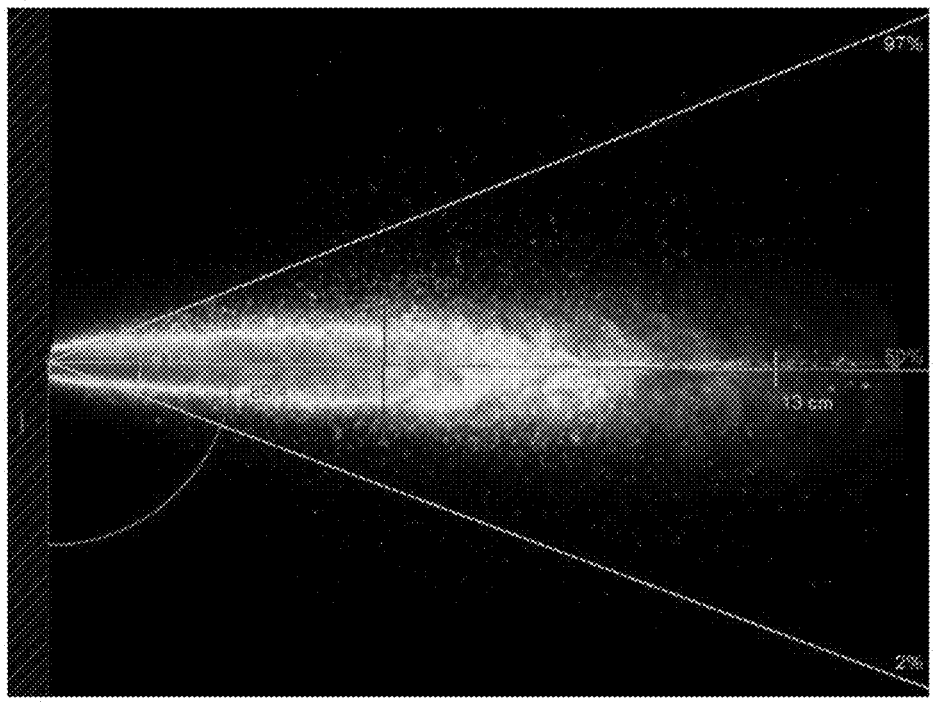
Figure 11:
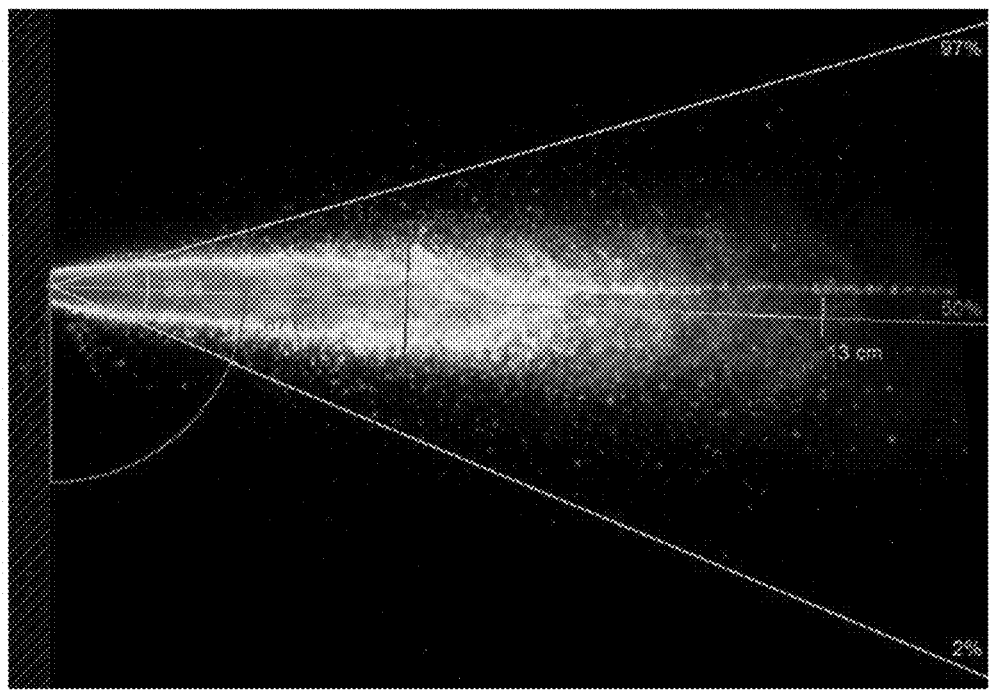

FIG. 10 discloses, for Saline, an example of the Spray Pattern results for 100 μl saline (run 1). FIG. 11 discloses, for Saline, an example of the Spray Pattern results for 200 μl saline (run 1). The overall (total) spray pattern oblongation indexes for the saline 100 μl and 200 μl are 1.52±0.17 and 1.51±0.015 respectively and thus pass the acceptance criteria. The overall (total) plume geometry angle is 40.7±4.36 degrees for the 100 μl fill volume and 37.87±1.29 degrees for the 200 μl fill volume, with width at 6 cm from the nozzle of 2.49±0.14 cm and 2.75±0.18 cm; thus, they pass all acceptance criteria.

Figure 12:
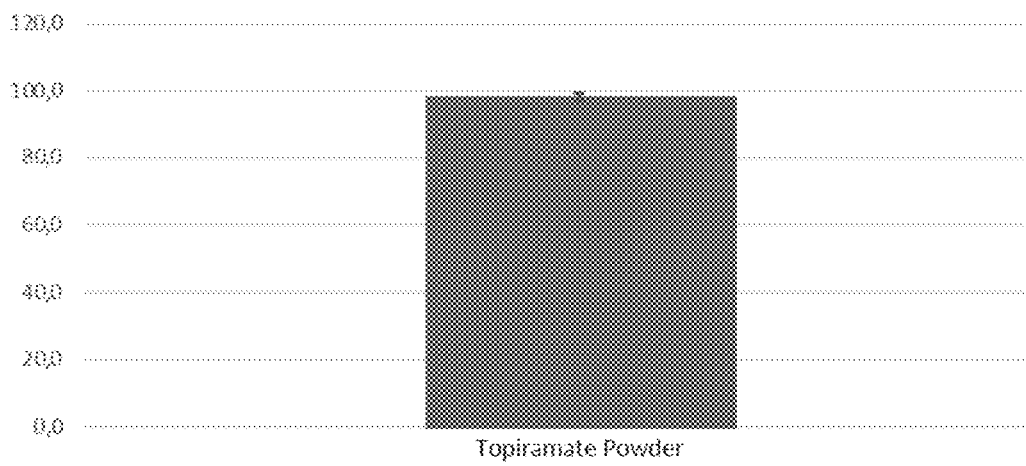

Example 5.2 Aerosol Created from Topiramate Dry Powder Investigation of the Aerosol when Topiramate Dose is Delivered—Characteristics for the Sipnose Nasal Delivery Device The mean values and standard deviations of released dose following activation of SipNose devices loaded with the topiramate powder (n=6), are presented Table 6 and in FIG. 12. All individual data are presented in Table 7.

TABLE 6

Mean Values of the delivered mass in %.

| Drug Name | Sample (X bar) | Weight mg | % Mean | SD | RSD % |
|---|---|---|---|---|---|
| Topiramate Powder | G1(5b) | 30 | 98.3 | 1.5 | 1.5 |

FIG. 12 discloses a plot of mean values of released mass in % for topiramate. As can be seen almost 100% topiramate was delivered.

TABLE 7

Individual topiramate values for the 5 bars investigation.

| Sample (x bar) | # | Drug Name | Weight | Empty-before g | with Air g | With Drug g | After dosing g |
|---|---|---|---|---|---|---|---|
| G1(5b) | 1 | Topiramate | 30 mg | 8.5167 | 8.532 | 8.5613 | 8.5167 |
|  | 2 | Powder | 30 mg | 8.5174 | 8.532 | 8.561 | 8.5175 |
|  | 3 |  | 30 mg | 8.5 | 8.516 | 8.5473 | 8.501 |
|  | 4 |  | 30 mg | 8.5216 | 8.536 | 8.569 | 8.522 |
|  | 5 |  | 30 mg | 8.5259 | 8.542 | 8.573 | 8.527 |
|  | 6 |  | 30 mg | 8.526 | 8.5415 | 8.5741 | 8.5266 |

| # | Air loaded mg | Drug Loaded mg | Drug residue mg | drug released mg | Delivered mass % of loaded | Mean | SD | RSD % |
|---|---|---|---|---|---|---|---|---|
| 1 | 15.3 | 29.3 | 0.0 | 29.3 | 100.0 | 98.3 | 1.5 | 1.5 |
| 2 | 14.6 | 29.0 | 0.1 | 28.9 | 99.7 |  |  |  |
| 3 | 16.0 | 31.3 | 1.0 | 30.3 | 96.8 |  |  |  |
| 4 | 14.4 | 33.0 | 0.4 | 32.6 | 98.8 |  |  |  |
| 5 | 16.1 | 31.0 | 1.1 | 29.9 | 96.5 |  |  |  |
| 6 | 15.5 | 32.6 | 0.6 | 32 | 98.2 |  |  |  |

The mean results for dose release for topiramate dry powder formulation is 30.5±1.49 for the 30 mg intended dose under a pressure of 5 bars. Released dose results pass the acceptance criteria (losses less than 10% of target weight). Droplet size determination by Malvern Spraytec

TABLE 8

Individual results for Malvern Spraytec

| Run | Label | Weight mg | Pressure (Bar) | Average Dv(50) (um) | Average Dv(10) (um) | Actuation time(ms) |
|---|---|---|---|---|---|---|
| 1 | Topi G1 | 30 | 5 | 42.3 | 12 | 24 |
| 2 | Topi G1 | 30 | 5 | 124.7 | 13.4 | 30 |
| 3 | Topi G1 | 30 | 5 | 116.4 | 12.4 | 29 |
| 4 | Topi G1 | 30 | 5 | 132.5 | 13.6 | 37 |
| 5 | Topi G1 | 30 | 5 | 79.2 | 12.3 | 20 |

| Run | Mean Dv(50) (um) | SD | Mean Actuation time(ms) | SD | Mean Dv(10) (um) | SD |
|---|---|---|---|---|---|---|
| 1 | 99.02 | 37.72 | 28.00 | 6.44 | 12.74 | 0.71 |
| 2 |  |  |  |  |  |  |
| 3 |  |  |  |  |  |  |
| 4 |  |  |  |  |  |  |
| 5 |  |  |  |  |  |  |

Figure 13:
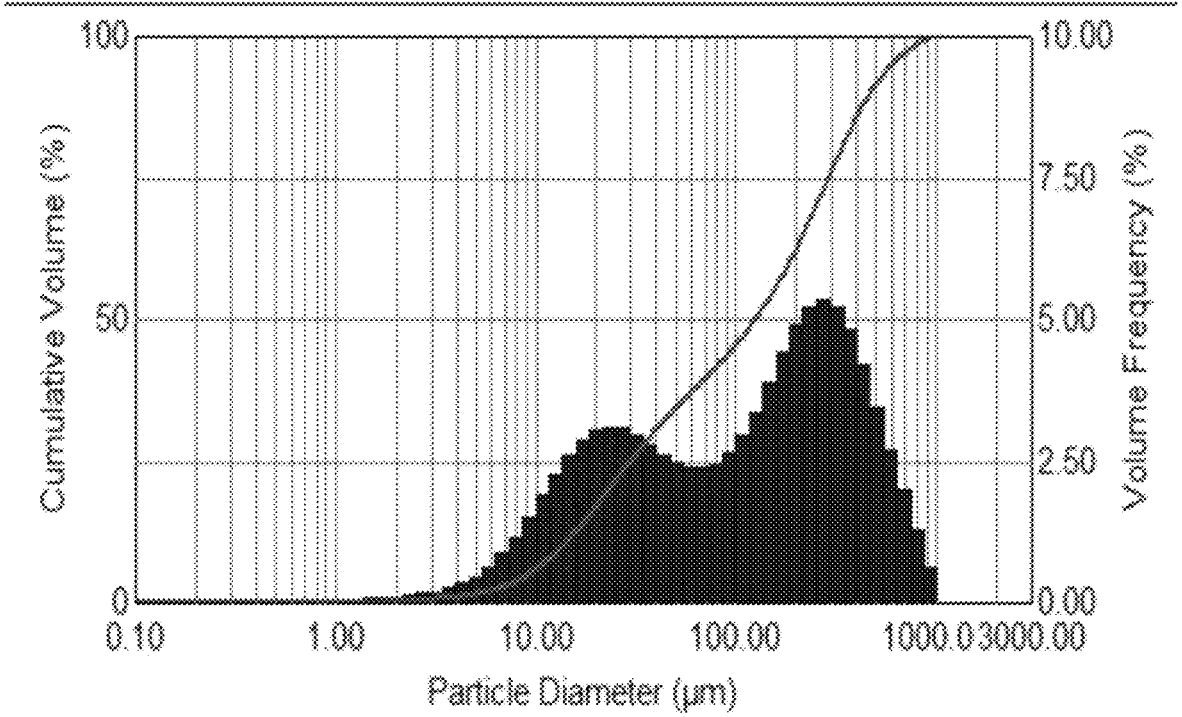
Figure 14:
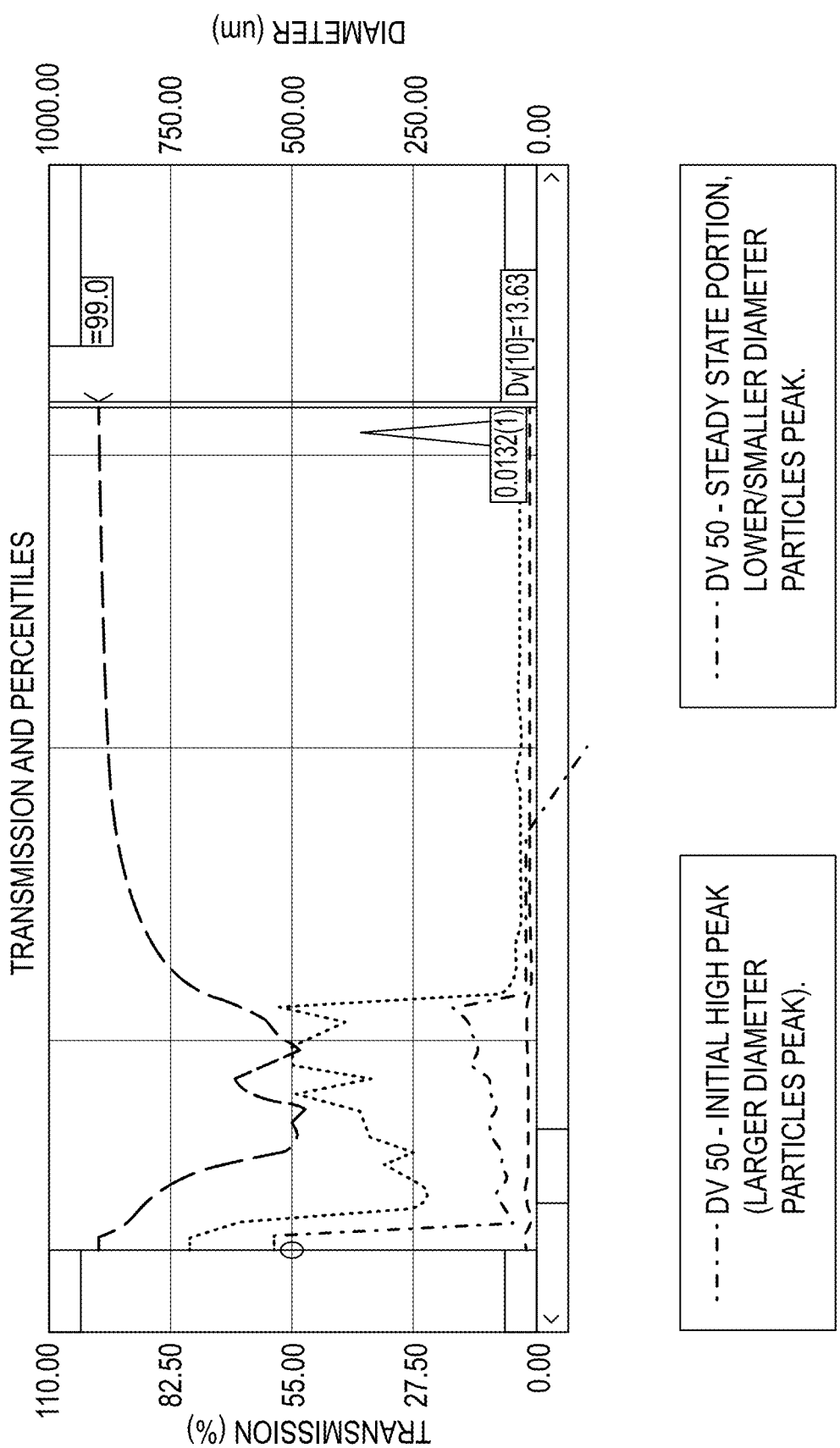

FIG. 13 shows, for topiramate, an example of mean droplet size distribution for a 30 mg fill volume (run 5, 5 Bar). FIG. 14 shows, for topiramate, an example of Dv(10), Dv(50) and Dv(90) vs. time for a 30 mg dry powder (run 1, 5 Bar).

The particle size distributions for a 30 mg topiramate dose show a bimodal behavior similar to that shown in the liquid formulations, with one peak above 100 μm and one below 100 μm. The DV(50) value (indicated by an arrow in FIG. 14 and by original text stating "blue line") for the 30 mg topiramate (99.02±37.7) and the DV(10) value of 12.74±0.71) both pass the acceptance criteria for particle size distribution for the SipNose delivery system.

Spray Pattern and Plume Geometry as Measured by the Oxford Laser Envision

TABLE 9

Oxford Laser spray pattern results for topiramate.

Spray Pattern

| Run | Label | Weight (mg) | Pressure (Bar) | Short axis (cm) | Long axis (cm) | Oblongation | Mean | SD | SD % |
|---|---|---|---|---|---|---|---|---|---|
| 1 | Topi G1 | 30 | 5 | 2.48 | 3.64 | 1.47 | 1.48 | 0.128 | 8.64 |
| 2 | Topi G1 | 30 | 5 | 2.72 | 3.79 | 1.39 | | | |
| 3 | Topi G1 | 30 | 5 | 2.28 | 3.78 | 1.66 | | | |
| 4 | Topi G1 | 30 | 5 | 2.46 | 3.4 | 1.38 | | | |

Comment: no weigh data present

Figure 15:
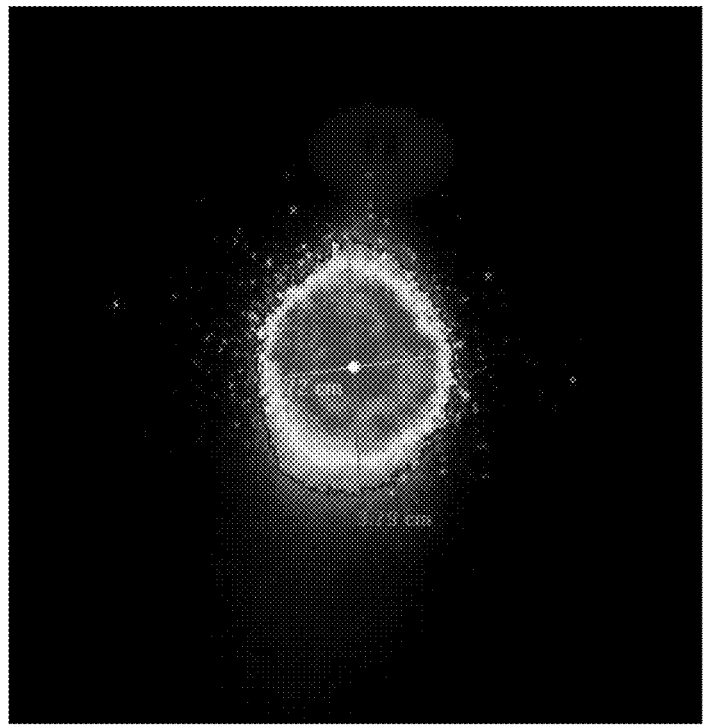
Figure 16:
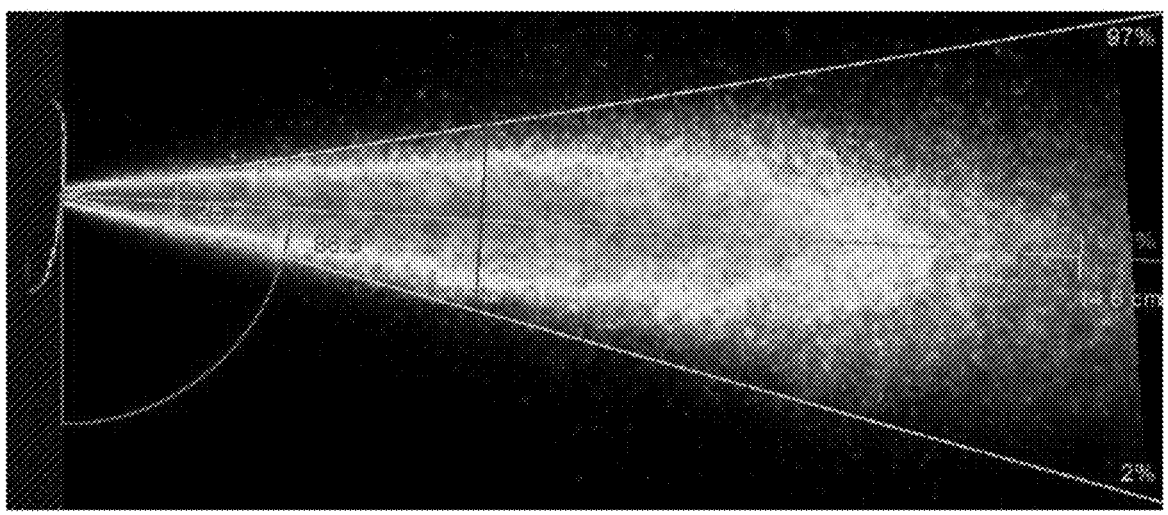

FIGS. 15-16 show, for topiramate, an example of the spray pattern results for a 30 mg fill (run 2).

Plume Geometry

TABLE 10

Oxford Laser plume geometry results for topiramate
Plume Geometry

| Run | Label | Weigt (mg) | Pressure (Bar) | Angle (Deg) | Width (at 6 cm) |
|---|---|---|---|---|---|
| 1 | Topi G1 | 31.25 | 5 | 25.1 | 2.52 |
| 2 | Topi G1 | 31.39 | 5 | 25.2 | 2.52 |
| 3 | Topi G1 | 29.21 | 5 | 26.1 | 2.78 |
| 4 | Topi G1 | 30.46 | 5 | 25.8 | 2.84 |

| | Angle | | | Width | | |
|---|---|---|---|---|---|---|
| Run | Mean | SD | SD % | Mean | SD | SD % |
| 1 | 25.55 | 0.48 | 1.88 | 2.67 | 0.17 | 6.35 |
| 2 | | | | | | |
| 3 | | | | | | |
| 4 | | | | | | |

The plume geometry results for topiramate: FIG. 16 shows, for topiramate, an example of the plume geometry results for a 30 mg fill (run 2). The spray pattern oblongation index for the 30 mg topiramate powder was, on average, 1.48±0.13. Thus, this passes the acceptance criterion. The plume geometry angle mean values has a mean of 25.5±0.48 degrees for the 30 mg dose, with a width of 2.7±0.17 cm measured at a distance of 6 cm from the device orifice, thus these also pass the acceptance criteria.

Example 5.2 Aerosol Created from Midasolam
Investigation of the Aerosol when Midazolam Dose is Delivered—Characteristics for the Sipnose Nasal Delivery Device Materials and Equipment
As in Example 5.2
Results The results below, containing both aerosol characteristics and delivered dose for saline and midazolam with the specified drug volumes (100 μl and 200 μl for saline and 200 μl-800 μl formidazolam) and specified pressures (5 and 6 bars) as defined.

Saline—Delivered Dose Determination

Figure 17:
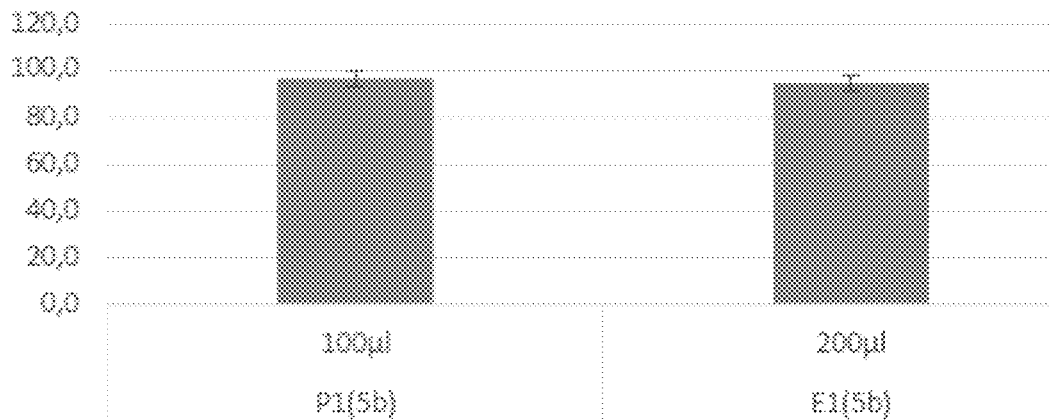

The mean values and standard deviations are presented in Table 11 and in FIG. 17. All individual data are presented in Table 11. Both the 100 μl dose and 200 μl dose were released using a pressurized device of 5 bar.

TABLE 11

Mean Values for delivered mass (%) following aerosol release.
Delivered mass in % of loaded mass

| Drug Name | Sample (X bar) | Volume μl | Mean | SD | RSD % |
|---|---|---|---|---|---|
| Saline | P1(5b) | 100 μl | 96.1 | 3.2 | 3.3 |
| | E1(5b) | 200 μl | 94.3 | 3.0 | 3.2 |

FIG. 17 shows a plot of mean values of released mass in % for saline. As illustrated, almost 100% was delivered.

TABLE 12

Individual values for saline at 5 bars.

| Sample (bar) | # | Drug Name | Volume (ml) | Empty - before (g) | With Air (g) | With Drug (g) | After Dosing (g) |
|---|---|---|---|---|---|---|---|
| P1 (5) | 1 | Saline | 100 | 8.5492 | 8.5651 | 8.6621 | 8.5504 |
| | 2 | Saline | 100 | 8.5254 | 8.54 | 8.643 | 8.527 |
| | 3 | Saline | 100 | 8.6404 | 8.6559 | 8.759 | 8.6429 |
| | 4 | Saline | 100 | 8.55 | 8.5652 | 8.6657 | 8.5525 |
| | 5 | Saline | 100 | 8.5288 | 8.5386 | 8.6402 | 8.532 |
| | 6 | Saline | 100 | 8.5382 | 8.553 | 8.6585 | 8.545 |
| E1 (5) | 1 | Saline | 200 | 8.5455 | 8.56 | 8.7589 | 8.5523 |
| | 2 | Saline | 200 | 8.5267 | 8.542 | 8.7474 | 8.533 |
| | 3 | Saline | 200 | 8.534 | 8.549 | 8.754 | 8.556 |
| | 4 | Saline | 200 | 8.5078 | 8.523 | 8.7302 | 8.524 |
| | 5 | Saline | 200 | 8.5139 | 8.5293 | 8.7378 | 8.522 |
| | 6 | Saline | 200 | 8.5242 | 8.539 | 8.743 | 8.5344 |

TABLE 12-continued

Individual values for saline at 5 bars.

| Sample (bar) | # | Air loaded (mg) | Drug loaded (mg) | Drug residue (mg) | Drug released (mg) | Delivered (mass % of loaded) | Mean | SD | RSD % |
|---|---|---|---|---|---|---|---|---|---|
| P1 (5) | 1 | 15.9 | 97.0 | 1.2 | 95.8 | 98.8 | 96.1 | 3.2 | 3.3 |
|  | 2 | 14.6 | 103.0 | 1.6 | 101.4 | 98.4 |  |  |  |
|  | 3 | 15.5 | 103.1 | 2.5 | 100.6 | 97.6 |  |  |  |
|  | 4 | 15.2 | 100.5 | 2.5 | 98 | 97.5 |  |  |  |
|  | 5 | 15.8 | 101.6 | 9.2 | 92.4 | 90.9 |  |  |  |
|  | 6 | 14.8 | 105.5 | 6.8 | 98.7 | 93.6 |  |  |  |
| E1 (5) | 1 | 14.5 | 198.9 | 6.8 | 192.1 | 96.6 | 94.3 | 3.0 | 3.2 |
|  | 2 | 15.3 | 205.4 | 6.3 | 199.1 | 96.9 |  |  |  |
|  | 3 | 15.0 | 205.0 | 22.0 | 183 | 89.3 |  |  |  |
|  | 4 | 15.2 | 207.2 | 16.2 | 191 | 92.2 |  |  |  |
|  | 5 | 15.4 | 208.5 | 8.1 | 200.4 | 96.1 |  |  |  |
|  | 6 | 14.8 | 204.0 | 10.2 | 193.8 | 95.0 |  |  |  |

The mean results for dose release for the Saline formulation is 97 µl±3.3 for a 100 µl intended dose and 193.25 µl±6.3 for a 200 µl intended dose. For both intended doses (100 and 200 µl), the released dose results pass the acceptance criterion (less than 10% difference from target dose).

Droplet Size Determination by the Malvern Spraytec

The droplet size distribution values from the Malvern Spraytec measurements are outlined in Table 13 below and typical Graphs are seen in FIG. 18-21.

TABLE 13

Individual saline results for Malvern Spraytec.

| Run | Label | Volume (ul) | Pressure (Bar) | Average Dv(50) (um) | Average Dv(10) (um) | Actuation time(ms) | Mean Dv(50) (um) | SD | Mean Actuation time(ms) | SD | Mean Dv(10) (um) | SD |
|---|---|---|---|---|---|---|---|---|---|---|---|---|
| 1 | Saline E1 | 200 | 5 | 45.9 | 15.3 | 54 | 60.08 | 11.61 | 58.33 | 8.78 | 16.32 | 1.16 |
| 2 | Saline E1 | 200 | 5 | 78.6 | 18.1 | 60 |  |  |  |  |  |  |
| 3 | Saline E1 | 200 | 5 | 64.8 | 16.6 | 49 |  |  |  |  |  |  |
| 4 | Saline E1 | 200 | 5 | 61.4 | 16.7 | 69 |  |  |  |  |  |  |
| 5 | Saline E1 | 200 | 5 | 60 | 14.8 | 50 |  |  |  |  |  |  |
| 6 | Saline E1 | 200 | 5 | 49.8 | 16.4 | 68 |  |  |  |  |  |  |
| 1 | Saline P1 | 100 | 5 | 86.7 | 23.4 | 54 | 83.05 | 24.75 | 48.33 | 6.09 | 19.63 | 3.44 |
| 2 | Saline P1 | 100 | 5 | 76.3 | 18.5 | 38 |  |  |  |  |  |  |
| 3 | Saline P1 | 100 | 5 | 75.2 | 19.7 | 54 |  |  |  |  |  |  |
| 4 | Saline P1 | 100 | 5 | 1.25 | 22.5 | 49 |  |  |  |  |  |  |
| 5 | Saline P1 | 100 | 5 | 86.3 | 20 | 45 |  |  |  |  |  |  |
| 6 | Saline P1 | 100 | 5 | 48.8 | 13.7 | 50 |  |  |  |  |  |  |

Figure 18:
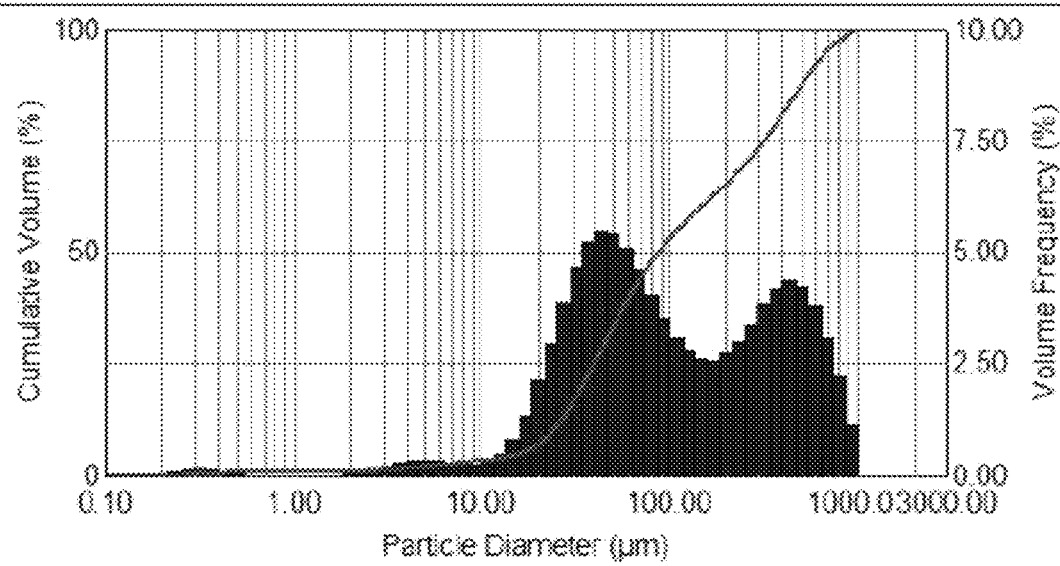
Figure 19:
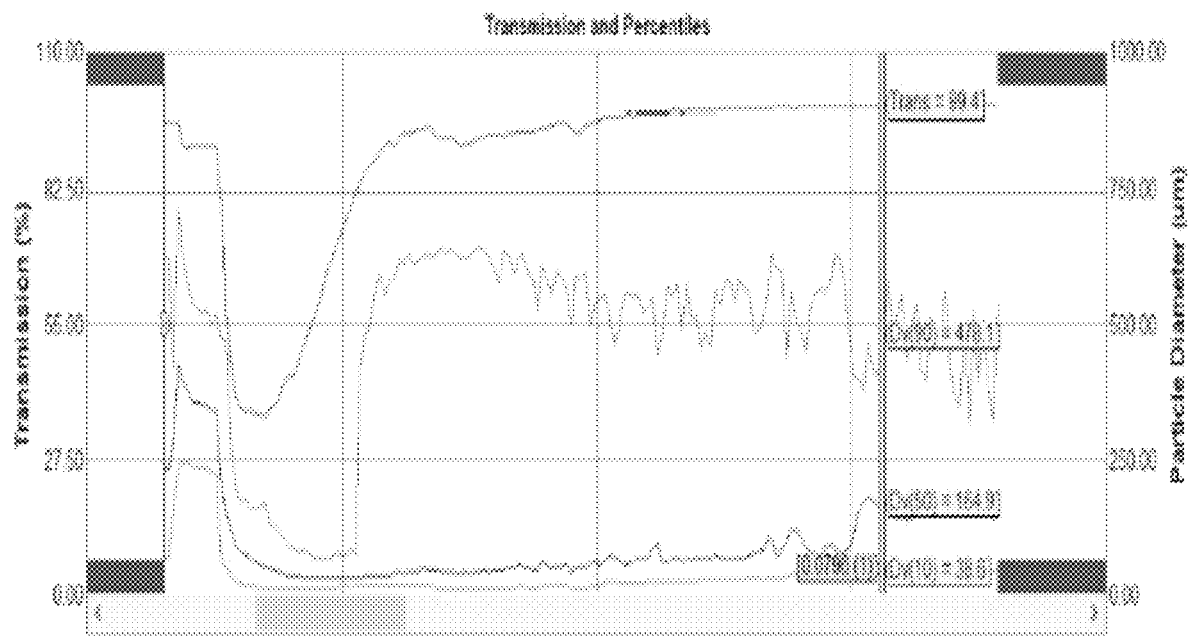
Figure 20:
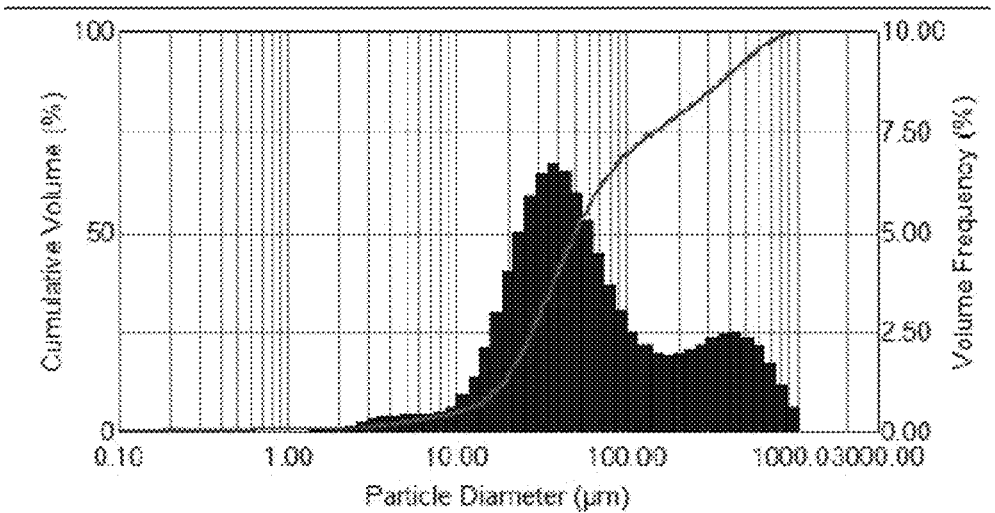
Figure 21:
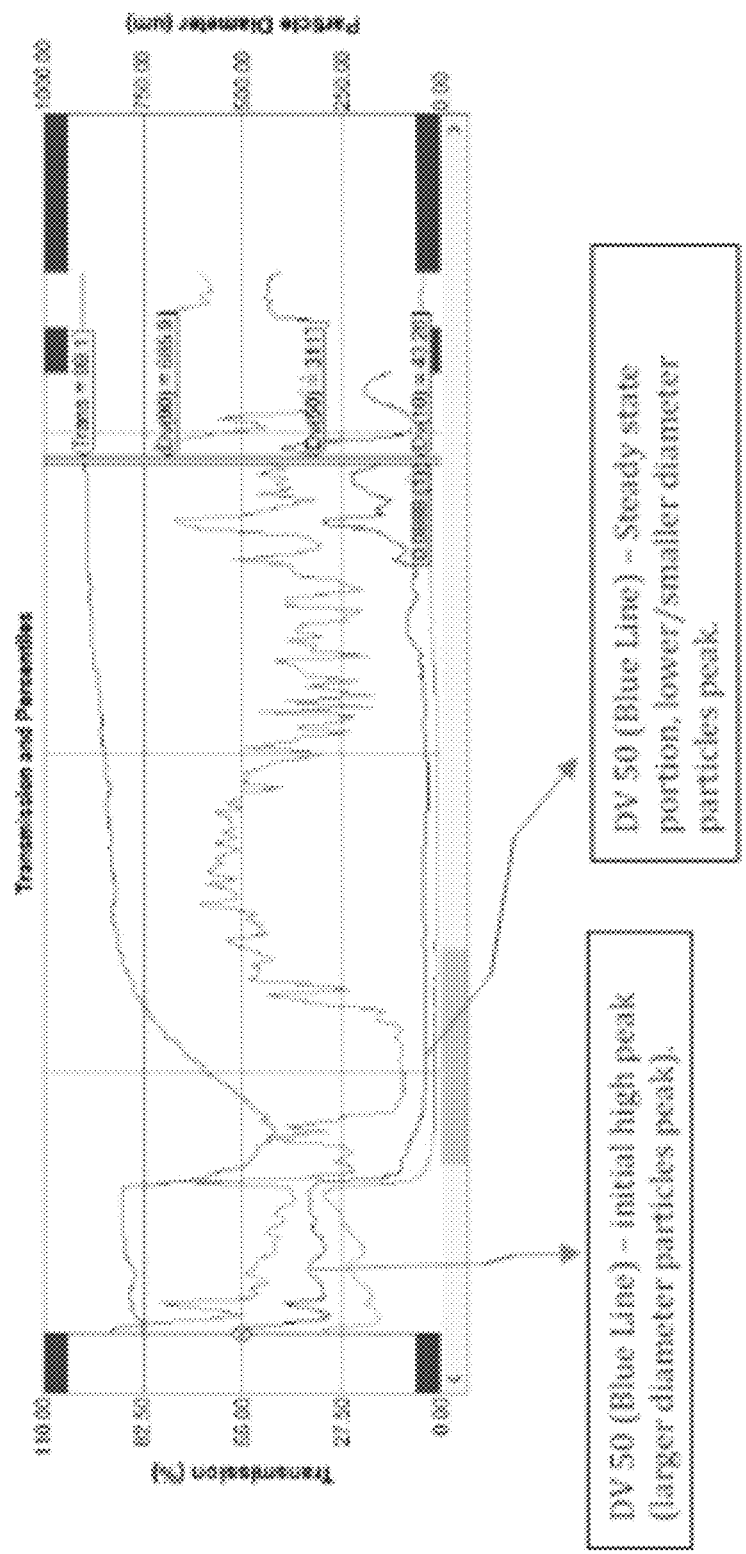

FIG. 18 shows, for Saline an example of mean droplet size distribution for a 100 µl fill volume. FIG. 19 shows, for Saline, an example of Dv(10), Dv(50) and Dv(90) vs. time for a 100 µl fill volume. FIG. 20 shows, for Saline, an example of mean droplet size distribution for a 200 µl fill volume. FIG. 21 shows, for Saline, an example of Dv(10), Dv(50) and Dv(90) vs. time for a 200 µl fill volume. The particle size distribution for both fill volumes shows a bimodal behavior with one peak above 100 µm and one below 100 µm as seen in both 100 µl and 200 µl doses. In the time sequenced distributions there is an initial stable part with a higher transmission around 90 to 95% that is shortest for 100 µl Saline fill volume as compared to the 200 µl Saline fill volume. Following this initial stable part comes a time period where the transmission drops markedly and then again increase up to 99%. The Dv(50) value of the 100 µl Saline fill volume (60.1 µm±11.6) and the 200 µl fill volume (83.0 µm±24.7) and the Dv(10) value of the 100 µl Saline fill volume was found to be 19.6±3.4 and for the 200 µl fill volume was found to be 16.3 µm±1.2; both pass the acceptance criteria.

Spray Pattern and Plume Geometry by Oxford Laser Envision

TABLE 14

Oxford Laser spray pattern results for saline.
Spray Pattern

| Run | Label | Volume (ul) | Pressure (Bar) | Short axis (cm) | Long axis (cm) | Oblongation | Mean | SD | SD % |
|---|---|---|---|---|---|---|---|---|---|
| 1 | Saline E1 | 200 | 5 | 2.21 | 3.33 | 1.51 | 1.51 | 0.050 | 3.28 |
| 2 | Saline E1 | 200 | 5 | 2.19 | 3.39 | 1.55 | | | |
| 3 | Saline E1 | 200 | 5 | 2.16 | 3.34 | 1.55 | | | |
| 4 | Saline E1 | 200 | 5 | 1.99 | 2.87 | 1.44 | | | |
| 1 | Saline P1 | 100 | 5 | 2.47 | 3.51 | 1.42 | 1.52 | 0.171 | 11.22 |
| 2 | Saline P1 | 100 | 5 | 2.28 | 3.36 | 1.47 | | | |
| 3 | Saline P1 | 100 | 5 | 2.36 | 3.33 | 1.41 | | | |
| 4 | Saline P1 | 100 | 5 | 2.06 | 3.65 | 1.77 | | | |

Figure 22:
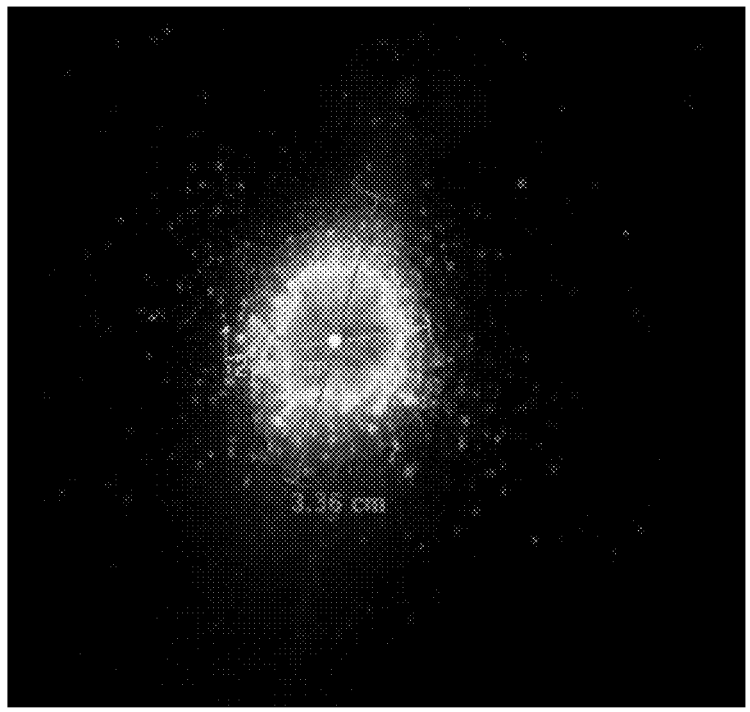
Figure 23:
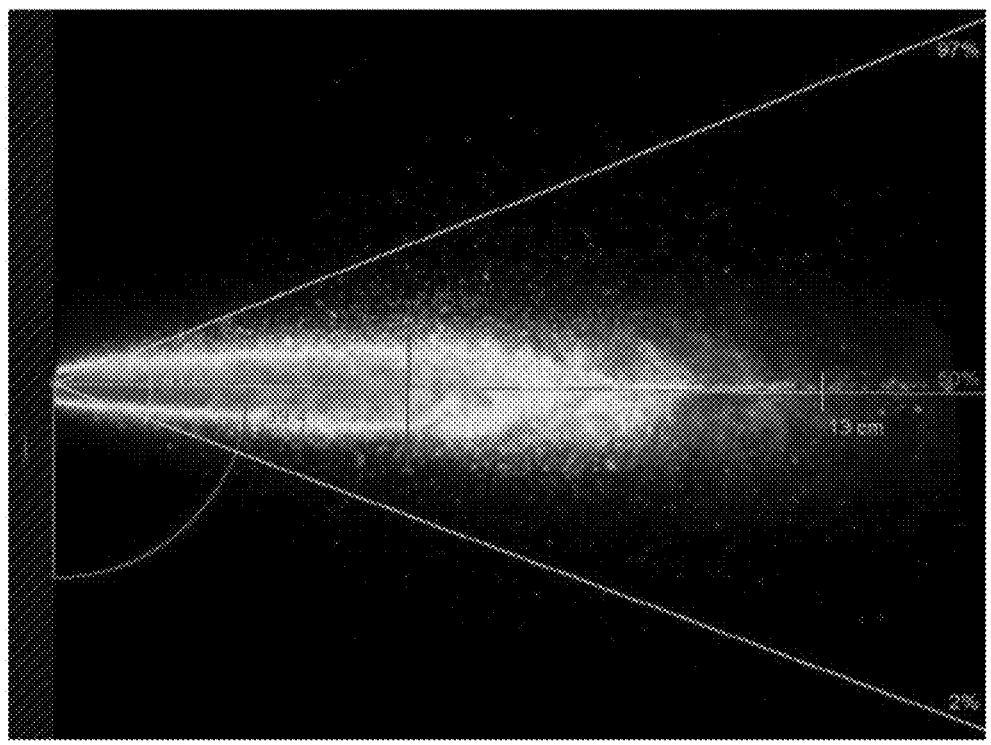

FIG. 22 shows, for saline, an example of spray pattern results for 100 µl. FIG. 23 shows, for saline, an example of spray pattern results for 200 µl.

Plume Geometry

TABLE 15

Oxford Laser plume geometry results for saline.
Plume Geometry

| Run | Label | Volume (ul) | Pressure (Bar) | Angle (Deg) | Width (at 6 cm) | Angle Mean | SD | SD % | Width Mean | SD | SD % |
|---|---|---|---|---|---|---|---|---|---|---|---|
| 1 | Saline E1 | 200 | 5 | 38.4 | 2.59 | 37.87 | 1.29 | 3.40 | 2.49 | 0.14 | 5.86 |
| 2 | Saline E1 | 200 | 5 | 36.4 | 2.43 | | | | | | |
| 3 | Saline E1 | 200 | 5 | 38.8 | 2.39 | | | | | | |
| 1 | Saline P1 | 100 | 5 | 41.8 | 2.85 | 40.70 | 4.36 | 10.70 | 2.75 | 0.18 | 6.62 |
| 2 | Saline P1 | 100 | 5 | 44.4 | 2.86 | | | | | | |
| 3 | Saline P1 | 100 | 5 | 35.9 | 2.54 | | | | | | |

FIG. 22 shows, for overall (total) spray pattern, an example of results for 100 µl saline. FIG. 23 shows, for a spray pattern, an example of results for 200 µl saline. The overall (total) spray pattern oblongation indexes for the saline 100 µl and 200 µl are 1.52±0.17 and 1.51±0.015, respectively, and thus pass the acceptance criterion. The plume geometry angle is 40.7±4.36 degrees for the 100 µl fill volume and 37.87±1.29 degrees for the 200 µl fill volume, with a width at 6 cm from the nozzle of 2.49±0.14 cm and 2.75±0.18 cm; thus, the device passes all acceptance criteria. It is noted that a bi-modal spray pattern, comprising a first pattern and a second pattern; further wherein the first pattern is characterized by (a) Plume angle is in the range of 5°±4°; (b) width of plume at 6 cm from the nozzle is in the range of 4 mm±3 mm; and, the second pattern is characterized by (a) Plume angle is in the range of 35°±10; (b) width of plume at 6 cm from the nozzle is in the range of 30±10 mm; further wherein the mean particle's size in the first pattern is larger than the mean particle's size in the second pattern.

Midazolam Formulation—Delivered Dose Determination

The mean values and standard deviations are presented in Table 16. All individual data are presented in Table 17

TABLE 16

Mean values of the delivered mass in % for midazolam.
Delivered mass in % of loaded mass

| Drug Name | Sample (X bar) | Volume µl | Mean | SD | RSD % |
|---|---|---|---|---|---|
| Midazoalm | Y1(5b) | 200 | 93.5 | 3.3 | 3.6 |
| | Y1(6b) | 200 | 93.8 | 2.6 | 2.8 |
| | W1(5b) | 400 | 93.5 | 2.5 | 2.7 |
| | W1(6b) | 400 | 94.4 | 3.8 | 4.1 |
| | T1(5b) | 600 | 94.3 | 1.5 | 1.6 |
| | T1(6b) | 600 | 94.7 | 2.1 | 2.2 |
| | U1(5b) | 800 | 94.8 | 1.9 | 2.0 |
| | U1(6b) | 800 | 94.6 | 2.1 | 2.3 |

Figure 24:
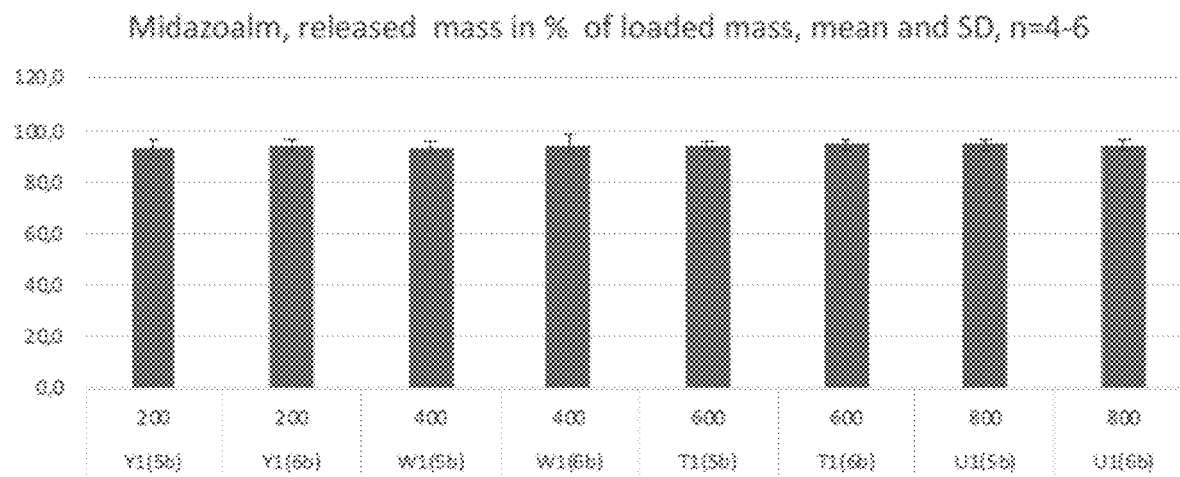

FIG. 24 shows, for a plot of mean values of released mass in % for midazolam 200 µl to 800 µl.

TABLE 17

Individual values for 200-800 µl midazolam; with 5 bar and 6 bar pressures

| Sample (bar) | # | Drug Name | Volume (ml) | Empty - before (g) | With Air (g) | With Drug (g) | After Dosing (g) |
|---|---|---|---|---|---|---|---|
| Y1 (5b) | 1 | Midazolam | 200 | 8.8913 | 8.90603 | 9.1217 | 8.91648 |
| | 2 | | | 8.9039 | 8.91922 | 9.12131 | 8.9222 |
| | 3 | | | 8.8894 | 8.90464 | 9.1067 | 8.8965 |

TABLE 17-continued

Individual values for 200-800 μl midazolam; with 5 bar and 6 bar pressures

|  |  |  |  |  |  |  |  |
|---|---|---|---|---|---|---|---|
|  | 4 |  |  | 8.8733 | 8.88784 | 9.08607 | 8.8793 |
|  | 5 |  |  | 8.8789 | 8.8937 | 9.0998 | 8.8903 |
|  | 6 |  |  | 8.8788 | 8.8944 | 9.0992 | 8.8915 |
| Y1 (6b) | 1 | Midazolam | 200 | 8.864 | 8.882 | 9.087 | 8.872 |
|  | 2 |  |  | 8.8888 | 8.906 | 9.113 | 8.905 |
|  | 3 |  |  | 8.8741 | 8.891 | 9.0879 | 8.882 |
|  | 4 |  |  | 8.8891 | 8.908 | 9.1236 | 8.9084 |
| W1 (5b) | 1 | Midazolam | 400 | 8.8763 | 8.8911 | 9.28976 | 8.9006 |
|  | 2 |  |  | 8.88081 | 8.89559 | 9.2978 | 8.9069 |
|  | 3 |  |  | 8.8569 | 8.38718 | 9.2699 | 8.8914 |
|  | 4 |  |  | 8.8818 | 8.89723 | 9.30461 | 8.8905 |
|  | 5 |  |  | 8.88571 | 8.90107 | 9.30512 | 8.9229 |
|  | 6 |  |  | 8.868 | 8.8823 | 9.2878 | 8.8942 |
| W1 (6b) | 1 | Midazolam | 400 | 8.8633 | 8.881 | 9.292 | 8.864 |
|  | 2 |  |  | 8.8722 | 8.8904 | 9.304 | 8.91 |
|  | 3 |  |  | 8.8886 | 8.9074 | 9.3218 | 8.8916 |
|  | 4 |  |  | 8.874 | 8.8909 | 9.3 | 8.901 |
| T1 (5b) | 1 | Midazolam | 600 | 8.91864 | 8.9349 | 9.5391 | 8.9544 |
|  | 2 |  |  | 8.9007 | 8.89145 | 9.5324 | 8.93953 |
|  | 3 |  |  | 8.89785 | 8.91264 | 9.52766 | 8.9165 |
|  | 4 |  |  | 8.91403 | 8.9283 | 9.5388 | 8.9441 |
|  | 5 |  |  | 8.9215 | 8.9369 | 9.5538 | 8.96327 |
|  | 6 |  |  | 8.90902 | 8.9235 | 9.5231 | 8.951 |
| T1 (6b) | 1 | Midazolam | 600 | 8.9045 | 8.921 | 9.523 | 8.918 |
|  | 2 |  |  | 8.883 | 8.9 | 9.5 | 8.917 |
|  | 3 |  |  | 8.88 | 8.8971 | 9.514 | 8.921 |
|  | 4 |  |  | 8.892 | 8.909 | 9.5174 | 8.932 |
| U1 (5b) | 1 | Midazolam | 800 | 8.91637 | 8.93003 | 9.7435 | 8.96922 |
|  | 2 |  |  | 8.87642 | 8.8911 | 9.7063 | 8.938 |
|  | 3 |  |  | 8.86607 | 8.8819 | 9.6903 | 8.9138 |
|  | 4 |  |  | 8.89065 | 8.9069 | 9.7185 | 8.929 |
|  | 5 |  |  | 8.9113 | 8.9266 | 9.72042 | 8.92985 |
|  | 6 |  |  | 8.88098 | 8.8961 | 9.69 | 8.91247 |
| U1 (6b) | 1 | Midazolam | 800 | 8.877 | 8.894 | 9.699 | 8.9105 |
|  | 2 |  |  | 8.894 | 8.912 | 9.708 | 8.931 |
|  | 3 |  |  | 8.887 | 8.905 | 9.724 | 8.921 |
|  | 4 |  |  | 8.8992 | 8.9162 | 9.7167 | 8.9678 |

| Sample (bar) | # | Air loaded (mg) | Drug loaded (mg) | Drug residue (mg) | Drug released (mg) | Delivered (mass % of loaded) | Mean | SD | RSD % |
|---|---|---|---|---|---|---|---|---|---|
| Y1 (5b) | 1 | 14.7 | 215.7 | 25.2 | 190.49 | 88.3 | 93.5 | 3.3 | 3.6 |
|  | 2 | 15.3 | 202.1 | 18.3 | 183.79 | 90.9 |  |  |  |
|  | 3 | 15.2 | 202.1 | 7.1 | 194.96 | 96.5 |  |  |  |
|  | 4 | 14.5 | 198.2 | 6.0 | 192.23 | 97.0 |  |  |  |
|  | 5 | 14.8 | 206.1 | 11.4 | 194.7 | 94.5 |  |  |  |
|  | 6 | 15.6 | 204.8 | 12.7 | 192.1 | 93.8 |  |  |  |
| Y1 (6b) | 1 | 18.0 | 205.0 | 8.0 | 197 | 96.1 | 93.8 | 2.6 | 2.8 |
|  | 2 | 17.2 | 207.0 | 16.2 | 190.8 | 92.2 |  |  |  |
|  | 3 | 16.9 | 196.9 | 7.9 | 189 | 96.0 |  |  |  |
|  | 4 | 18.9 | 215.6 | 19.3 | 196.3 | 91.0 |  |  |  |
| W1 (5b) | 1 | 14.8 | 398.7 | 24.3 | 374.36 | 93.9 | 93.5 | 2.5 | 2.7 |
|  | 2 | 14.8 | 402.2 | 26.1 | 376.12 | 93.5 |  |  |  |
|  | 3 | 14.9 | 398.1 | 34.5 | 363.6 | 91.3 |  |  |  |
|  | 4 | 15.4 | 407.4 | 8.7 | 398.68 | 97.9 |  |  |  |
|  | 5 | 15.4 | 404.1 | 37.2 | 366.86 | 90.8 |  |  |  |
|  | 6 | 14.3 | 405.5 | 26.2 | 379.3 | 93.5 |  |  |  |
| W1 (6b) | 1 | 17.7 | 411.0 | 0.7 | 410.3 | 99.8 | 94.4 | 3.8 | 4.1 |
|  | 2 | 18.2 | 413.6 | 37.8 | 375.8 | 90.9 |  |  |  |
|  | 3 | 18.8 | 414.4 | 27.4 | 387 | 93.4 |  |  |  |
|  | 4 | 16.9 | 409.1 | 27.0 | 382.1 | 93.4 |  |  |  |
| T1 (5b) | 1 | 16.3 | 604.2 | 35.8 | 568.44 | 94.1 | 94.3 | 1.5 | 1.6 |
|  | 2 | 14.4 | 617.9 | 39.4 | 578.47 | 93.6 |  |  |  |
|  | 3 | 14.8 | 615.0 | 18.6 | 596.37 | 97.0 |  |  |  |
|  | 4 | 14.3 | 610.5 | 30.1 | 580.43 | 95.1 |  |  |  |
|  | 5 | 15.4 | 616.9 | 41.8 | 575.13 | 93.2 |  |  |  |
|  | 6 | 14.5 | 599.6 | 42.0 | 557.62 | 93.0 |  |  |  |
| T1 (6b) | 1 | 16.5 | 602.0 | 13.5 | 588.5 | 97.8 | 94.7 | 2.1 | 2.2 |
|  | 2 | 17.0 | 600.0 | 34.0 | 566 | 94.3 |  |  |  |
|  | 3 | 17.1 | 616.9 | 41.0 | 575.9 | 93.4 |  |  |  |
|  | 4 | 17.0 | 608.4 | 40.0 | 568.4 | 93.4 |  |  |  |
| U1 (5b) | 1 | 13.7 | 813.5 | 52.8 | 760.62 | 93.5 | 94.8 | 1.9 | 2.0 |
|  | 2 | 14.7 | 815.2 | 61.6 | 753.62 | 92.4 |  |  |  |
|  | 3 | 15.8 | 808.4 | 47.7 | 760.67 | 94.1 |  |  |  |
|  | 4 | 16.0 | 811.6 | 18.1 | 773.45 | 95.3 |  |  |  |
|  | 5 | 15.3 | 793.8 | 18.5 | 775.27 | 97.7 |  |  |  |
|  | 6 | 15.1 | 793.9 | 31.5 | 762.41 | 96.0 |  |  |  |

TABLE 17-continued

| | | | | | | | | | |
|---|---|---|---|---|---|---|---|---|---|
| Individual values for 200-800 μl midazolam; with 5 bar and 6 bar pressures | | | | | | | | | |
| U1 (6b) | 1 | 17.0 | 805.0 | 33.5 | 771.5 | 95.8 | 94.6 | 2.1 | 2.3 |
| | 2 | 18.0 | 796.0 | 37.0 | 759 | 95.4 | | | |
| | 3 | 18.0 | 819.0 | 34.0 | 785 | 95.8 | | | |
| | 4 | 17.0 | 800.5 | 68.6 | 731.9 | 91.4 | | | |

The mean results for dose release for the midazolam formulation varied between 93.5%±3.3 and 94.8±1.9 for 200 μl to 800 μl intended doses at a pressure of 5 bar and 93.8%±2.6 to 94.7%±2.1 for 200 μl to 800 μl intended doses at a pressure of 6 bar. In all of the above cases, the released dose results pass the acceptance criteria (less than 10% difference from the target dose). All doses were release with mean of less than 10% of target dose, which is very unique in the field, that same device and technology (with no change at all) can fit such a range of volumes, and particularly high volumes and be so efficient in releasing the aerosolized drug.

Droplet Size Determination by the Malvern Spraytec

Below is a table and figures showing the mean droplet size distribution for midazolam. The device/formulation was tested primarily at 5 bar pressure for 200 μl, 400 μl, 600 μl and 800 μl. 6 bar measurements were performed for 200 μl and 400 μl fill volume of midazolam.

Figure 25:
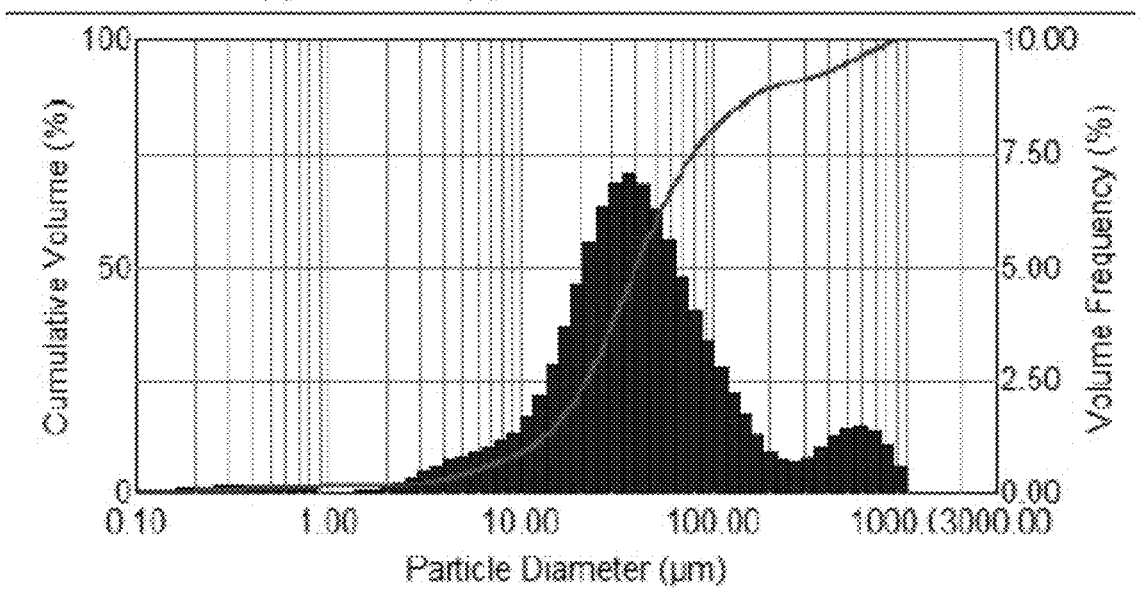
Figure 26:
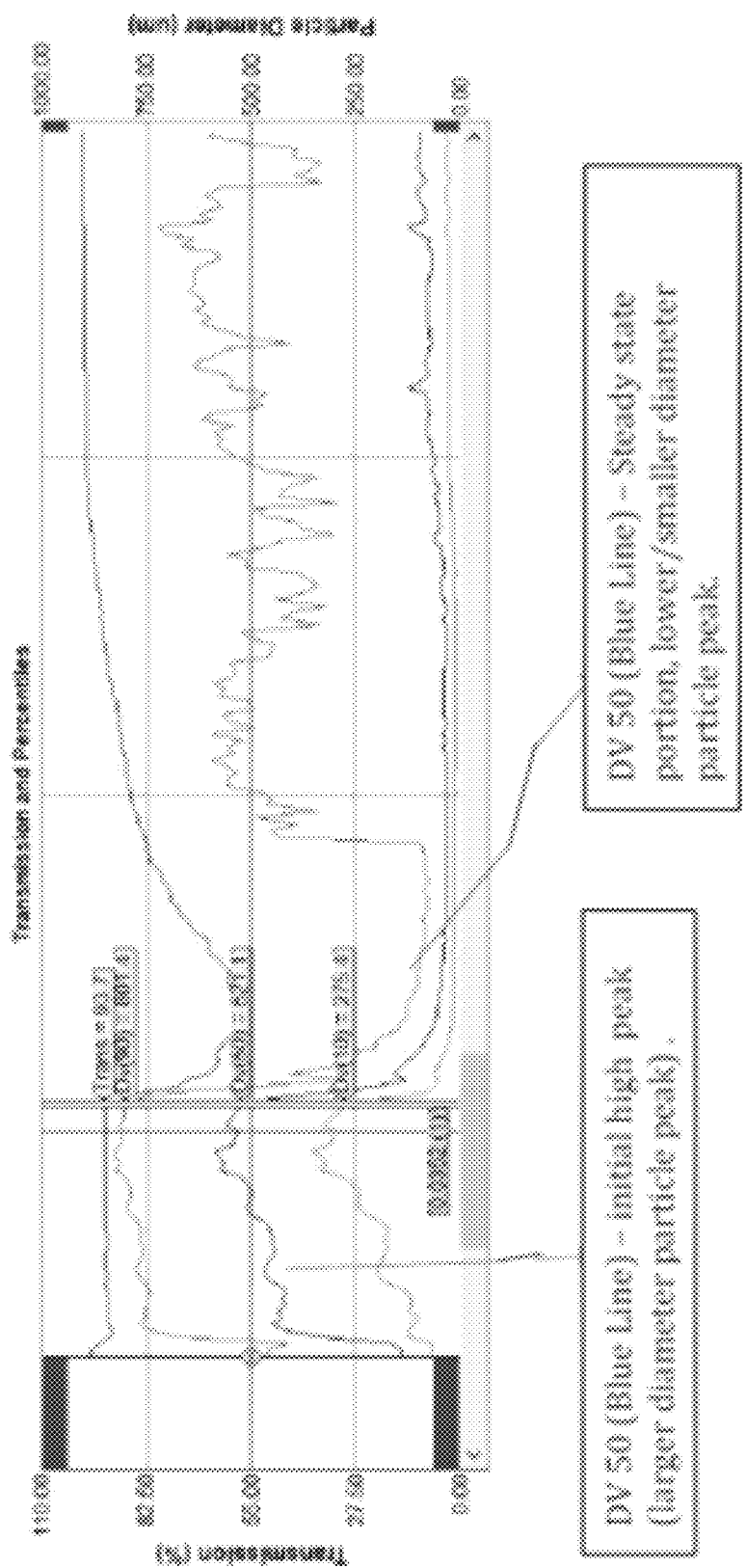
Figure 27:
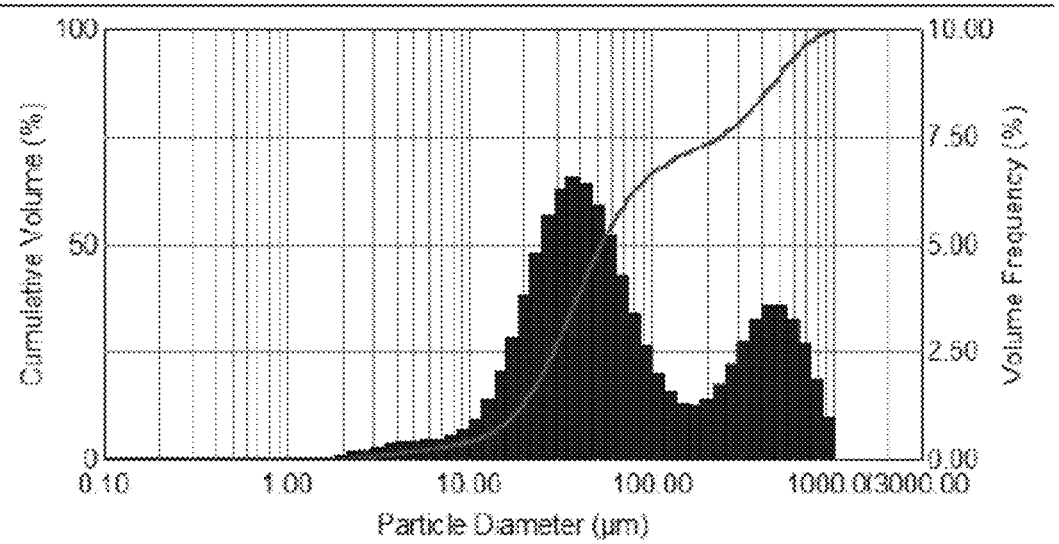
Figure 28:
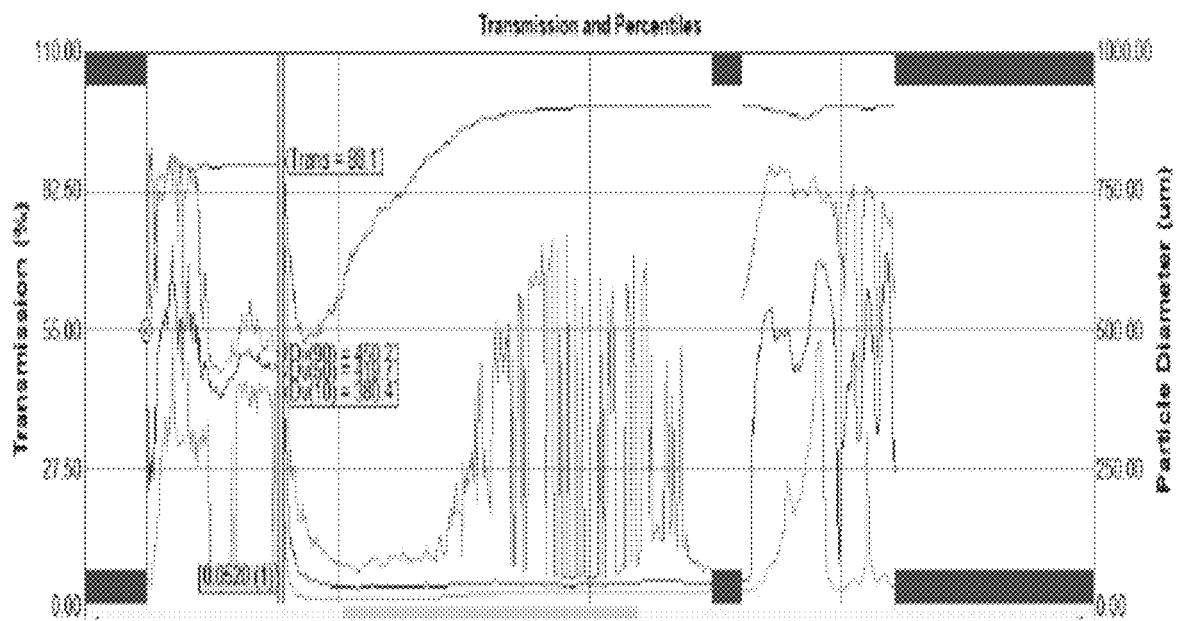
Figure 29:
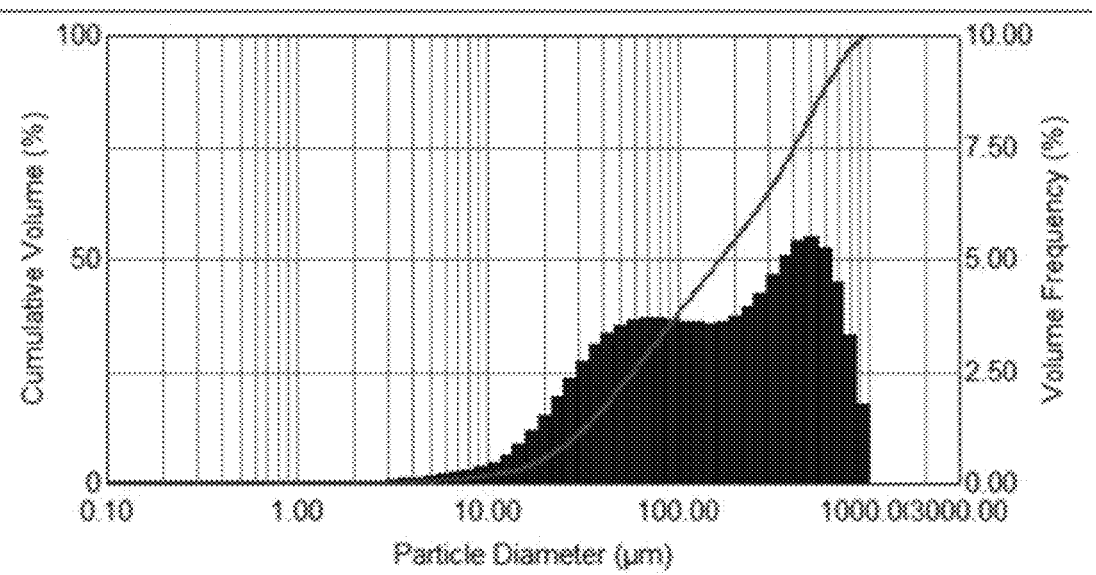
Figure 30:
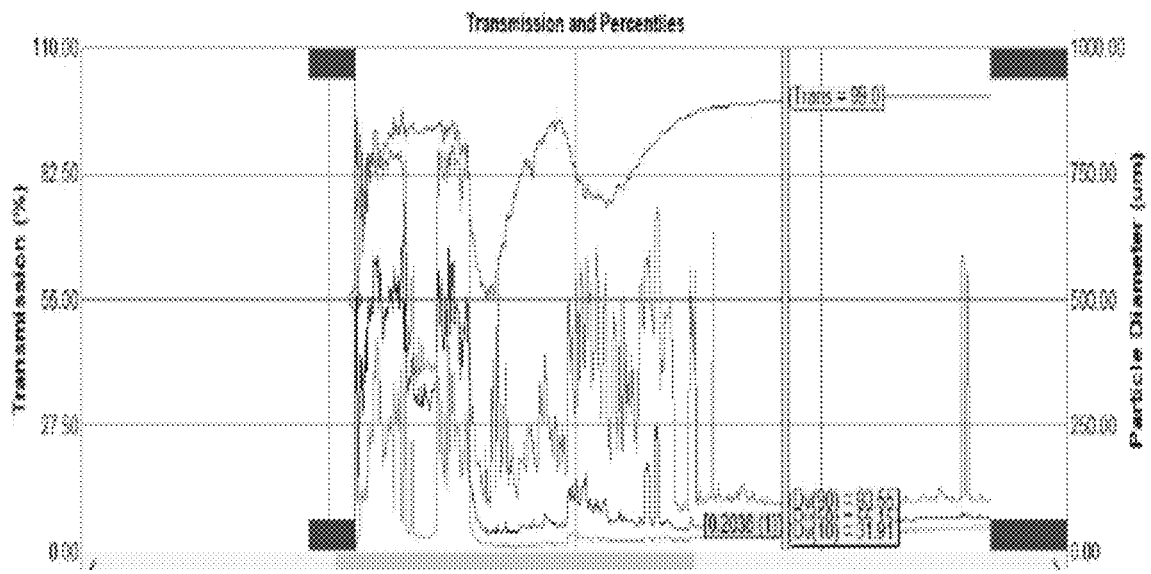
Figure 31:
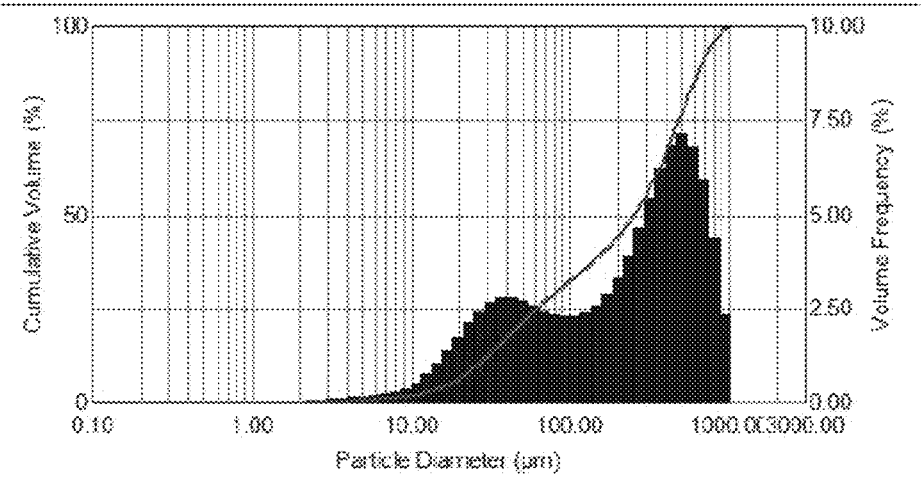
Figure 32:
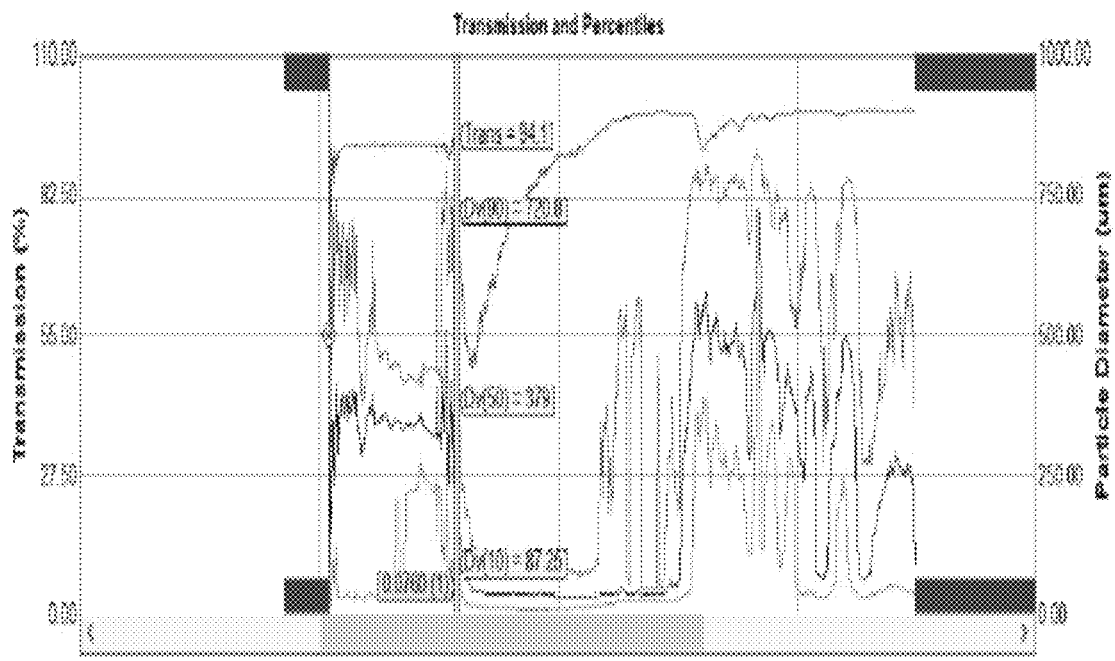
Figure 33:
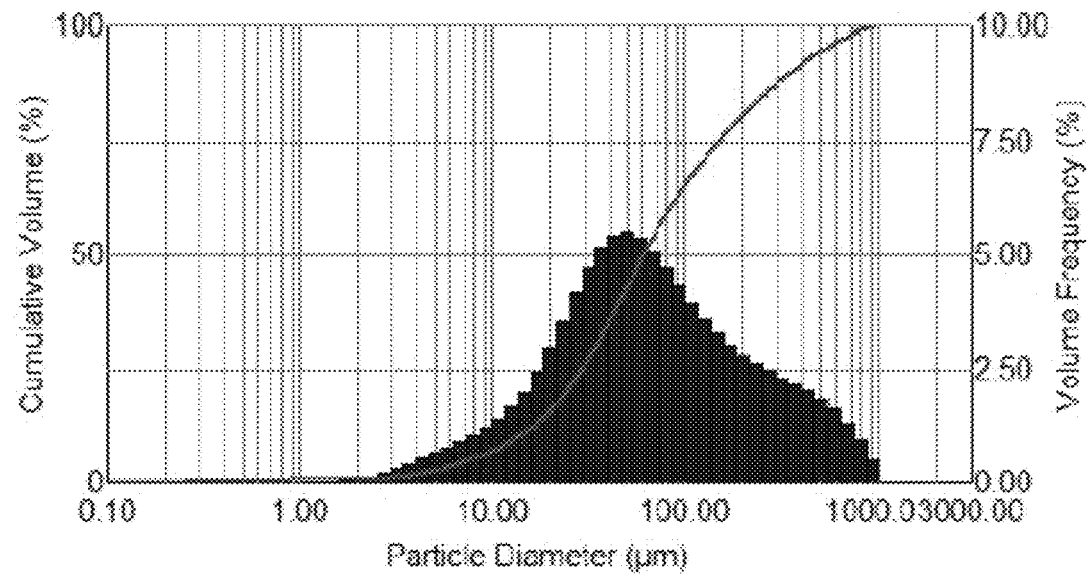

FIG. 25 shows, for midazolam, an example of mean droplet size distribution for 200 μl fill volume at 5 Bar. FIG. 26 shows, for midazolam, an example of Dv(10), Dv(50) and Dv(90) vs. time for 200 μl fill volume at 5 Bar. FIG. 27 shows, for midazolam, an example of mean droplet size distribution for 400 μl fill volume at 5 Bar. FIG. 28 shows, for midazolam, an example of Dv(10), Dv(50) and Dv(90) vs. time for 400 μl fill volume at 5 Bar. FIG. 29 shows, for midazolam, an example of mean droplet size distribution for 600 μl fill volume at 5 Bar. FIG. 30 shows, for midazolam, an example of Dv(10), Dv(50) and Dv(90) vs. time for 600 μl fill volume at 5 Bar. FIG. 31 shows, for midazolam, an example of mean droplet size distribution for 800 μl fill volume at 5 Bar. FIG. 32 shows, for midazolam, an example of Dv(10), Dv(50) and Dv(90) vs. time for 800 μl fill volume at 5 Bar. FIG. 33 shows, for midazolam, an example of mean droplet size distribution for 200 μl fill volume at 6 Bar. This exception where only one defined pick is seen also falls under the criteria of the SipNose aerosol as stated above—if a monomodal spray pattern is shown, the particle size and plume geometry are comparable to the steady state pick (second pick on a time scale of the bi-modal aerosol pattern).

TABLE 18

Individual results as measured by the Malvern Spraytec

| Run | Label | Volume (ul) | Pressure (Bar) | Average Dv(50) (um) | Average Dv(10) (um) | Actuation time(ms) | Mean Dv(50) (um) | SD | Mean Actuation time(ms) | SD | Mean Dv(10) (um) | SD |
|---|---|---|---|---|---|---|---|---|---|---|---|---|
| 1 | Midazolam R1 | 200 | 5 | 46.8 | 13.2 | 84 | 55.64 | 67.78 | 88.00 | 44.82 | 16.12 | 3.84 |
| 2 | Midazolam R1 | 200 | 5 | 61.6 | 18.9 | 124 | | | | | | |
| 3 | Midazolam R1 | 200 | 5 | 61.5 | 17.6 | 58 | | | | | | |
| 4 | Midazolam R1 | 200 | 5 | 68.4 | 19.9 | 80 | | | | | | |
| 5 | Midazolam R1 | 200 | 5 | 39.9 | 11 | 69 | | | | | | |
| 1 | Midazolam S1 | 400 | 5 | 106.7 | 20.4 | 109 | 74.17 | 22.80 | 121.83 | 31.82 | 19.50 | 2.43 |
| 2 | Midazolam S1 | 400 | 5 | 52.8 | 17.2 | 96 | | | | | | |
| 3 | Midazolam S1 | 400 | 5 | 97.2 | 23.2 | 170 | | | | | | |
| 4 | Midazolam S1 | 400 | 5 | 69.7 | 19.2 | 103 | | | | | | |
| 5 | Midazolam S1 | 400 | 5 | 52.5 | 17.5 | 99 | | | | | | |
| 6 | Midazolam S1 | 400 | 5 | 66.1 | 19.7 | 154 | | | | | | |
| 1 | Midazolam T1 | 600 | 5 | 215.3 | 30.8 | 158 | 146.10 | 59.13 | 165.83 | 21.82 | 27.24 | 4.32 |
| 2 | Midazolam T1 | 600 | 5 | 165.7 | 28.1 | 191 | | | | | | |
| 3 | Midazolam T1 | 600 | 5 | 115.6 | 22.3 | 138 | | | | | | |
| 4 | Midazolam T1 | 600 | 5 | 90.6 | 23.2 | 184 | | | | | | |
| 5 | Midazolam T1 | 600 | 5 | 209.1 | 31.9 | 148 | | | | | | |
| 6 | Midazolam T1 | 600 | 5 | 80.3 | 19.8 | 178 | | | | | | |
| 1 | Midazolam V1 | 800 | 5 | 276.6 | 30.2 | 201 | 261.18 | 94.61 | 192.17 | 28.94 | 29.90 | 2.38 |
| 2 | Midazolam V1 | 800 | 5 | 391.6 | 31.0 | 204 | | | | | | |
| 3 | Midazolam V1 | 800 | 5 | 243.6 | 30.4 | 198 | | | | | | |
| 4 | Midazolam V1 | 800 | 5 | 302.9 | 32.1 | 233 | | | | | | |
| 5 | Midazolam V1 | 800 | 5 | 250.4 | 25.9 | 153 | | | | | | |
| 6 | Midazolam V1 | 800 | 5 | 102 | 19.2 | 158 | | | | | | |
| 1 | Midazolam W1 | 400 | 6 | 146 | 20.4 | 122 | 156.75 | 48.84 | 128.67 | 32.71 | 23.80 | 6.16 |
| 2 | Midazolam W1 | 400 | 6 | 221.1 | 34.3 | 79 | | | | | | |
| 3 | Midazolam W1 | 400 | 6 | 214.9 | 21.6 | 117 | | | | | | |
| 4 | Midazolam W1 | 400 | 6 | 111.4 | 18.8 | 174 | | | | | | |
| 5 | Midazolam W1 | 400 | 6 | 127.2 | 24.0 | 126 | | | | | | |
| 6 | Midazolam W1 | 400 | 6 | 119.9 | 22.0 | 154 | | | | | | |
| 1 | Midazolam Y1 | 200 | 6 | 55.5 | 15 | 66 | 66.23 | 8.77 | 95.33 | 18.45 | 15.22 | 1.00 |
| 2 | Midazolam Y1 | 200 | 6 | 69.4 | 16.1 | 116 | | | | | | |
| 3 | Midazolam Y1 | 200 | 6 | 60.6 | 13.5 | 88 | | | | | | |
| 4 | Midazolam Y1 | 200 | 6 | 63.4 | 14.9 | 92 | | | | | | |
| 5 | Midazolam Y1 | 200 | 6 | 81 | 15.6 | 114 | | | | | | |
| 6 | Midazolam Y1 | 200 | 6 | 67.5 | 16.2 | 92 | | | | | | |

Figure 34:
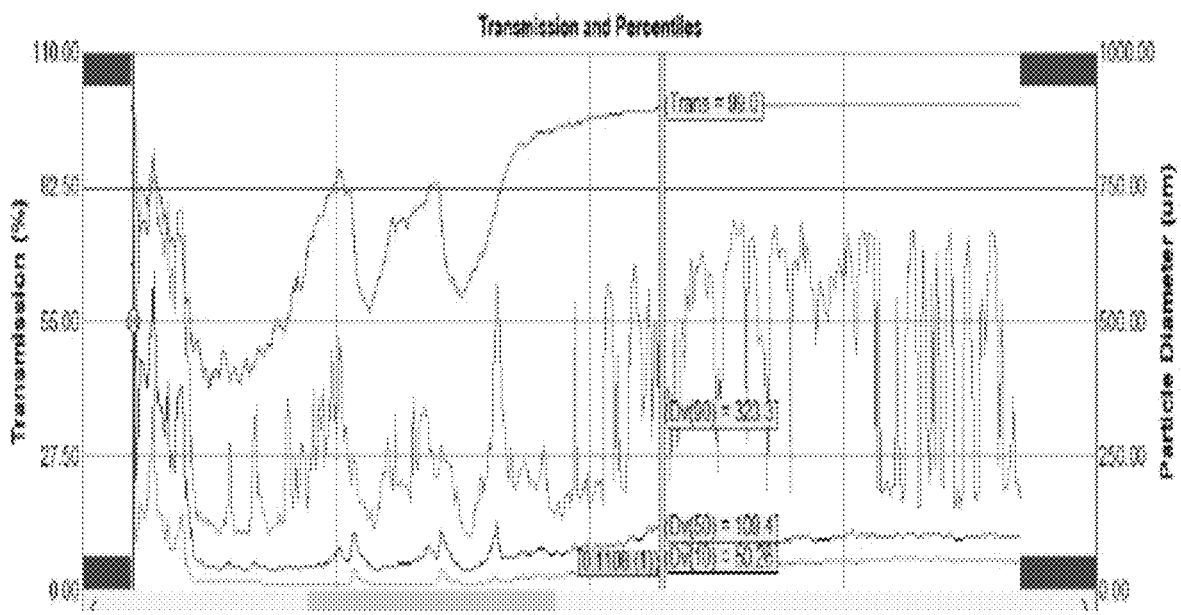
Figure 35:
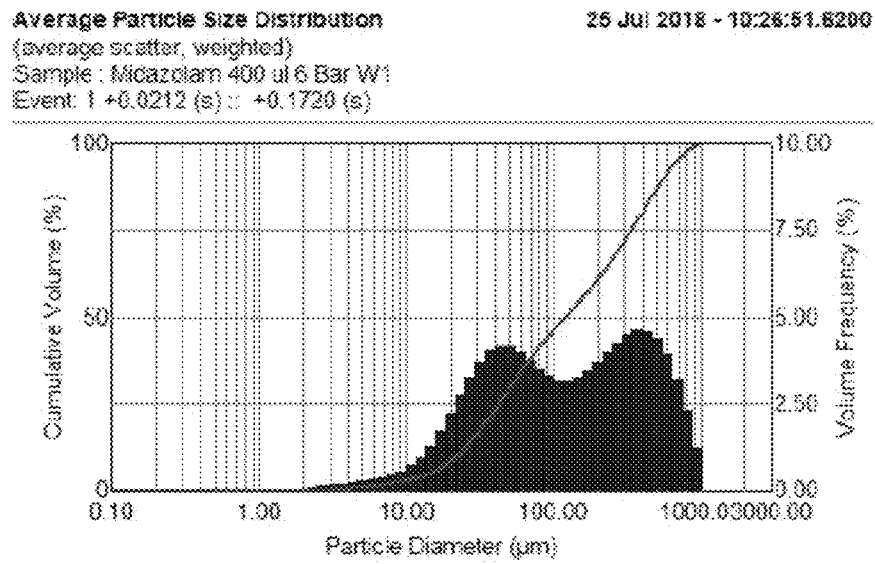
Figure 36:
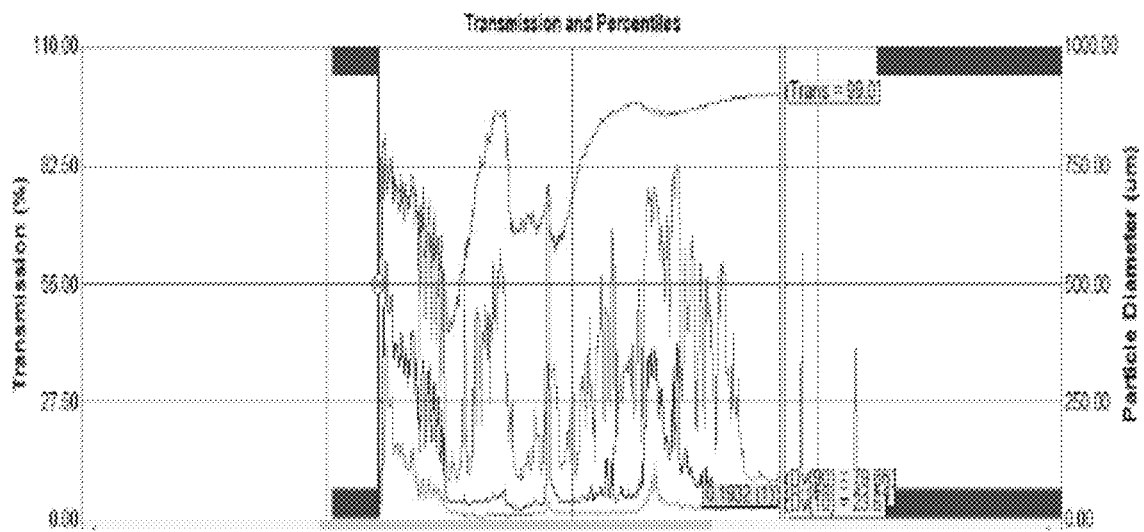

FIG. 34 shows, for midazolam, an example of Dv(10), Dv(50) and Dv(90) vs. time for 200 μl fill volume at 6 Bar. FIG. 35 shows, for midazolam, an example of mean droplet size distribution for 400 μl fill volume at 6 Bar. FIG. 36 shows, for midazolam, an example of Dv(10), Dv(50) and Dv(90) vs. time for 400 μl fill volume at 6 Bar.

Spray Pattern and Plume Geometry as measured by the Oxford Laser Envision

TABLE 19

Spray Pattern; Individual results as measured by the Oxford Laser Envision
Spray Pattern

| Run | Label | Volume (ul) | Pressure (Bar) | Short axis (cm) | Long axis (cm) | Oblongation | Mean | SD | SD % |
|---|---|---|---|---|---|---|---|---|---|
| 1 | Midazolam T1 | 600 | 6 | 2 | 3.13 | 1.57 | 1.59 | 0.092 | 5.76 |
| 2 | Midazolam T1 | 600 | 6 | 2.18 | 3.33 | 1.53 | | | |
| 3 | Midazolam T1 | 600 | 6 | 1.77 | 3.06 | 1.73 | | | |
| 4 | Midazolam T1 | 600 | 6 | 2.36 | 3.66 | 1.55 | | | |
| 1 | Midazolam U1 | 800 | 6 | 1.98 | 3.1 | 1.57 | 1.61 | 0.068 | 4.24 |
| 2 | Midazolam U1 | 800 | 6 | 2.05 | 3.44 | 1.68 | | | |
| 3 | Midazolam U1 | 800 | 6 | 2.46 | 3.77 | 1.53 | | | |
| 4 | Midazolam U1 | 800 | 6 | 1.87 | 3.08 | 1.65 | | | |
| 1 | Midazolam W1 | 400 | 6 | 2.07 | 3.19 | 1.54 | 1.53 | 0.178 | 11.62 |
| 2 | Midazolam W1 | 400 | 6 | 2.24 | 3.28 | 1.46 | | | |
| 3 | Midazolam W1 | 400 | 6 | 2.97 | 4.02 | 1.35 | | | |
| 4 | Midazolam W1 | 400 | 6 | 1.95 | 3.46 | 1.77 | | | |
| 1 | Midazolam Y1 | 200 | 6 | 1.94 | 3.2 | 1.65 | 1.57 | 0.062 | 3.93 |
| 2 | Midazolam Y1 | 200 | 6 | 1.82 | 2.89 | 1.59 | | | |
| 3 | Midazolam Y1 | 200 | 6 | 2.1 | 3.24 | 1.54 | | | |
| 4 | Midazolam Y1 | 200 | 6 | 1.6 | 2.41 | 1.51 | | | |

FIG. 35 shows, for midazolam, an example of Dv(10), Dv(50) and Dv(90) vs. time for a 600 μl fill volume, FIG. 36 shows, for midazolam, an example of Dv(10), Dv(50) and Dv(90) vs. time for a 400 μl fill volume at 6 bar. The particle size distribution for all fill volumes at (200 μl-800 μl) and 5 bar and 6 bar actuations, show a bimodal behavior with one peak above 100 μm and one peak below 100 μm. In the time sequence distributions, there is an initial stable part with a higher transmission around 90% to 95% that is slightly shorter for the 200 μl midazolam fill volume and increases with increasing fill volume. Following this initial stable part comes a time period where the transmission drops markedly and again increases up to 99%. The initial stable part seen in the 5 bar investigations is less pronounced in the 6 bar actuations. The Dv(50) values of the overall Dv(50) calculated for aerosol release of 200 μl, 400 μl and 600 μl (55.64 μm±67, 74.2 μm±22.8, 146 μm±59 μm respectively) at 5 bar, and for aerosol release of 200 μl and 400 μl (66.23 μm±8.7 and 156.75 μm±48.8 respectively) at 6 bars, all pass the acceptance criteria. Only the 800 μl volume at 5 bars (261 μm±94 μm) is slightly above the acceptance criterion (261 μm instead of 250 μm) and as 800 μl released dose is so unique in the field, acceptance criteria for those volumes were broaden to include the very mild change from all other volumes released. The Dv(10) values, that are the ones that are crucial for safety, for all volumes (200 μl, 400 μl and 600 μl and 800 μl) in both 5 bar and 6 bar actuations are all above 10 μm, thus all pass this acceptance criterion.

Plume Geometry

TABLE 20

Plume Geometry; individual results as measured by the Malvern Spraytec.
Plume Geometry

| Run | Label | Volume (ul) | Pressure (Bar) | Angle (Deg) | Width (at 6 cm) | Angle Mean | Angle SD | Angle SD % | Width Mean | Width SD | Width SD % |
|---|---|---|---|---|---|---|---|---|---|---|---|
| 1 | Midazolam N1 | 800 | 5 | 24.3 | 2.07 | 30.80 | 10.24 | 33.24 | 2.59 | 0.74 | 28.54 |
| 2 | Midazolam N1 | 800 | 5 | 25.5 | 2.27 | | | | | | |
| 3 | Midazolam N1 | 800 | 5 | 42.6 | 3.44 | | | | | | |
| 1 | Midazolam R1 | 200 | 5 | 25.6 | 2.16 | 29.57 | 3.95 | 13.36 | 2.39 | 0.28 | 11.74 |
| 2 | Midazolam R1 | 200 | 5 | 33.5 | 2.7 | | | | | | |
| 3 | Midazolam R1 | 200 | 5 | 29.6 | 2.3 | | | | | | |
| 1 | Midazolam T1 | 600 | 6 | 30.3 | 2.7 | 32.87 | 2.32 | 7.05 | 2.85 | 0.17 | 5.83 |
| 2 | Midazolam T1 | 600 | 6 | 34.8 | 3.03 | | | | | | |
| 3 | Midazolam T1 | 600 | 6 | 33.5 | 2.83 | | | | | | |
| 1 | Midazolam U1 | 800 | 6 | 31.5 | 2.62 | 30.57 | 2.34 | 7.67 | 2.60 | 0.16 | 6.02 |
| 2 | Midazolam U1 | 800 | 6 | 32.3 | 2.74 | | | | | | |
| 3 | Midazolam U1 | 800 | 6 | 27.9 | 2.43 | | | | | | |
| 1 | Midazolam W1 | 400 | 6 | 31.8 | 2.83 | 34.10 | 2.17 | 6.35 | 3.07 | 0.23 | 7.39 |
| 2 | Midazolam W1 | 400 | 6 | 34.4 | 3.11 | | | | | | |
| 3 | Midazolam W1 | 400 | 6 | 36.1 | 3.28 | | | | | | |
| 1 | Midazolam Y1 | 200 | 6 | 35.5 | 3.23 | 36.20 | 1.30 | 3.59 | 3.09 | 0.22 | 7.22 |
| 2 | Midazolam Y1 | 200 | 6 | 37.7 | 3.2 | | | | | | |
| 3 | Midazolam Y1 | 200 | 6 | 35.4 | 2.83 | | | | | | |

Figure 37:
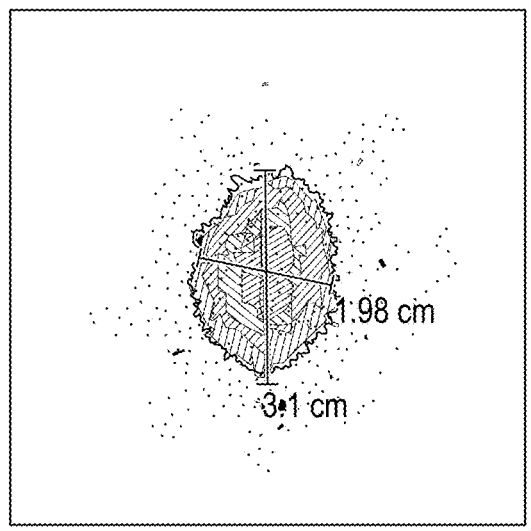
Figure 38:
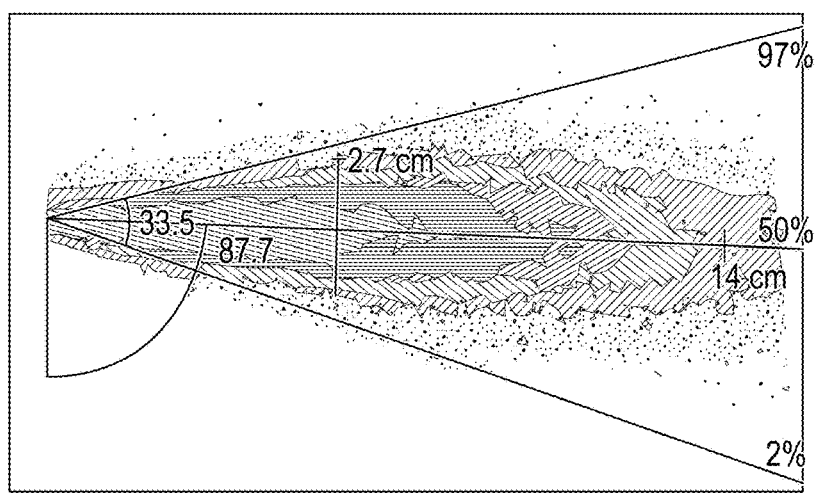
Figure 39:
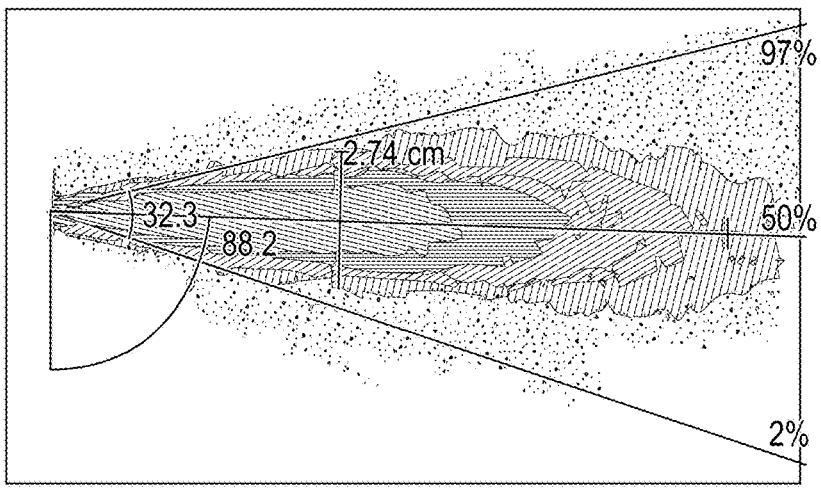

FIG. 37 shows, for plume geometry, an example of results for midazolam 200 µl. FIG. 38 shows, for plume geometry, an example of results for midazolam 200 µl saline. FIG. 39 shows, for plume geometry, an example of results for midazolam 800 µl saline. The spray pattern of the midazolam formulations has a mean oblongation index of around 1.6 with SD values that indicate no difference in the oblongation index between the four different fill volumes (200 µl, 400 µl and 600 µl and 800 µl) in the 5 bar and 6 bar pressures, and all pass the acceptance criteria, where short axis and long axis are no longer than 4 cm and the ratio between the longest to the shortest axes (oblongation) is in the range of 1.5±1. The overall (total) plume geometry has a mean of 30 degrees to 36 degrees for all fill volumes and for both 5 bar and 6 bar actuation pressure. All results passed the acceptance criteria for overall (total) plume angle of 35°±10 (except for 800 µl at 5 bars which showed slightly lower values (30.8°±10 instead of 35°±10 and as stated above, specifically will be adapted and pass acceptance criteria). The width of plume at 6 cm from the nozzle for all fill volumes and in both 5 bar and 6 bar actuation pressure are in a range of 3 cm±1, thus passing the acceptance criterion. It is noted by the inventors of the present invention that the bi-modal spray pattern, comprising a first pattern and a second pattern; further wherein the first pattern is characterized by (a) Plume angle is in the range of 5°±4°; (b) width of plume at 6 cm from the nozzle is in the range of 4 mm±3 mm; and, the second pattern is characterized by (a) Plume angle is in the range of 35°±10; (b) width of plume at 6 cm from the nozzle is in the range of 30±10 mm; further wherein the mean particle's size in the first pattern is larger than the mean particle's size in the second pattern.

The overall characteristics of the SipNose delivery devices showed to have reproducibility of dose released, spray plume geometry and droplet size distribution which satisfied the acceptance criteria. Since all the above parameters can affect delivery of the drug substance to the intended biological target, it was shown that 200 µl, 400 µl and 600 µl and 800 µl of midazolam show same general aerosol characteristics, thus delivery of those volumes via the SipNose delivery system is acceptable, with either 5 bar or 6 bar actuation pressure. All results and calculations in this report reflect that the SipNose device passes all the acceptance criteria for SipNose as a nasal delivery device for midazolam and in general any other liquid drug delivery, and is comparable to the performances with Saline as a control. All volumes release highly similar aerosol in terms of aerosol characteristics, which is very unique in the field, that same device and technology (with no change at all) can fit such a range of volumes, and particularly high volumes and be so efficient in releasing the aerosolized drug.

Example 8

Investigation of the Aerosol and Insulin and Dose Delivery Characteristics of the Sipnose Nasal Delivery Device Materials & Equipment
As in Example 5.2
Results The results below, containing both aerosol characteristics and delivered doses corresponding insulin with specified drug volumes (100 µl and 200 µl) and specified pressures (5 and 6 bar) as defined.

Insulin Drug Solution—Delivered Dose Determination

The mean values and standard deviations are presented below. All individual data are presented below.

TABLE 21

Mean values of the delivered mass in %.
Delivered mass in % of loaded mass

| Drug Name | Sample (X bar) | Volumn µl | Mean | SD | RSD % |
|---|---|---|---|---|---|
| Insulin | A1(5b) | 100 µl | 93.8 | 2.7 | 2.8 |
|  | B1(5b) | 200 µl | 95.9 | 0.5 | 0.5 |

TABLE 22

Individual Insulin values for 5 bars actuation.

| Sample (x bar) | # | Drug Name | Volume | Empty- before g | with Air g | With Drug g | After dosing g | Air loaded mg | Drug Loaded mg | Drug residue mg | drug released mg | Delivered mass % of loaded | Mean | SD | RSD % |
|---|---|---|---|---|---|---|---|---|---|---|---|---|---|---|---|
| A1(5B) | 1 | Insulin | 100 | 8.5313 | 8.54701 | 8.6487 | 8.535 | 15.7 | 102.7 | 3.7 | 98.99 | 96.4 | 93.8 | 2.7 | 2.8 |
|  | 2 | Insulin | 100 | 8.565 | 8.5805 | 8.6777 | 8.5745 | 15.5 | 97.2 | 9.5 | 87.7 | 90.2 |  |  |  |
|  | 3 | Insulin | 100 | 8.53957 | 8.5551 | 8.6574 | 8.5488 | 15.5 | 102.3 | 9.2 | 93.07 | 91.0 |  |  |  |
|  | 4 | Insulin | 100 | 8.5313 | 8.547 | 8.646 | 8.5351 | 15.7 | 99.0 | 3.8 | 95.2 | 96.2 |  |  |  |
|  | 5 | Insulin | 100 | 8.52585 | 8.5414 | 8.5485 | 8.5324 | 15.5 | 107.1 | 6.6 | 100.55 | 93.9 |  |  |  |
|  | 6 | Insulin | 100 | 8.599 | 8.61454 | 8.7183 | 8.6039 | 15.5 | 103.8 | 4.9 | 98.86 | 95.3 |  |  |  |
| B1(5B) | 1 | Insulin | 200 | 8.5169 | 8.5325 | 8.7375 | 8.5253 | 15.6 | 205.0 | 8.4 | 196.6 | 95.9 | 95.9 | 0.5 | 0.5 |
|  | 2 | Insulin | 200 | 8.51042 | 8.5258 | 8.73075 | 8.5179 | 15.4 | 205.0 | 7.5 | 197.51 | 96.4 |  |  |  |
|  | 3 | Insulin | 200 | 8.5201 | 8.5356 | 8.7366 | 8.5283 | 15.5 | 201.0 | 8.2 | 192.8 | 95.9 |  |  |  |
|  | 4 | Insulin | 200 | 8.5259 | 8.5419 | 8.7397 | 8.5342 | 16.0 | 197.8 | 8.3 | 189.5 | 95.8 |  |  |  |
|  | 5 | Insulin | 200 | 8.5241 | 8.5398 | 8.7468 | 8.532 | 15.7 | 207.0 | 7.9 | 199.1 | 96.2 |  |  |  |
|  | 6 | Insulin | 200 | 8.5195 | 8.5349 | 8.7385 | 8.5299 | 15.3 | 203.6 | 10.3 | 191.3 | 94.9 |  |  |  |

The mean result for dose release for insulin formulation is 95.73±4.80 µl for 100 µl intended dose and 194.80±3.56 µl for 200 µl intended dose with a pressure of 5 bars. In all of the above cases, the released dose results pass the acceptance criterion (losses less than 10% of target weight).

Droplet Size Determination by Malvern Spraytec

TABLE 23

Individual results for Malvern Spraytec for insulin.

| Run | Label | Volume (ul) | Pressure (Bar) | Average Dv(50) (um) | Average Dv(10) (um) | Actuation times(ms) | Mean Dv(50) (um) | SD | Mean Actuation time(ms) | SD | Mean Dv(10) (um) | SD |
|---|---|---|---|---|---|---|---|---|---|---|---|---|
| 1 | Insulin A1 | 100 | 5 | 66.6 | 19 | 43 | 64.45 | 1.59 | 50.83 | 7.73 | 18.15 | 0.78 |
| 2 | Insulin A1 | 100 | 5 | 63.7 | 17.9 | 46 | | | | | | |
| 3 | Insulin A1 | 100 | 5 | 66.3 | 16.8 | 62 | | | | | | |
| 4 | Insulin A1 | 100 | 5 | 63.2 | 18.8 | 57 | | | | | | |
| 5 | Insulin A1 | 100 | 5 | 63.9 | 18.1 | 44 | | | | | | |
| 6 | Insulin A1 | 100 | 5 | 63 | 18.3 | 53 | | | | | | |
| 1 | Insulin B1 | 200 | 5 | 71.5 | 18.2 | 67 | 66.17 | 6.67 | 71.50 | 8.24 | 16.92 | 1.68 |
| 2 | Insulin B1 | 200 | 5 | 75.1 | 19.3 | 82 | | | | | | |
| 3 | Insulin B1 | 200 | 5 | 56.1 | 14.8 | 68 | | | | | | |
| 4 | Insulin B1 | 200 | 5 | 63.9 | 16.1 | 64 | | | | | | |
| 5 | Insulin B1 | 200 | 5 | 63.5 | 15.7 | 66 | | | | | | |
| 6 | Insulin B1 | 200 | 5 | 66.9 | 17.4 | 82 | | | | | | |

The particle size distribution for 100 µl and 200 µl insulin dose volumes show a bimodal behavior with one peak above 100 µm and one below 100 µm. In the time sequence distributions, there is an initial stable part with a higher transmission around 90% to 95%. Following this initial stable part comes a time period where the transmission drops markedly and then again increases to 99%. The DV(50) value of the 100 µl insulin volume (64.45 µm±1.59) and for the 200 µl insulin volume (66.17 µm±6.67) both pass the acceptance criterion. The DV(10) value of the 100 µl insulin volume (18.15 µm±0.78) and for the 200 µl insulin volume (16.92 µm±1.68) also pass the acceptance criterion.

Spray Pattern and Plume Geometry as measured by the Oxford Laser Envision

TABLE 24

Individual results for the spray pattern as measured by the Oxford Laser Envision
Spray Pattern

| Run | Label | Volume (ul) | Pressure (Bar) | Short axis (cm) | Long axis (cm) | Oblongation | Mean | SD | SD % |
|---|---|---|---|---|---|---|---|---|---|
| 1 | Insulin A1 | 100 | 5 | 1.69 | 3.01 | 1.78 | 1.67 | 0.192 | 11.50 |
| 2 | Insulin A1 | 100 | 5 | 2.03 | 3.61 | 1.78 | | | |
| 3 | Insulin A1 | 100 | 5 | 2.37 | 3.43 | 1.45 | | | |
| 1 | Insulin B1 | 200 | 5 | 2.25 | 3.07 | 1.36 | 1.46 | 0.190 | 13.00 |
| 2 | Insulin B1 | 200 | 5 | 2.14 | 3.6 | 1.68 | | | |
| 3 | Insulin B1 | 200 | 5 | 2.25 | 3.02 | 1.34 | | | |

Plume Geometry

TABLE 25

Individual results as measured by the Malvern Spraytec
Plume Geometry

| Run | Label | Volume (ul) | Pressure (Bar) | Angle (Deg) | Width (at 6 cm) | Angle Mean | Angle SD | Angle SD % | Width Mean | Width SD | Width SD % |
|---|---|---|---|---|---|---|---|---|---|---|---|
| 1 | Insulin A1 | 100 | 5 | 38.7 | 2.22 | 36.90 | 2.03 | 5.50 | 2.69 | 0.42 | 15.69 |
| 2 | Insulin A1 | 100 | 5 | 37.3 | 3.04 | | | | | | |
| 3 | Insulin A1 | 100 | 5 | 34.7 | 2.8 | | | | | | |
| 1 | Insulin B1 | 200 | 5 | 33.9 | 2.54 | 35.23 | 3.31 | 9.39 | 2.77 | 0.49 | 17.79 |
| 2 | Insulin B1 | 200 | 5 | 39 | 3.34 | | | | | | |
| 3 | Insulin B1 | 200 | 5 | 32.8 | 2.44 | | | | | | |

The overall (total) spray pattern means oblongation indexes for the 100 µl 200 µl of Insulin are 1.67±0.19 and 1.46±0.19 respectively, thus they pass the acceptance criteria. The overall (total) plume geometry angle mean values are of 36.9±2 degrees for the 100 µl and 35.23±3.31 for the 200 µl, with widths of 2.69±0.42 cm and 2.6 cm for 100 µl and 2.77±0.49 cm for 200 µl measured at a distance of 6 cm from the device orifice, thus they also pass the acceptance criteria.

It is noted by the inventors of the present invention that the bi-modal spray pattern, comprising a first pattern and a second pattern; further wherein the first pattern is characterized by (a) Plume angle is in the range of 5°±4°; (b) width of plume at 6 cm from the nozzle is in the range of 4 mm±3 mm; and, the second pattern is characterized by (a) Plume angle is in the range of 35°±10; (b) width of plume at 6 cm from the nozzle is in the range of 30±10 mm; further wherein the mean particle's size in the first pattern is larger than the mean particle's size in the second pattern.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The invention claimed is:

1. A device configured to deliver one or more substances within at least one body cavity of a subject, the device comprising:

at least one vial comprising a predetermined volume $V_{sub}$ [ml or mg] of said substances;

said at least one vial having a fluid inlet and a fluid discharging outlet, the fluid discharging outlet having a diameter D [mm] and being configured for placement in proximity to said at least one body cavity;

said fluid inlet configured by means of size and shape to interface in a sealable manner with at least one puncturing member, the at least one puncturing member being configured to pierce the fluid inlet upon coupling to the fluid inlet, thereby providing said one or more substances in a fluid communication, via at least one valve, with at least one chamber configured to accept pressurized fluid at a volume $V_{PF}$ [ml] and a pressure $P_{PF}$ [barg];

said valve is commutable from a CLOSED CONFIGURATION to an OPEN CONFIGURATION within a period of time dT, the period of time dT being less than 500 milliseconds;

wherein when the valve is in said OPEN CONFIGURATION, said pressurized fluid flows from said at least one chamber via said fluid inlet and entrains said one or more substances such that the pressurized fluid erupts via said fluid discharging outlet to within said at least one body cavity in the form of an aerosol;

wherein a release time $dT_{release}$ of said $V_{sub}$ [ml or mg] of said one or more substances and said $V_{PF}$ [ml] of said pressurized fluid is less than 500 milliseconds;

wherein a composition of the aerosol exiting said fluid discharging outlet into said at least one body cavity forms a bi-modal spray pattern, the bi-modal spray pattern having a first plume angle of less than 25° in a first portion and a second plume angle of approximately 35°±10° in a second portion.

2. The device of claim 1, wherein said at least one chamber comprises a port fluidly connectable to the exterior of said device, said port configured such that said at least one substance is insertable into said at least one chamber via said port.

3. The device of claim 2, wherein said device comprises a port cover configured to provide an air-tight closure for said port, said port cover being configured to articulate relative to the device via at least one of sliding along said device, rotating around said device, or rotating about a hinge on an exterior of said device.

4. The device of claim 1, wherein said vial is blow-molded, filled and sealed in a continuous manufacturing process.

5. The device of claim 1, wherein a velocity of particles within the aerosol ranges from 5 m/s to 50 m/s.

6. The device of claim 1, wherein said at least one substance comprises at least one of a gas, a liquid, a powder, an aerosol, a slurry, a gel, or a suspension.

7. The device of claim 1, wherein the at least one chamber is configured to contain a predetermined volume $V_{gas}$ [ml] of pressurized gas at a predetermined pressure $P_{gas}$; and wherein at least one of the following is true:

a) the device is configured to deliver the one or more substances within at least one of a nasal cavity, a mouth, a throat, an ear, a vagina, a rectum, a urethra;

b) said pressurized gas is selected from a group consisting of air, nitrogen, oxygen, carbon dioxide, helium, neon, xenon and any combination thereof;

c) during dispensing of said at least one substance, a mixture of said predetermined volume $V_{gas}$ [ml] of said pressurized gas with said predetermined volume $V_{sub}$ [ml or mg] of said at least one substance entrained within it forms the aerosol;

said aerosol having a predetermined distribution, said distribution being either homogeneous or heterogeneous, said heterogeneous distribution being selected from a group consisting of: an arbitrary distribution, a distribution in which a density of said at least one substance within said mixture follows a predetermined pattern, and any combination thereof; wherein at least one characteristic of the aerosol is based on at least one characteristic of the device, the at least one characteristic of the aerosol comprising at least one of a particle size, particle shape, particle distribution, and the at least one characteristic of the device comprising at least one of said predetermined volume of said pressurized gas, said predetermined volume of said substance, said predetermined pressure of said pressurized gas, or said diameter D [mm] of the fluid discharging outlet;

d) at least one said substance is stored under one of the followings: an inert atmosphere; under vacuum and a pressure above ambient pressure to prevent reactions during storage;

e) when the at least one substance is administered nasally via the device, a dose-response curve of a concentration of the at least one substance within a brain of the subject is substantially linear and f) when the at least one substance is administered nasally via the device, a fit of a dose-response curve of a concentration of the at least one substance within a brain of the subject is logarithmic, parabolic, exponential, sigmoid, power-low, or any combination thereof.

8. The device of claim 1, wherein said vial is a capsule having a main longitudinal axis, said capsule comprising a number n of compartments, said capsule configured to contain said predetermined volume $V_{sub}$ [ml or mg] of said at least one substance, said volume $V_{sub}$ [ml or mg] of said at least one substance containable in at least one of said n compartments; at least one of the following being true:

a) the number n of said compartments is an integer greater than or equal to 1; at least one of the compartments has a cross-section with a shape selected from a group consisting of: wedge shaped, circular, oval, elliptical, polygonal, annular, and any combination thereof;

b) for said number n of compartments being an integer greater than 1, at least two of said compartments have different volumes;

c) for said number n of compartments being an integer greater than 1, at least two of said compartments have the same volume;

d) for said number n of compartments being an integer greater than 1, at least two of said compartments have different cross-sectional areas;

e) for said number n of compartments being an integer greater than 1, at least two of said compartments have a same cross-sectional area;
f) for said number n of compartments being an integer greater than 1, at least two of said compartments contain different substances;
g) for said number n of compartments being an integer greater than 1, at least two of said compartments contain the same substance;
h) for said number n of compartments being an integer greater than 1, at least two said compartments are disposed coaxially around said main longitudinal axis of said capsule;
i) for said number n of compartments being an integer greater than 1, at least two said compartments are disposed sequentially along said main longitudinal axis of said capsule;

j) for said number n of compartments greater than 1, said at least one substance mixes during said dispensing; and k) for said number n of compartments greater than 1, said at least one substance reacts during said dispensing.

9. The device of claim 1, wherein said pressurized fluid entrains said substance in a pulsed manner, such that a plurality of portions of $V_{PF}$ are emitted via said fluid discharging outlet to within said at least one body cavity.

10. The device of claim 1, wherein said substance is selected from a group consisting of: proteins; stem-cells; cells, organs, portions, extracts, and isolations thereof; macromolecules; RNA or other genes and proteins-encoding materials; neurotransmitters; receptor antagonists; hormones; Ketamine; commercially available by Lilly (US) Baqsimi product; Glucagon; substrates to treat one of the following: anaphylaxis, Parkinson, seizures and opioid overdose; epinephrine; atropine; metoclopramide; commercially available Naloxone or Narcan products; Esketamine (Spravato); Radicava [edaravone]; Ingrezza [valbenazine], Austedo [deutetrabenazine]; Midazolam, Insulin, Ocrevus [ocrelizumab]; Xadago [safinamide]; Spinraza [nusinersen]; Zinbryta [daclizumab]; Nuplazid [pimavanserin], Aristada [aripiprazole lauroxil]; Vraylar [cariprazine]; Rexulti [brexpiprazole]; Aptiom [eslicarbazepine acetate]; Vizamyl [flutemetamol F 18 injection]; Brintellix [vortioxetine], Tecfidera [dimethyl fumarate]; Dotarem [gadoterate meglumine]; Antibody mediated brain targeting drug delivery including aducanumab, gantenerumab, bapineuzumab, solanezumab, ofatumumab CD20, BIIB033, LCN2, HMGBI; insulin; oxytocin; orexin-A; leptin; benzodiazepine i.e. midazolam; naloxone; perillyl alcohol; camptothecin; phytochemicals including curcumin and chrysin; nucleotides; olanzapine; risperidone; Venlafaxin; GDF-5; zonisamide; ropinirole; plant-originated and synthetically-produced terpenes and cannabinoids, including THC and CBD; valproric acid; rivastigmine; estradiol; topiramate or an equivalent preparation comprising CAS No. 97240-79-4; MFSD2 or MFSD2A or sodium-dependent lysophosphatidylcholine symporter; and any esters, salts, derivatives, mixtures, combinations thereof, with or without a carrier, liposomes, lyophilic or watermiscible solvents, surfactants, cells, cells fractions, cells secreation/secrotomes at a therapeutically effective concentration.

11. The device of claim 1, wherein when the delivery of said predetermined volume $V_{sub}$ [ml or mg] of said at least one substance and said predetermined volume $V_{PF}$ of said pressurized gas through said fluid discharging outlet of diameter D [mm] in a pressure rate of $dP_{PF}/dT$ is provided, at least one of the following is held true:

a) said $P_{PF}$ is in a range of about 0 to about 10 barg;

b) said $V_{PF}$ is in a range of about 1 to about 50 ml;

c) said $V_{sub}$ is in a range of about 0.01 to about 7 ml;

d) said D is in a range of 0.2 to about 6 mm;

e) said pressure rate, $$\frac{dP}{dT} \to \infty;$$

and f) said pressure rate greater than about 0.001 barg/ms.

12. The device of claim 1, wherein a particle size of the bi-modal spray pattern is distributed such that it includes a first peak associated with a first particle size greater than 100 μm and a second peak associated with a second particle size less than 100 μm.

* * * * *